US012735502B2

(12) United States Patent
Blankenship et al.

(10) Patent No.: US 12,735,502 B2
(45) Date of Patent: Sep. 15, 2026

(54) IMMUNOGLOBULIN VARIANTS

(71) Applicant: Novartis AG, Basel (CH)

(72) Inventors: John Blankenship, Acton, MA (US); Justine Celine Patricia Guyot, Zimmersheim (FR); Brian Holmberg, Somerville, MA (US); Sebastien Irigaray, Zimmersheim (FR); Darko Skegro, Riehen (CH)

(73) Assignee: Novartis AG, Basel (CH)

(*) Notice: Subject to any disclaimer, the term of this patent is extended or adjusted under 35 U.S.C. 154(b) by 879 days.

(21) Appl. No.: 17/997,485

(22) PCT Filed: Apr. 29, 2021

(86) PCT No.: PCT/IB2021/053585
§ 371 (c)(1),
(2) Date: Oct. 28, 2022

(87) PCT Pub. No.: WO2021/220218
PCT Pub. Date: Nov. 4, 2021

(65) Prior Publication Data

US 2023/0167193 A1 Jun. 1, 2023

Related U.S. Application Data

(60) Provisional application No. 63/018,698, filed on May 1, 2020.

(51) Int. Cl.
*C07K 16/30* (2006.01)
*A61K 39/00* (2006.01)

(52) U.S. Cl.
CPC ........ *C07K 16/30* (2013.01); *A61K 2039/505* (2013.01); *C07K 2317/524* (2013.01); *C07K 2317/526* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2015/0266960 A1 | 9/2015 | Georgiou et al. | |
| 2019/0309085 A1 | 10/2019 | Monnet | |

FOREIGN PATENT DOCUMENTS

| | | | |
|---|---|---|---|
| EP | 2552955 | B1 | 5/2017 |
| WO | 2005123780 | A2 | 12/2005 |
| WO | 2006019447 | A1 | 2/2006 |
| WO | 2013004842 | A2 | 1/2013 |
| WO | 2014108198 | A1 | 7/2014 |

OTHER PUBLICATIONS

Su et al. (Antibodies, 2018, 7, 20) (Year: 2018).*
Brandsma, et al., Potent Fc Receptor Signaling by IgA Leads to Superior Killing of Cancer Cells by Neutrophils Compared to IgG, Frontiers in Immunlogy, Apr. 11, 2019, article 704, 10.
Lohse, et al., An Anti-EGFR IgA That Displays Improved Pharmacokinetics and Myeloid Effector Cell Engagement In Vivo, Cancer Research, Jan. 15, 2016, 403-417, 76(2).
Saunders, Conceptual Approaches to Modulating Antibody Effector Functions and Circulation Half-Life, Frontiers in Immunolgy, Jun. 7, 2019, article 1296, 10.
Van Gool, et al., IgA and Fc(alpha)RI: Versatile Players in Homeostasis, Infection, and Autoimmunity, Immunotargets and Therapy, 2020, 351-372, 9.
Pleass, et al., Identification of Residues in the CH2/CH3 Domain Interface of IgA Essential for Interaction with the Human Fca Receptor (FcaR) CD89, Journal of Biological Chemistry, 274(33), 23508-23514, Aug. 13, 1999.

* cited by examiner

*Primary Examiner* — Meera Natarajan
(74) *Attorney, Agent, or Firm* — Linyu L. Mitra

(57) ABSTRACT

The present invention provides an Fc variant of a parent IgA Fc polypeptide, wherein the Fc variant exhibits altered binding to FcαRs, wherein the Fc variant comprises at least one amino acid modification in the Fc region of the parent Fc polypeptide.

11 Claims, 7 Drawing Sheets

Specification includes a Sequence Listing.

PMN killing assay on SK-BR-3
Abs490
Concentration (nM)
SEQ ID 2
SEQ ID 7-8
SEQ ID 80-8
PBMC killing assay on SK-BR-3
Abs490
Concentration (nM)
SEQ ID 1
SEQ ID 7-8
SEQ ID 80-8
PMN killing assay on SK-BR-3
Abs490
Concentration (nM)
SEQ ID 2
SEQ ID 7-9
SEQ ID 80-9
PBMC killing assay on SK-BR-3
Abs490
Concentration (nM)
SEQ ID 1
SEQ ID 7-9
SEQ ID 80-9

SEQUENCE LISTING

```
<160> NUMBER OF SEQ ID NOS: 84

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445


<210> SEQ ID NO 2
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125
```

-continued

```
Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 3
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

-continued

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440
```

<210> SEQ ID NO 4
<211> LENGTH: 214

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Gln Glu Gly Asp Phe Pro Met Pro Phe Ile Ser Ala Lys Ser Ser Pro
1               5                   10                  15

Val Ile Pro Leu Asp Gly Ser Val Lys Ile Gln Cys Gln Ala Ile Arg
            20                  25                  30

Glu Ala Tyr Leu Thr Gln Leu Met Ile Ile Lys Asn Ser Thr Tyr Arg
        35                  40                  45

Glu Ile Gly Arg Arg Leu Lys Phe Trp Asn Glu Thr Asp Pro Glu Phe
    50                  55                  60

Val Ile Asp His Met Asp Ala Asn Lys Ala Gly Arg Tyr Gln Cys Gln
65                  70                  75                  80

Tyr Arg Ile Gly His Tyr Arg Phe Arg Tyr Ser Asp Thr Leu Glu Leu
                85                  90                  95
```

```
Val Val Thr Gly Leu Tyr Gly Lys Pro Phe Leu Ser Ala Asp Arg Gly
            100                 105                 110

Leu Val Leu Met Pro Gly Glu Asn Ile Ser Leu Thr Cys Ser Ser Ala
        115                 120                 125

His Ile Pro Phe Asp Arg Phe Ser Leu Ala Lys Glu Gly Glu Leu Ser
    130                 135                 140

Leu Pro Gln His Gln Ser Gly Glu His Pro Ala Asn Phe Ser Leu Gly
145                 150                 155                 160

Pro Val Asp Leu Asn Val Ser Gly Ile Tyr Arg Cys Tyr Gly Trp Tyr
                165                 170                 175

Asn Arg Ser Pro Tyr Leu Trp Ser Phe Pro Ser Asn Ala Leu Glu Leu
            180                 185                 190

Val Val Thr Asp Ser Ile His Gln Asp Tyr Thr Thr Gln Asn His His
        195                 200                 205

His His His His Gly Leu Asn Asp Ile Phe Glu Ala Gln Lys Ile Glu
    210                 215                 220

Trp His Glu
225


<210> SEQ ID NO 6
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

Lys Thr His Thr Cys Pro Pro Cys Pro Ala Pro Glu Leu Leu Gly Gly
225 230 235 240

Pro Ser Val Phe Leu Phe Arg Pro Ala Leu Glu Asp Leu Leu Leu Gly
245 250 255

Ser Glu Ala Asn Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Gly Gln Pro Arg Glu Pro Gln Val Tyr Leu Leu
340 345 350

Pro Pro Ser Arg Asp Glu Leu Thr Lys Asn Gln Val Ser Leu Thr Cys
355 360 365

Leu Ala Lys Gly Phe Tyr Pro Lys Asp Val Leu Val Arg Trp Leu Gln
370 375 380

Gly Ser Gln Glu Leu Pro Arg Glu Asn Tyr Lys Thr Thr Ala Ser Val
385 390 395 400

Leu Asp Ser Asp Gly Ser Phe Phe Val Tyr Ser Lys Leu Thr Val Ala
405 410 415

Ala Glu Asp Trp Lys Lys Gly Asp Thr Phe Ser Cys Met Val Gly His
420 425 430

Glu Ala Leu Pro Leu Ala Phe Thr Gln Lys Ser Ile Ser Arg Ser Pro
435 440 445

<210> SEQ ID NO 7
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala

-continued

```
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Cys Leu Leu
            340                 345                 350

Pro Pro Ser Arg Asp Glu Leu Thr Lys Asn Gln Val Ser Leu Ser Cys
        355                 360                 365

Ala Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Val Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 8
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

-continued

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 9
<211> LENGTH: 447
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                325                 330                 335

Lys Thr Ile Ser Lys Ala Gly Gln Pro Arg Glu Pro Gln Val Tyr Thr
            340                 345                 350

Leu Pro Pro Cys Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380
```

-continued

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 10
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Glu Pro Trp Asn
    290                 295                 300
```

```
His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 11
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
```

-continued

```
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 12
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125
```

-continued

```
Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 13
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Gln Lys Thr Ile Asp Arg Leu Ala
        435                 440
```

<210> SEQ ID NO 14
<211> LENGTH: 440

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380
```

```
Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Tyr Lys Thr Ile Asp Arg Leu Ala
        435                 440


<210> SEQ ID NO 15
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Glu Pro Trp Tyr
```

-continued

```
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 16
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440

<210> SEQ ID NO 17
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440
```

<210> SEQ ID NO 18
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440
```

<210> SEQ ID NO 19

-continued

```
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
```

```
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Gln Lys Ser Ile Ser Arg Ser Pro
        435                 440


<210> SEQ ID NO 20
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285
```

-continued

```
Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Tyr Lys Ser Ile Ser Arg Ser Pro
        435                 440
```

<210> SEQ ID NO 21
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440


<210> SEQ ID NO 22
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

-continued

```
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

<210> SEQ ID NO 23
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

-continued

<210> SEQ ID NO 24
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365
```

-continued

```
Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 25
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

-continued

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445

<210> SEQ ID NO 26
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

```
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
            245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
            405                 410                 415

Ala Glu Asp Trp Lys Lys Gly Asp Thr Phe Ser Cys Met Val Gly His
            420                 425                 430

Glu Ala Leu Pro Leu Ala Phe Thr Tyr Lys Ser Ile Ser Arg Ser Pro
        435                 440                 445


<210> SEQ ID NO 27
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110
```

-continued

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 28
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Tyr Lys Thr Ile Asp Arg Leu Ala
        435                 440
```

<210> SEQ ID NO 29
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

```
Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Tyr Lys Thr Ile Asp Arg Leu Ala
        435                 440


<210> SEQ ID NO 30
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
```

```
        275                 280                 285

Cys Tyr Ser Val Ser Ser Val Leu Pro Gly Cys Ala Glu Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 31
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190
```

-continued

```
Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Glu Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Tyr Lys Thr Ile Asp Arg Leu Ala
        435                 440


<210> SEQ ID NO 32
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

Gly Thr Leu Val Thr Val Ser Ser Ala Ser Pro Thr Ser Pro Lys Val
115 120 125

Phe Pro Leu Ser Leu Asp Ser Thr Pro Gln Asp Gly Asn Val Val Val
130 135 140

Ala Cys Leu Val Gln Gly Phe Phe Pro Gln Glu Pro Leu Ser Val Thr
145 150 155 160

Trp Ser Glu Ser Gly Gln Asn Val Thr Ala Arg Asn Phe Pro Pro Ser
165 170 175

Gln Asp Ala Ser Gly Asp Leu Tyr Thr Thr Ser Ser Gln Leu Thr Leu
180 185 190

Pro Ala Thr Gln Cys Pro Asp Gly Lys Ser Val Thr Cys His Val Lys
195 200 205

His Tyr Thr Asn Pro Ser Gln Asp Val Thr Val Pro Cys Arg Val Pro
210 215 220

Pro Pro Pro Pro Cys Cys His Pro Arg Leu Ser Leu His Arg Pro Ala
225 230 235 240

Leu Glu Asp Leu Leu Leu Gly Ser Glu Ala Asn Leu Thr Cys Thr Leu
245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Glu Pro Trp Tyr
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu
340 345 350

Val Thr Leu Thr Cys Leu Ala Arg Gly Phe Ser Pro Lys Asp Val Leu
355 360 365

Val Arg Trp Leu Gln Gly Asp Gln Glu Leu Pro Arg Glu Lys Tyr Leu
370 375 380

Thr Trp Ala Ser Arg Gln Glu Pro Ser Gln Gly Thr Thr Thr Phe Ala
385 390 395 400

Val Thr Ser Ile Leu Arg Val Ala Ala Glu Asp Trp Lys Lys Gly Asp
405 410 415

Thr Phe Ser Cys Tyr Val Gly His Glu Ala Leu Pro Leu Ala Phe Thr
420 425 430

Tyr Lys Thr Ile Asp Arg Leu Ala
435 440

<210> SEQ ID NO 33
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr

-continued

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Tyr Lys Ser Ile Ser Arg Ser Pro
        435                 440
```

<210> SEQ ID NO 34
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
```

```
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Tyr Lys Ser Ile Ser Arg Ser Pro
        435                 440


<210> SEQ ID NO 35
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270
```

```
Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440


<210> SEQ ID NO 36
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Tyr Lys Ser Ile Ser Arg Ser Pro
        435                 440


<210> SEQ ID NO 37
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

```
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Tyr Lys Ser Ile Ser Arg Ser Pro
        435                 440


<210> SEQ ID NO 38
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Tyr Lys Ser Ile Ser Arg Ser Pro
```

```
        435                 440                 445


<210> SEQ ID NO 39
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350
```

```
Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Tyr Lys Ser Ile Ser Arg Ser Pro
        435                 440                 445


<210> SEQ ID NO 40
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 41
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

-continued

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Tyr Lys Ser Ile Ser Arg Ser Pro
        435                 440                 445


<210> SEQ ID NO 42
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

-continued

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Tyr Lys Ser Ile Ser Arg Ser Pro
        435                 440                 445
```

<210> SEQ ID NO 43
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ser
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430
```

```
Gln Lys Thr Ile Asp Arg Leu Ala
        435                 440


<210> SEQ ID NO 44
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Ile Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350
```

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440

<210> SEQ ID NO 45
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser

```
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Val Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 46
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175
```

-continued

```
Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Trp Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 47
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

-continued

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Asp Ala Leu Pro Leu Ala Phe Thr
            420                 425                 430

Gln Lys Thr Ile Asp Arg Leu Ala
        435                 440
```

<210> SEQ ID NO 48
<211> LENGTH: 440
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

```
Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430
```

Gln Lys Thr Ile Asp Arg Phe Ala
435 440

<210> SEQ ID NO 49
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Pro Thr Ser Pro Lys Val
115 120 125

Phe Pro Leu Ser Leu Asp Ser Thr Pro Gln Asp Gly Asn Val Val Val
130 135 140

Ala Cys Leu Val Gln Gly Phe Phe Pro Gln Glu Pro Leu Ser Val Thr
145 150 155 160

Trp Ser Glu Ser Gly Gln Asn Val Thr Ala Arg Asn Phe Pro Pro Ser
165 170 175

Gln Asp Ala Ser Gly Asp Leu Tyr Thr Thr Ser Ser Gln Leu Thr Leu
180 185 190

Pro Ala Thr Gln Cys Pro Asp Gly Lys Ser Val Thr Cys His Val Lys
195 200 205

His Tyr Thr Asn Pro Ser Gln Asp Val Thr Val Pro Cys Arg Val Pro
210 215 220

Pro Pro Pro Pro Cys Cys His Pro Arg Leu Ser Leu His Arg Pro Ala
225 230 235 240

Leu Glu Asp Leu Leu Leu Gly Ser Glu Ala Asn Leu Thr Cys Thr Leu
245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Ile Pro Val Cys Ala Glu Pro Trp Tyr
290 295 300

His Trp Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu

-continued

```
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 50
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255
```

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Gln Pro Trp His
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu
340 345 350

Val Thr Leu Thr Cys Leu Ala Arg Gly Phe Ser Pro Lys Asp Val Leu
355 360 365

Val Arg Trp Leu Gln Gly Ser Gln Glu Leu Pro Arg Glu Lys Tyr Leu
370 375 380

Thr Trp Ala Ser Arg Gln Glu Pro Ser Gln Gly Thr Thr Thr Phe Ala
385 390 395 400

Val Thr Ser Ile Leu Arg Val Ala Ala Glu Asp Trp Lys Lys Gly Asp
405 410 415

Thr Phe Ser Cys Met Val Gly His Glu Ala Leu Pro Leu Ala Phe Thr
420 425 430

Gln Lys Thr Ile Asp Arg Leu Ala
435 440

<210> SEQ ID NO 51
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Ile
    290                 295                 300

Thr Val Leu His Glu Asp Trp Tyr Asn Trp Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440


<210> SEQ ID NO 52
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

-continued

```
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Ile Thr Val Leu His Glu Asp Trp Tyr Asn Trp Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

<210> SEQ ID NO 53
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Glu Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
```

420 425 430

Gln Lys Thr Ile Asp Arg Leu Ala
435 440

<210> SEQ ID NO 54
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Pro Thr Ser Pro Lys Val
115 120 125

Phe Pro Leu Ser Leu Asp Ser Thr Pro Gln Asp Gly Asn Val Val Val
130 135 140

Ala Cys Leu Val Gln Gly Phe Phe Pro Gln Glu Pro Leu Ser Val Thr
145 150 155 160

Trp Ser Glu Ser Gly Gln Asn Val Thr Ala Arg Asn Phe Pro Pro Ser
165 170 175

Gln Asp Ala Ser Gly Asp Leu Tyr Thr Thr Ser Ser Gln Leu Thr Leu
180 185 190

Pro Ala Thr Gln Cys Pro Asp Gly Lys Ser Val Thr Cys His Val Lys
195 200 205

His Tyr Thr Asn Pro Ser Gln Asp Val Thr Val Pro Cys Arg Val Pro
210 215 220

Pro Pro Pro Pro Cys Cys His Pro Arg Leu Ser Leu His Arg Pro Ala
225 230 235 240

Leu Glu Asp Leu Leu Leu Gly Ser Glu Ala Asn Leu Thr Cys Thr Leu
245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Glu Pro Trp Asn
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

```
Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Gln Lys Thr Ile Asp Arg Leu Ala
        435                 440


<210> SEQ ID NO 55
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255
```

```
Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Met Val Gly His Glu Ala Leu Pro Leu Ala Phe Thr
            420                 425                 430

Gln Lys Thr Ile Asp Arg Leu Ala
        435                 440


<210> SEQ ID NO 56
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
```

-continued 165 170 175

Gln Asp Ala Ser Gly Asp Leu Tyr Thr Thr Ser Ser Gln Leu Thr Leu
180 185 190

Pro Ala Thr Gln Cys Pro Asp Gly Lys Ser Val Thr Cys His Val Lys
195 200 205

His Tyr Thr Asn Pro Ser Gln Asp Val Thr Val Pro Cys Arg Val Pro
210 215 220

Pro Pro Pro Pro Cys Cys His Pro Arg Leu Ser Leu His Arg Pro Ala
225 230 235 240

Leu Glu Asp Leu Leu Leu Gly Ser Glu Ala Asn Leu Thr Cys Thr Leu
245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Gln Pro Trp Tyr
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu
340 345 350

Val Thr Leu Thr Cys Leu Ala Arg Gly Phe Ser Pro Lys Asp Val Leu
355 360 365

Val Arg Trp Leu Gln Gly Ser Gln Glu Leu Pro Arg Glu Lys Tyr Leu
370 375 380

Thr Trp Ala Ser Arg Gln Glu Pro Ser Gln Gly Thr Thr Thr Phe Ala
385 390 395 400

Val Thr Ser Ile Leu Arg Val Ala Ala Glu Asp Trp Lys Lys Gly Asp
405 410 415

Thr Phe Ser Cys Tyr Val Gly His Glu Ala Leu Pro Leu Ala Phe Thr
420 425 430

Gln Lys Thr Ile Asp Arg Leu Ala
435 440

<210> SEQ ID NO 57
<211> LENGTH: 440
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Asn
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Gln Lys Thr Ile Asp Arg Leu Ala
        435                 440
```

<210> SEQ ID NO 58
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Glu Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335

Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Ser Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415
```

```
Thr Phe Ser Cys Tyr Val Gly His Glu Ala Leu Pro Leu Ala Phe Thr
            420                 425                 430

Gln Lys Thr Ile Asp Arg Leu Ala
        435                 440
```

<210> SEQ ID NO 59
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
                245                 250                 255

Thr Gly Leu Arg Asp Ala Ser Gly Ala Thr Phe Thr Trp Thr Pro Ser
            260                 265                 270

Ser Gly Lys Ser Ala Val Gln Gly Pro Pro Glu Arg Asp Leu Cys Gly
        275                 280                 285

Cys Tyr Ser Val Ser Ser Val Leu Pro Gly Cys Ala Gln Pro Trp Tyr
    290                 295                 300

His Gly Glu Thr Phe Thr Cys Thr Ala Ala His Pro Glu Leu Lys Thr
305                 310                 315                 320

Pro Leu Thr Ala Asn Ile Thr Lys Ser Gly Asn Thr Phe Arg Pro Glu
                325                 330                 335
```

```
Val His Leu Leu Pro Pro Pro Ser Glu Glu Leu Ala Leu Asn Glu Leu
            340                 345                 350

Val Thr Leu Thr Cys Leu Ala Arg Gly Phe Ser Pro Lys Asp Val Leu
        355                 360                 365

Val Arg Trp Leu Gln Gly Asp Gln Glu Leu Pro Arg Glu Lys Tyr Leu
    370                 375                 380

Thr Trp Ala Ser Arg Gln Glu Pro Ser Gln Gly Thr Thr Thr Phe Ala
385                 390                 395                 400

Val Thr Ser Ile Leu Arg Val Ala Ala Glu Asp Trp Lys Lys Gly Asp
                405                 410                 415

Thr Phe Ser Cys Tyr Val Gly His Glu Ala Leu Pro Leu Ala Phe Thr
            420                 425                 430

Gln Lys Thr Ile Asp Arg Leu Ala
        435                 440


<210> SEQ ID NO 60
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Pro Thr Ser Pro Lys Val
        115                 120                 125

Phe Pro Leu Ser Leu Asp Ser Thr Pro Gln Asp Gly Asn Val Val Val
    130                 135                 140

Ala Cys Leu Val Gln Gly Phe Phe Pro Gln Glu Pro Leu Ser Val Thr
145                 150                 155                 160

Trp Ser Glu Ser Gly Gln Asn Val Thr Ala Arg Asn Phe Pro Pro Ser
                165                 170                 175

Gln Asp Ala Ser Gly Asp Leu Tyr Thr Thr Ser Ser Gln Leu Thr Leu
            180                 185                 190

Pro Ala Thr Gln Cys Pro Asp Gly Lys Ser Val Thr Cys His Val Lys
        195                 200                 205

His Tyr Thr Asn Pro Ser Gln Asp Val Thr Val Pro Cys Arg Val Pro
    210                 215                 220

Pro Pro Pro Pro Cys Cys His Pro Arg Leu Ser Leu His Arg Pro Ala
225                 230                 235                 240

Leu Glu Asp Leu Leu Leu Gly Ser Glu Ala Asn Leu Thr Cys Thr Leu
```

245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Glu Pro Trp Asn
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu
340 345 350

Val Thr Leu Thr Cys Leu Ala Arg Gly Phe Ser Pro Lys Asp Val Leu
355 360 365

Val Arg Trp Leu Gln Gly Asp Gln Glu Leu Pro Arg Glu Lys Tyr Leu
370 375 380

Thr Trp Ala Ser Arg Gln Glu Pro Ser Gln Gly Thr Thr Thr Phe Ala
385 390 395 400

Val Thr Ser Ile Leu Arg Val Ala Ala Glu Asp Trp Lys Lys Gly Asp
405 410 415

Thr Phe Ser Cys Tyr Val Gly His Glu Ala Leu Pro Leu Ala Phe Thr
420 425 430

Gln Lys Thr Ile Asp Arg Leu Ala
435 440

<210> SEQ ID NO 61
<211> LENGTH: 440
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Pro Thr Ser Pro Lys Val
115 120 125

Phe Pro Leu Ser Leu Asp Ser Thr Pro Gln Asp Gly Asn Val Val Val
130 135 140

Ala Cys Leu Val Gln Gly Phe Phe Pro Gln Glu Pro Leu Ser Val Thr
145 150 155 160

-continued

Trp Ser Glu Ser Gly Gln Asn Val Thr Ala Arg Asn Phe Pro Pro Ser
165 170 175

Gln Asp Ala Ser Gly Asp Leu Tyr Thr Thr Ser Ser Gln Leu Thr Leu
180 185 190

Pro Ala Thr Gln Cys Pro Asp Gly Lys Ser Val Thr Cys His Val Lys
195 200 205

His Tyr Thr Asn Pro Ser Gln Asp Val Thr Val Pro Cys Arg Val Pro
210 215 220

Pro Pro Pro Pro Cys Cys His Pro Arg Leu Ser Leu His Arg Pro Ala
225 230 235 240

Leu Glu Asp Leu Leu Leu Gly Ser Glu Ala Asn Leu Thr Cys Thr Leu
245 250 255

Thr Gly Leu Arg Asp Ala Ser Gly Ala Thr Phe Thr Trp Thr Pro Ser
260 265 270

Ser Gly Lys Ser Ala Val Gln Gly Pro Pro Glu Arg Asp Leu Cys Gly
275 280 285

Cys Tyr Ser Val Ser Ser Val Leu Pro Gly Cys Ala Glu Pro Trp Tyr
290 295 300

His Gly Glu Thr Phe Thr Cys Thr Ala Ala His Pro Glu Leu Lys Thr
305 310 315 320

Pro Leu Thr Ala Asn Ile Thr Lys Ser Gly Asn Thr Phe Arg Pro Glu
325 330 335

Val His Leu Leu Pro Pro Pro Ser Glu Glu Leu Ala Leu Asn Glu Leu
340 345 350

Val Thr Leu Thr Cys Leu Ala Arg Gly Phe Ser Pro Lys Asp Val Leu
355 360 365

Val Arg Trp Leu Gln Gly Asp Gln Glu Leu Pro Arg Glu Lys Tyr Leu
370 375 380

Thr Trp Ala Ser Arg Gln Glu Pro Ser Gln Gly Thr Thr Thr Phe Ala
385 390 395 400

Val Thr Ser Ile Leu Arg Val Ala Ala Glu Asp Trp Lys Lys Gly Asp
405 410 415

Thr Phe Ser Cys Tyr Val Gly His Glu Ala Leu Pro Leu Ala Phe Thr
420 425 430

Gln Lys Thr Ile Asp Arg Leu Ala
435 440

<210> SEQ ID NO 62
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Cys Cys His Pro Arg Val Phe
225 230 235 240

Leu Phe Arg Pro Ala Leu Glu Asp Leu Leu Leu Gly Ser Glu Ala Asn
245 250 255

Val Thr Cys Val Val Thr Gly Leu Arg Asp Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Cys Gly Cys Tyr Ser Val Val Ser Val Leu
290 295 300

Thr Val Leu His Glu Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Gly Gln Pro Arg Glu Pro Gln Val Tyr Leu Leu Pro Pro Ser Arg
340 345 350

Asp Glu Leu Thr Lys Asn Gln Val Ser Leu Thr Cys Leu Ala Lys Gly
355 360 365

Phe Tyr Pro Lys Asp Val Leu Val Arg Trp Leu Gln Gly Asp Gln Glu
370 375 380

Leu Pro Arg Glu Asn Tyr Lys Thr Thr Ala Ser Val Leu Asp Ser Asp
385 390 395 400

Gly Ser Phe Phe Val Tyr Ser Lys Leu Thr Val Ala Ala Glu Asp Trp
405 410 415

Lys Lys Gly Asp Thr Phe Ser Cys Met Val Gly His Glu Ala Leu Pro
420 425 430

Leu Ala Phe Thr Gln Lys Ser Ile Ser Arg Ser Pro
435 440

<210> SEQ ID NO 63
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415
```

-continued

```
Lys Lys Gly Asp Thr Phe Ser Cys Tyr Val Gly His Glu Ala Leu Pro
            420                 425                 430

Leu Ala Phe Thr Gln Lys Ser Ile Ser Arg Ser Pro
        435                 440


<210> SEQ ID NO 64
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Met Val Gly His Glu Ala Leu Pro
            420                 425                 430

Leu Ala Phe Thr Gln Lys Ser Ile Ser Arg Ser Pro
        435                 440


<210> SEQ ID NO 65
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240
```

-continued

```
Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Ser Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Gln Lys Ser Ile Ser Arg Ser Pro
        435                 440


<210> SEQ ID NO 66
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp
                405                 410                 415

Lys Lys Gly Asp Thr Phe Ser Cys Tyr Val Gly His Glu Ala Leu Pro
            420                 425                 430

Leu Ala Phe Thr Gln Lys Ser Ile Ser Arg Ser Pro
        435                 440
```

<210> SEQ ID NO 67
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
```

-continued 65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Cys Cys His Pro Arg Val Phe
225 230 235 240

Leu Phe Arg Pro Ala Leu Glu Asp Leu Leu Leu Gly Ser Glu Ala Asn
245 250 255

Val Thr Cys Val Val Thr Gly Leu Arg Asp Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Cys Gly Cys Tyr Ser Val Val Ser Val Leu
290 295 300

Thr Val Leu His Glu Asp Trp Tyr Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Gly Gln Pro Arg Glu Pro Gln Val Tyr Leu Leu Pro Pro Ser Arg
340 345 350

Asp Glu Leu Thr Lys Asn Gln Val Ser Leu Thr Cys Leu Ala Lys Gly
355 360 365

Phe Tyr Pro Lys Asp Val Leu Val Arg Trp Leu Gln Gly Ser Gln Glu
370 375 380

Leu Pro Arg Glu Asn Tyr Lys Thr Thr Ala Ser Val Leu Asp Ser Asp
385 390 395 400

Gly Ser Phe Phe Val Tyr Ser Lys Leu Thr Val Ala Ala Glu Asp Trp
405 410 415

Lys Lys Gly Asp Thr Phe Ser Cys Tyr Val Gly His Glu Ala Leu Pro
420 425 430

Leu Ala Phe Thr Gln Lys Ser Ile Ser Arg Ser Pro
435 440

<210> SEQ ID NO 68
<211> LENGTH: 444
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Gln Asp Trp Tyr Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Gly Gln Pro Arg Glu Pro Gln Val Tyr Leu Leu Pro Pro Ser Arg
            340                 345                 350

Asp Glu Leu Thr Lys Asn Gln Val Ser Leu Thr Cys Leu Ala Lys Gly
        355                 360                 365

Phe Tyr Pro Lys Asp Val Leu Val Arg Trp Leu Gln Gly Asp Gln Glu
    370                 375                 380

Leu Pro Arg Glu Asn Tyr Lys Thr Thr Ala Ser Val Leu Asp Ser Asp
385                 390                 395                 400

Gly Ser Phe Phe Val Tyr Ser Lys Leu Thr Val Ala Ala Glu Asp Trp

```
                405                 410                 415

Lys Lys Gly Asp Thr Phe Ser Cys Tyr Val Gly His Glu Ala Leu Pro
            420                 425                 430

Leu Ala Phe Thr Gln Lys Ser Ile Ser Arg Ser Pro
        435                 440


<210> SEQ ID NO 69
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Cys Cys His Pro Arg Val Phe
225                 230                 235                 240

Leu Phe Arg Pro Ala Leu Glu Asp Leu Leu Leu Gly Ser Glu Ala Asn
                245                 250                 255

Val Thr Cys Val Val Thr Gly Leu Arg Asp Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Cys Gly Cys Tyr Ser Val Val Ser Val Leu
    290                 295                 300

Thr Val Leu His Glu Asp Trp Leu Asn Gly Lys Glu Tyr Lys Cys Lys
305                 310                 315                 320
```

Val Ser Asn Lys Ala Leu Pro Ala Pro Ile Glu Lys Thr Ile Ser Lys
325 330 335

Ala Gly Gln Pro Arg Glu Pro Gln Val Tyr Leu Leu Pro Pro Ser Arg
340 345 350

Asp Glu Leu Thr Lys Asn Gln Val Ser Leu Thr Cys Leu Ala Lys Gly
355 360 365

Phe Tyr Pro Lys Asp Val Leu Val Arg Trp Leu Gln Gly Asp Gln Glu
370 375 380

Leu Pro Arg Glu Asn Tyr Lys Thr Thr Ala Ser Val Leu Asp Ser Asp
385 390 395 400

Gly Ser Phe Phe Val Tyr Ser Lys Leu Thr Val Ala Ala Glu Asp Trp
405 410 415

Lys Lys Gly Asp Thr Phe Ser Cys Tyr Val Gly His Glu Ala Leu Pro
420 425 430

Leu Ala Phe Thr Gln Lys Ser Ile Ser Arg Ser Pro
435 440

<210> SEQ ID NO 70
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Cys Cys His Pro Arg Val Phe
225 230 235 240

Leu Phe Arg Pro Ala Leu Glu Asp Leu Leu Leu Gly Ser Glu Ala Asn
245 250 255

Val Thr Cys Val Val Thr Gly Leu Arg Asp Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Cys Gly Cys Tyr Ser Val Val Ser Val Leu
290 295 300

Thr Val Leu His Glu Asp Trp Tyr Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Gly Gln Pro Arg Glu Pro Gln Val Tyr Leu Leu Pro Pro Ser Arg
340 345 350

Asp Glu Leu Thr Lys Asn Gln Val Ser Leu Thr Cys Leu Ala Lys Gly
355 360 365

Phe Tyr Pro Lys Asp Val Leu Val Arg Trp Leu Gln Gly Asp Gln Glu
370 375 380

Leu Pro Arg Glu Asn Tyr Lys Thr Thr Ala Ser Val Leu Asp Ser Asp
385 390 395 400

Gly Ser Phe Phe Val Tyr Ser Lys Leu Thr Val Ala Ala Glu Asp Trp
405 410 415

Lys Lys Gly Asp Thr Phe Ser Cys Tyr Val Gly His Glu Ala Leu Pro
420 425 430

Leu Ala Phe Thr Gln Lys Ser Ile Ser Arg Ser Pro
435 440

<210> SEQ ID NO 71
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser

-continued

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 72
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445
```

<210> SEQ ID NO 73
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400
```

-continued

```
Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445


<210> SEQ ID NO 74
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Tyr Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Ser Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445


<210> SEQ ID NO 75
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445


<210> SEQ ID NO 76
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Arg Pro Ala Leu Glu Asp Leu Leu Leu Gly
245 250 255

Ser Glu Ala Asn Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Glu Asp Trp Tyr Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Gly Gln Pro Arg Glu Pro Gln Val Tyr Leu Leu
340 345 350

Pro Pro Ser Arg Asp Glu Leu Thr Lys Asn Gln Val Ser Leu Thr Cys
355 360 365

Leu Ala Lys Gly Phe Tyr Pro Lys Asp Val Leu Val Arg Trp Leu Gln
370 375 380

Gly Ser Gln Glu Leu Pro Arg Glu Asn Tyr Lys Thr Thr Ala Ser Val
385 390 395 400

Leu Asp Ser Asp Gly Ser Phe Phe Val Tyr Ser Lys Leu Thr Val Ala
405 410 415

Ala Glu Asp Trp Lys Lys Gly Asp Thr Phe Ser Cys Tyr Val Gly His
420 425 430

Glu Ala Leu Pro Leu Ala Phe Thr Gln Lys Ser Ile Ser Arg Ser Pro
435 440 445

<210> SEQ ID NO 77
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445
```

<210> SEQ ID NO 78
<211> LENGTH: 448
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 78

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Arg Pro Ala Leu Glu Asp Leu Leu Leu Gly
245 250 255

Ser Glu Ala Asn Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Glu Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Gly Gln Pro Arg Glu Pro Gln Val Tyr Leu Leu
340 345 350

Pro Pro Ser Arg Asp Glu Leu Thr Lys Asn Gln Val Ser Leu Thr Cys
355 360 365

Leu Ala Lys Gly Phe Tyr Pro Lys Asp Val Leu Val Arg Trp Leu Gln
370 375 380

Gly Asp Gln Glu Leu Pro Arg Glu Asn Tyr Lys Thr Thr Ala Ser Val
385 390 395 400

-continued

Leu Asp Ser Asp Gly Ser Phe Phe Val Tyr Ser Lys Leu Thr Val Ala
405 410 415

Ala Glu Asp Trp Lys Lys Gly Asp Thr Phe Ser Cys Tyr Val Gly His
420 425 430

Glu Ala Leu Pro Leu Ala Phe Thr Gln Lys Ser Ile Ser Arg Ser Pro
435 440 445

<210> SEQ ID NO 79
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Arg Pro Ala Leu Glu Asp Leu Leu Leu Gly
245 250 255

Ser Glu Ala Asn Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Glu Asp Trp Tyr Asn Gly Lys Glu

-continued

```
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Tyr Val Gly His
            420                 425                 430

Glu Ala Leu Pro Leu Ala Phe Thr Gln Lys Ser Ile Ser Arg Ser Pro
        435                 440                 445


<210> SEQ ID NO 80
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

Lys Thr His Thr Cys Pro Pro Cys Pro Ala Pro Glu Leu Leu Gly Gly
225 230 235 240

Pro Ser Val Phe Leu Phe Arg Pro Ala Leu Glu Asp Leu Leu Leu Gly
245 250 255

Ser Glu Ala Asn Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Glu Asp Trp Tyr Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Gly Gln Pro Arg Glu Pro Gln Val Cys Leu Leu
340 345 350

Pro Pro Ser Arg Asp Glu Leu Thr Lys Asn Gln Val Ser Leu Ser Cys
355 360 365

Ala Ala Lys Gly Phe Tyr Pro Lys Asp Val Leu Val Arg Trp Leu Gln
370 375 380

Gly Asp Gln Glu Leu Pro Arg Glu Asn Tyr Lys Thr Thr Ala Ser Val
385 390 395 400

Leu Asp Ser Asp Gly Ser Phe Phe Val Val Ser Lys Leu Thr Val Ala
405 410 415

Ala Glu Asp Trp Lys Lys Gly Asp Thr Phe Ser Cys Met Val Gly His
420 425 430

Glu Ala Leu Pro Leu Ala Phe Thr Gln Lys Ser Ile Ser Arg Ser Pro
435 440 445

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 81

His His His His His His
1 5

<210> SEQ ID NO 82
<211> LENGTH: 448
<212> TYPE: PRT
<213> ORGANISM: Artificial sequence
<220> FEATURE:
<223> OTHER INFORMATION: Description of Artificial Sequence: Synthetic
polypeptide

<400> SEQUENCE: 82

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Ala Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

<210> SEQ ID NO 83
<211> LENGTH: 448
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Asn Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Glu Asp Trp Tyr Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400
```

```
Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

<210> SEQ ID NO 84
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Arg Pro Ala Leu Glu Asp Leu Leu Leu Gly
                245                 250                 255

Ser Glu Ala Ala Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Glu Asp Trp Tyr Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Gly Gln Pro Arg Glu Pro Gln Val Tyr Leu Leu
            340                 345                 350

Pro Pro Ser Arg Asp Glu Leu Thr Lys Asn Gln Val Ser Leu Thr Cys
        355                 360                 365

Leu Ala Lys Gly Phe Tyr Pro Lys Asp Val Leu Val Arg Trp Leu Gln
    370                 375                 380

Gly Asp Gln Glu Leu Pro Arg Glu Asn Tyr Lys Thr Thr Ala Ser Val
385                 390                 395                 400

Leu Asp Ser Asp Gly Ser Phe Phe Val Tyr Ser Lys Leu Thr Val Ala
                405                 410                 415

Ala Glu Asp Trp Lys Lys Gly Asp Thr Phe Ser Cys Met Val Gly His
            420                 425                 430

Glu Ala Leu Pro Leu Ala Phe Thr Gln Lys Ser Ile Ser Arg Ser Pro
        435                 440                 445
```

IMMUNOGLOBULIN VARIANTS

CROSS REFERENCE TO RELATED APPLICATIONS

This application is a 371 U.S. national phase application of the International Application No. PCT/IB2021/053585, filed on Apr. 29, 2021, which claims priority to, and the benefit of, U.S. Patent Application No. 63/018,698, filed on May 1, 2020, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 19, 2021 is named PAT058743-WO-PCT_SL.txt and is 316 Kbytes in size.

FIELD OF THE INVENTION

The invention relates to Fc variant polypeptides and antibodies with optimized properties to promote the recruitment of neutrophils and engineering methods for their preparation. The Fc variant polypeptides and antibodies can be useful in the treatment of tumors, particularly solid tumors.

BACKGROUND OF THE INVENTION

At present, all clinically approved antibodies comprise the immunoglobulin IgG isotype. Antibody-dependent cell-mediated cytotoxicity (ADCC) is a key mechanism for tumor cell killing mediated by IgG antibodies that recognize and bind to Fc gamma receptors (FcγR). However, in patients with a high tumor burden, relapses can occur and IgG antibody therapeutics may lose efficacy owing to the immunosuppressive environment found in tumors. In the tumor microenvironment, FcγR-bearing effector cells such as macrophages and natural killer cells can be rendered lytically incompetent by immunosuppressive factors such as TGFβ. IgA represents an alternative isotype for antibody therapy by engaging Fc alpha receptors (FcαRI) expressed by myeloid effector cells, such as neutrophils and tumor-resident myeloid-derived suppressor cells (MDSC). IgA is the second most abundant immunoglobulin in human serum after IgG; both monomeric IgA allotypes (IgA1 and IgA2) comprise up to 25% of human serum immunoglobulins. In the past, neutrophils were generally not considered as potential effector cells. However, neutrophils are the most abundant population of circulating white blood cells and have also been shown to infiltrate solid tumors (Gregory & Houghton (2011) Cancer Res., 71: 2411-16; Vogt Sionov et al., (2015) Cancer Microenviron., 8(3): 125-58; Uribe-Querol & Rosales (2015) J. Immunol. Res., Article ID: 983698; Rosales (2018) Front Physiol., 9: 113). MDSCs are also derived from myeloid lineages and are one of the most immunosuppressive cell types. IgA antibodies have been shown to effectively kill tumor cells by recruitment of neutrophils and thereby enhancing ADCC. Unfortunately, the use of IgA antibodies as therapeutics is hampered by several liabilities and limitations such as low expression yields and expensive purification schemes. In addition, the production suffers from heterogeneous glycosylation. IgA has multiple glycosylation sites that can be susceptible to glycan heterogeneity. Transient expression levels for monomeric IgA have been reported for human IgA1 at 30-70 μg/L (Lombana et al (2019) MABS, 11: 1122-38; Meyer et al (2016) MABS, 8: 87-98).

Therefore, there remains a need for IgA antibodies that can be developed as therapeutic antibodies. IgA antibodies with improved potency could provide a viable alternative to IgG therapeutic antibodies with the advantage of effective tumor cell killing by the recruitment of neutrophils, MDSC and enhanced ADCC.

SUMMARY OF THE INVENTION

The present invention provides Fc variants of a parent Fc polypeptide of the IgA isotype, that have improved binding properties to FcαRI and can be used to recruit and activate neutrophils. The Fc variant of the present disclosure comprises amino modifications, which can comprise independently or in combination amino acid insertion(s), amino acid deletion(s) and/or amino acid substitutions.

In one aspect the present disclosure provides an Fc variant of a parent Fc polypeptide, wherein the Fc variant exhibits altered binding to a FcαR or altered antibody dependent cell-mediated cytotoxicity (ADCC) as compared to the parent Fc polypeptide, wherein the Fc variant comprises at least one amino acid modification in the Fc region of the parent Fc polypeptide. In one embodiment, the amino acid modification is at a position selected from the group consisting of: CH2.10, CH2.89, CH2.91, CH2.94, CH2.97, CH2.99, CH3.45, CH3.105, CH3.109, CH3.118 and CH3.124, wherein the numbering of the amino acid modification is according to IMGT numbering for C-domain. In a preferred embodiment, the Fc variant comprises at least one amino acid modification in the Fc region of the parent Fc polypeptide, wherein the amino acid modification is selected from the group consisting of: A_CH2.10_S, L_CH2.89_I, G_CH2.91_Q, G_CH2.91_V, Q_CH2.94_E, N_CH2.97_H, N_CH2.97_Y, G_CH2.99_W, S_CH3.45_D, M_CH3.105_Y, E_CH3.109_D, Q_CH3.118_Y and L_CH3.124_F, wherein the numbering of the amino acid modification is according to IMGT numbering for C-domain. In a further embodiment, the present disclosure provides an Fc variant comprising at least one amino acid modification in the Fc region, wherein the amino acid modification is selected from the group consisting of: Q_CH2.94_E, N_CH2.97Y, S_CH3.45_D, M_CH3.105_Y, Q_CH3.118_Y, Q_CH2.94_E/N_CH2.97_Y, Q_CH2.94_E/S_CH3.45_D, Q_CH2.94_E/M_CH3.105_Y, N_CH2.97_Y/S_CH3.45_D, N_CH2.97_Y/M_CH3.105_Y, S_CH3.45_D/M_CH3.105_Y, M_CH3.105_Y/Q_CH3.118_Y, Q_CH2.94_E/N_CH2.97_Y/M_CH3.105_Y, N_CH2.97_Y/S_CH3.45_D/M_CH3.105_Y, Q_CH2.94_E/S_CH3.45_D/M_CH3.105_Y, M_CH3.105_Y/Q_CH3.118_Y/S_CH3.45_D, Q_CH2.94_E/N_CH2.97_Y/S_CH3.45_D, Q_CH2.94_E/N_CH2.97_Y/S_CH3.45_D/M_CH3.105_Y, Q_CH2.94_E/N_CH2.97_Y/M_CH3.105_Y/Q_CH3.118_Y, Q_CH2.94_E/N_CH2.97_Y/S_CH3.45_D/M_CH3.105_Y/Q_CH3.118_Y, A_CH2.10_S, L_CH2.89_, G_CH2.91_V, N_CH2.97_H, G_CH2.99_W, E_CH3.109_D, L_CH3.124_F, L_CH2.89_I/G_CH2.91_V/Q_CH2.94_E/N_CH2.97_Y/G_CH2.99_W, wherein the numbering of the amino acid modification is according to IMGT numbering for C-domain.

In one embodiment, the present disclosure provides an Fc variant of a parent Fc polypeptide comprising an amino acid modification at positions CH2.94, CH2.97, CH3.45, CH3.105 and CH3.118. In one embodiment, the Fc variant of a parent Fc polypeptide comprises the amino acid substitutions Glu at position CH2.94, Tyr at position CH2.97, Asp at position CH3.45, Tyr at position CH3.105 or Tyr at position CH3.118. In a preferred embodiment, the Fc variant of a parent Fc polypeptide comprises the amino acid substitutions Q_CH2.94_E, L_CH2.97_Y, S_CH3.45_D, M_CH3.105_Y, and Q_CH3.118_Y.

In one embodiment, the present disclosure provides an Fc variant of a parent Fc polypeptide, wherein the parent Fc polypeptide is comprised within human IgA1, or wherein the parent Fc polypeptide is comprised within human IgA2.

In one embodiment of the present disclosure, the Fc variant exhibits altered binding to a FcαR compared to the parent Fc polypeptide. Provided herein is an Fc variant of a parent Fc polypeptide wherein the Fc variant has increased affinity to human FcαRI of at least 50-fold relative to the parent Fc polypeptide as measured by surface plasmon resonance (SPR). In one embodiment, the present disclosure provides an Fc variant of a parent Fc polypeptide wherein the Fc variant has an increased affinity to human FcαRI of at least about 50, about 100, about 150, about 200, about 250, about 300-fold relative to the parent Fc polypeptide as measured by surface plasmon resonance. In one embodiment, the present disclosure provides an Fc variant of a parent Fc polypeptide wherein the Fc variant has an increased affinity to human FcαRI of at least about 300-fold relative to the parent Fc polypeptide as measured by SPR.

In one embodiment of the present disclosure, the Fc variant exhibits altered ADCC as compared to the parent Fc polypeptide. Provided herein is an Fc variant of a parent Fc polypeptide wherein the Fc variant increases antibody-dependent cell-mediated cytotoxicity (ADCC) by at least about 5-fold relative to the parent Fc polypeptide as measured in a MDA-MB-453 cell-killing assay. In one embodiment, the present disclosure provides an Fc variant of a parent Fc polypeptide wherein the Fc variant has an increased efficacy of at least about 2-fold in a Calu-3 cell-killing assay relative to the parent Fc polypeptide.

In another aspect, the present disclosure provides an IgA antibody comprising a variant Fc polypeptide, wherein the antibody has increased FcαR affinity, or increased ADCC, relative to an IgA antibody comprising a wild-type Fc polypeptide. In one embodiment, the present disclosure provides an IgA antibody comprising an amino acid modification at a position selected from the group consisting of: CH2.10, CH2.89, CH2.91, CH2.94, CH2.97, CH2.99, CH3.45, CH3.105, CH3.109, CH3.118 and CH3.124, wherein the numbering of the amino acid modification is according to IMGT numbering for C-domain. In a preferred embodiment, the present disclosure provides an IgA antibody comprising an amino acid modification, wherein the amino acid modification is selected from the group consisting of: A_CH2.10_S, L_CH2.89_I, G_CH2.91_Q, G_CH2.91_V, Q_CH2.94_E, N_CH2.97_H, N_CH2.97_Y, G_CH2.99_W, S_CH3.45_D, M_CH3.105_Y, E_CH3.109_D, Q_CH3.118_Y and L_CH3.124_F, wherein the numbering of the amino acid modification is according to IMGT numbering for C-domain.

In a further embodiment, the present disclosure provides an IgA antibody comprising an amino acid modification, wherein the amino acid modification is selected from the group consisting of: Q_CH2.94_E, N_CH2.97Y, S_CH3.45_D, M_CH3.105_Y, Q_CH3.118_Y, Q_CH2.94_E/N_CH2.97_Y, Q_CH2.94_E/S_CH3.45_D, Q_CH2.94_E/M_CH3.105_Y, N_CH2.97_Y/S_CH3.45_D, N_CH2.97_Y/M_CH3.105_Y, S_CH3.45_D/M_CH3.105_Y, M_CH3.105_Y/Q_CH3.118_Y, Q_CH2.94_E/N_CH2.97_Y/M_CH3.105_Y, N_CH2.97_Y/S_CH3.45_D/M_CH3.105_Y, Q_CH2.94_E/S_CH3.45_D/M_CH3.105_Y, M_CH3.105_Y/Q_CH3.118_Y/S_CH3.45_D, Q_CH2.94_E/N_CH2.97_Y/S_CH3.45_D, Q_CH2.94_E/N_CH2.97_Y/S_CH3.45_D/M_CH3.105_Y, Q_CH2.94_E/N_CH2.97_Y/M_CH3.105_Y/Q_CH3.118_Y, Q_CH2.94_E/N_CH2.97_Y/S_CH3.45_D/M_CH3.105_Y/Q_CH3.118_Y, A_CH2.10_S, L_CH2.89_I, G_CH2.91_V, N_CH2.97_H, G_CH2.99_W, E_CH3.109_D, L_CH3.124_F, L_CH2.89_I/G_CH2.91_V/Q_CH2.94_E/N_CH2.97_Y/G_CH2.99_W, wherein the numbering of the amino acid modification is according to IMGT numbering for C-domain.

In one embodiment, the present disclosure provides an IgA antibody comprising an amino acid modification at positions CH2.94, CH2.97, CH3.45, CH3.105 and CH3.118. In one embodiment, the IgA antibody comprises the amino acid substitutions Glu at position CH2.94, Tyr at position CH2.97, Asp at position CH3.45, Tyr at position CH3.105 or Tyr at position CH3.118. In a preferred embodiment, the IgA antibody comprises the amino acid substitutions Q_CH2.94_E, L_CH2.97_Y, S_CH3.45_D, M_CH3.105_Y, Q and CH3.118_Y.

In one embodiment, the present disclosure provides an IgA antibody comprising a variant Fc polypeptide, wherein the antibody is a human IgA1 or IgA2 antibody.

The present disclosure provides isolated nucleic acids encoding the Fc variants described herein. The present disclosure provides vectors comprising the nucleic acids, optionally, operably linked to control sequences. The present disclosure provides host cells containing the vectors, and methods for producing and optionally recovering the Fc variants. The present disclosure provides compositions comprising IgA antibodies that comprise the Fc variants described herein, and a physiologically or pharmaceutically acceptable carrier or diluent.

The present disclosure contemplates therapeutic and diagnostic uses for IgA antibodies that comprise the Fc variants disclosed herein. The Fc variants disclosed herein could also be used for the construction of other binding molecules such as bi-specific and multi-specific antibodies. The IgA antibodies described in the present disclosure may be used to treat a variety of indications, including but not limited to proliferative diseases such as cancers.

BRIEF DESCRIPTION OF THE FIGURES

FIGS. 5A and 5B show the Fc variants with SEQ ID NOs: 7-8 (■) and 80-8 (▲), compared to IgA2 (SEQ ID NO: 3 (●); FIG. 5*a*) and IgG1 (SEQ ID NO: 1 (●); FIG. 5*b*), respectively. FIGS. 5C and 5D show the Fc variants with SEQ ID NOs: 7-9 (▼) and 80-9 (♦) compared to IgA2 (SEQ ID NO: 2 (●); FIG. 5*c*) and IgG1 (SEQ ID NO: 1 (●); FIG. 5*d*), respectively.

DETAILED DESCRIPTION

Figure 1:
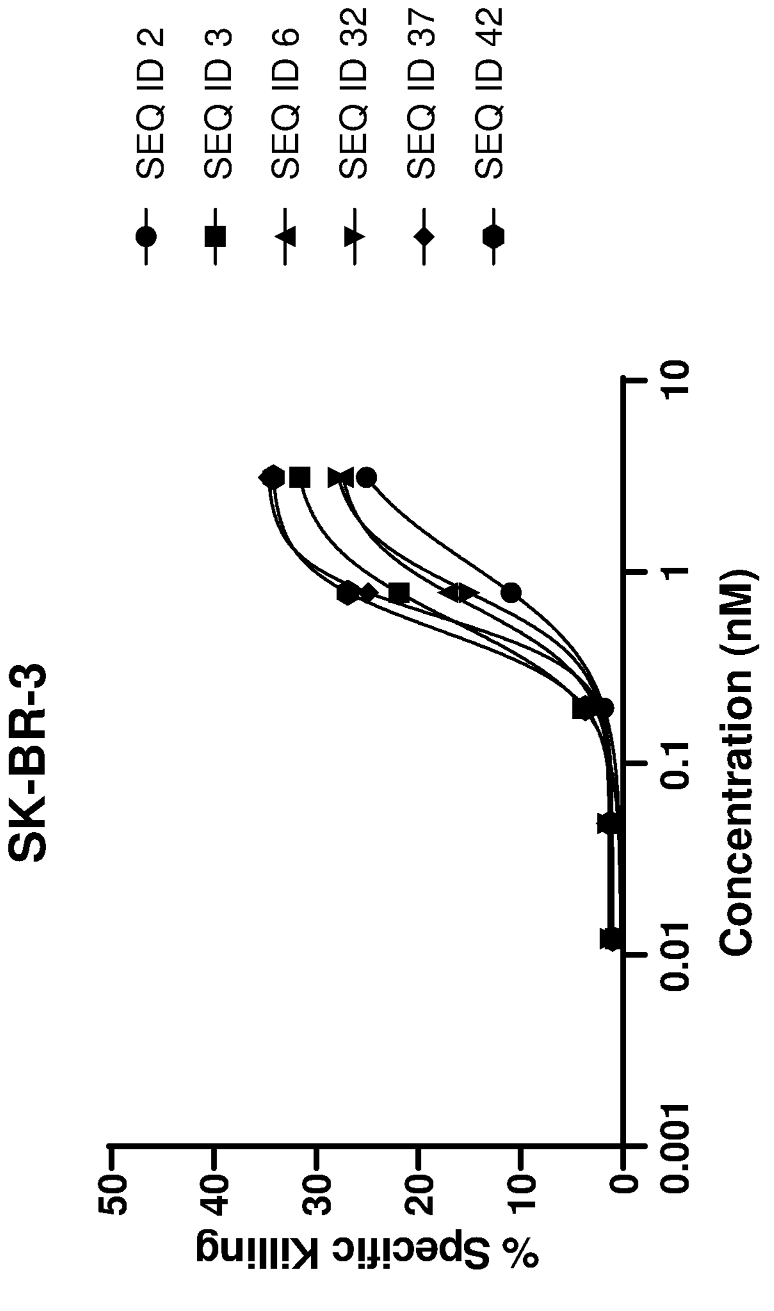
FIG. 1 shows PMN cytotoxicity of increasing concentrations of the Fc variants: SEQ ID NOs: 3 (■), 6 (▲), 32 (▼), 37 (♦) and 42 (•), and parental IgA2 (SEQ ID NO: 2 (●)) on SK-BR-3 cells, in an ADCC assay as described in Example 4. The efficacy (Emax %) for each Fc variant was as follows: SEQ ID NO: 2: 25%, SEQ ID NO: 3: 32%, SEQ ID NO: 6: 27%, SEQ ID NO: 32: 28%, SEQ ID NO: 37: 35% and SEQ ID NO: 42: 34%.
Figure 2:
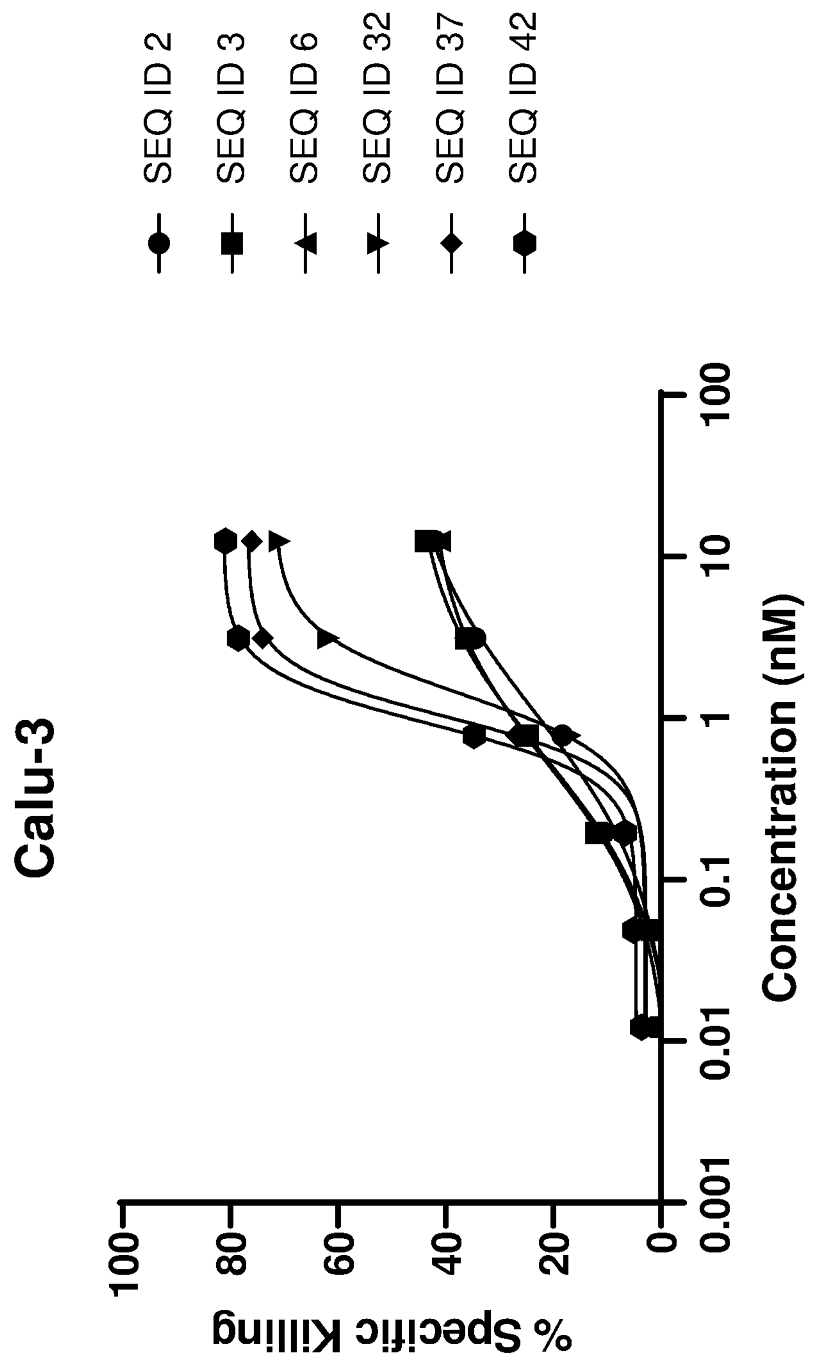
FIG. 2 shows PMN cytotoxicity of increasing concentrations of the Fc variants: SEQ ID NOs: 3 (■), 6 (▲), 32 (▼), 37 (♦) and 42 (•), and parental IgA2 (SEQ ID NO: 2 (●)) on Calu-3 cells, in an ADCC assay as described in Example 4. The efficacy (Emax %) for each Fc variant was as follows: SEQ ID NO: 2:42%, SEQ ID NO: 3: 44%, SEQ ID NO: 6:41%, SEQ ID NO: 32: 71%, SEQ ID NO: 37: 76% and SEQ ID NO: 42: 81%.

Disclosed herein are Fc variants of the IgA immunoglobulin having optimized properties, as well as antibodies comprising these Fc variants. These optimized properties include enhanced binding to FcαR and altered antibody-dependent cell-mediated cytotoxicity (ADCC), relative to a parent IgA Fc polypeptide.

Definitions

In order that the present disclosure may be more readily understood, certain terms are specifically defined throughout the detailed description. Unless defined otherwise, all technical and scientific terms used herein have the same meaning as commonly understood by those of ordinary skill in the art to which this disclosure pertains.

In all cases where the term "comprise", "comprises", "comprising" or the like are used in reference to a sequence (e.g., an amino acid sequence), it shall be understood that said sequence may also be limited by the term "consist", "consists", "consisting" or the like. As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an Fc variant of the present disclosure. In some aspects, the phrase "consisting essentially of" expressly excludes the inclusion of one or more additional active agents other than an Fc variant of the present disclosure and a second co-administered agent.

As used herein, the term "antibody" refers to a polypeptide of the immunoglobulin family that is capable of binding a corresponding antigen non-covalently, reversibly, and in a specific manner. The basic functional unit of each antibody is an immunoglobulin monomer containing only one Ig unit, defined herein as an "Ig monomer". Secreted antibodies can also be dimeric with two Ig units (e.g. IgA), tetrameric with four Ig units or pentameric with five Ig units (e.g. mammalian IgM). The term "antibody" includes, for example, a monoclonal antibody (including a full length antibody which has an immunoglobulin Fc region). The Ig monomer is a Y-shaped molecule that consists of four polypeptide chains; two identical heavy chains and two identical light chains connected by disulfide bonds (Woof & Burton (2004) Nature Reviews Immunology, 4(2): 89-99). Each chain comprises a number of structural domains containing about 70-110 amino acids that are classified into two categories: variable or constant, according to their size and function. The heavy chain comprises one variable domain (abbreviated as VH) and three constant domains (abbreviated as CH1, CH2 and CH3). Each light chain comprises one variable domain (abbreviated as VL) and one constant domain (abbreviated as CL). Immunoglobulin domains have a characteristic immunoglobulin fold in which two beta sheets create a 'sandwich' shape, held together by interactions between conserved cysteine residues and other charged amino acids. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3 and FR4. The variable regions of the heavy and light chains contain an antigen binding domain or antigen binding site that interacts with an antigen.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

The term "monospecific molecule," as used herein, refers to a molecule that binds to one epitope on a target antigen. In some embodiments, a mono-specific molecule of the present disclosure is a monospecific antibody-like molecule. In some embodiments, a mono-specific molecule of the present disclosure is a monospecific antibody. The term "bispecific molecule" refers to a multi-specific binding molecule that binds to two different antigens. In some embodiments, a bispecific molecule of the present disclosure is a bispecific antibody-like molecule. The term "multi-specific binding molecule" as used herein refers to a molecule that binds to two or more different antigens. Recognition of each antigen is generally accomplished via an "antigen-binding domain" In some embodiments, a multi-specific binding molecule of the present disclosure is a multi-specific antibody-like molecule, such as a bispecific antibody-like molecule.

The term "antigen-binding site" refers to the part of an antibody that comprises determinants that form an interface that binds to the antigen, or an epitope thereof. The term "antigen binding site" may be used interchangeably with the term "antigen binding domain". With respect to proteins (or protein mimetics), the antigen-binding site typically includes one or more loops (of at least four amino acids or amino acid mimics) that form an interface that binds to the antigen polypeptide. Typically, the antigen-binding site of an antibody molecule includes at least one or two CDRs and/or hypervariable loops, or more typically at least three, four, five or six CDRs and/or hypervariable loops.

"Complementarity-determining regions" ("CDRs") as used herein, refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting in total about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, (2000) Immunology, 4th ed., Chapter 4. W.H. Freeman & Co., New York). The positions of the CDRs and framework regions can be determined using various well-known definitions in the art, e.g., Kabat, Chothia, IMGT, AbM, and combined definitions (see, e.g., Johnson et al., (2001) Nucleic Acids Res., 29:205-206; Chothia & Lesk, (1987) J. Mol. Biol., 196:901-917; Chothia et al., (1989) Nature, 342:877-883; Chothia et al., (1992) J. Mol. Biol., 227:799-817; Lefranc, M. P., (2001) Nucleic Acids Res., 29:207-209; Al-Lazikani et al., (1997) J. Mol. Biol., 273:927-748 and Kabat et al., (1991) Sequences of proteins of immunological interest. 5th Edition—US DHHS, NIH publication no 91-3242, pp 662, 680, 689). Definitions of antigen combining sites are also described in the following: Ruiz et al., (2000) Nucleic Acids Res., 28:219-221; MacCallum et al., (1996) J. Mol. Biol., 262:732-745; and Martin et al., (1989) Proc. Natl. Acad. Sci. USA, 86:9268-9272; Martin et al., (1991) Methods Enzymol., 203:121-153; and Rees et al., (1996) In Sternberg M. J. E. (ed.), Protein Structure Prediction, Oxford University Press, Oxford, 141-172. In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align. IMGT tools are available at world wide web (www).imgt.org.

In an embodiment, an antibody comprises an "antigen-binding fragment" of an antibody. Examples of such fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al., (1988) Science 242:423-426; and Huston et al., (1988) PNAS USA 85:5879-5883); (viii) a single domain antibody; (ix) diabodies (Dab) (bivalent and bispecific), and (x) chimeric (e.g., humanized) antibodies which may be produced by the modification of whole antibodies or those synthesized de novo using recombinant DNA technologies. These functional antibody fragments retain the ability to selectively bind with their respective antigen or receptor. These antibody fragments are obtained using conventional techniques known to those with skill in the art, and the fragments are screened for utility in the same manner as are intact antibodies.

In mammals there are two types of immunoglobulin light chain, which are called lambda (λ) and kappa (κ). Each antibody contains two light chains that are always identical; only one type of light chain, κ or λ, is present per antibody in mammals. The approximate length of a light chain is 211 to 217 amino acids and each light chain has two domains, one constant domain and one variable domain.

There are five types of mammalian Ig heavy chains denoted α, δ, ε, γ, and μ and the type of heavy chain present in the antibody defines the class or isotype of the antibody: IgM, IgG, IgA, IgD, IgE, respectively. The heavy chains vary in physiochemical, structural, and immunological properties but each heavy chain has two domains, a variable domain and a constant domain. The variable domain comprises a single Ig domain (approximately 110 amino acids long) and determines antibody binding specificity. The constant domain is identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains (Woof & Burton, supra). The term "immunoglobulin" (Ig) is used interchangeably with the term "antibody" herein.

IgG is the most abundant antibody isotype in the blood (plasma), accounting for 70-75% of human immunoglobulins. IgG detoxifies harmful substances and is important in the recognition of antigen-antibody complexes by leukocytes and macrophages. IgG is further divided into 4 subclasses in humans: IgG1, IgG2, IgG3 and IgG4. IgM usually circulates in the blood, accounting for about 10% of human immunoglobulins. IgM has a pentameric structure in which five basic Y-shaped molecules are linked together. B cells produce IgM first in response to microbial infection/antigen invasion. Although IgM has a lower affinity for antigens than IgG, it has higher avidity for antigens because of its pentameric/hexameric structure. IgM, by binding to the cell surface receptor, also activates cell signaling pathways. IgA is abundant in serum, nasal mucus, saliva, breast milk, and intestinal fluid, accounting for 25% of human immunoglobulins. IgA forms dimers (i.e., two IgA monomers joined together). IgA in breast milk protects the gastrointestinal tract of neonates from pathogens. IgA is divided into 2 subclasses: IgA1 and IgA2. IgD accounts for less than 1% of human immunoglobulins and may be involved in the induction of antibody production in B cells, but its exact function remains unknown. IgE is present in minute amounts, accounting for no more than 0.001% of human immunoglobulins. Its original role is to protect against parasites. In regions where parasitic infection is rare, IgE is primarily involved in allergy.

Immune cell activity is modulated by a region of an antibody known as the fragment crystallisable region or "Fc region". The Fc region is composed of two identical polypeptide chains (each referred to herein as an "Fc domain"), which in IgG and IgA comprises the CH2 and CH3 constant domains of the heavy chain. IgM and IgE Fc regions contain three heavy chain constant domains (CH domains 2-4) in each polypeptide chain. The amino acid residues in the CH2 and CH3 domains can be numbered according to the EU numbering system (Edelman et al., (1969) PNAS. USA, 63, 78-85), "Kabat" numbering (Kabat et al., supra) or alternatively using the IMGT numbering for C domains. IMGT tools are available at world wide web (www).imgt.org.

The Fc region binds to cell surface receptors, "Fc receptors" and complement proteins mediating physiological effects of antibodies. Fc receptors are found on may cells of the immune system including: B lymphocytes, follicular dendritic cells, natural killer cells, macrophages, neutrophils, eosinophils, basophils, human platelets and mast cells. Binding of antibody Fc region to Fc receptors stimulates phagocytic or cytotoxic cells to destroy microbes, or infected cells by the mechanism of antibody-dependent cell-mediated cytotoxicity (ADCC). There are several different types of Fc receptors (FcR), which are classified based on the type of antibody that they recognize. For example, those that bind IgG are called Fc-gamma receptors (FcγR), those that bind IgA are called Fc-alpha receptors (FcαRI) and those that bind IgE are called Fc-epsilon receptors (FcεR). The classes of FcRs are also distinguished by the cells that express them (macrophages, granulocytes, natural killer cells, T and B cells) and the signaling properties of each receptor (Owen J et al., (2009) Immunology (7th ed.). New York: W.H. Freeman and Company. p 423). The FcαRI is also known as CD89 and its principal antibody ligand is IgA. This receptor has a low affinity for IgA (Kd>$10^{-6}$ M) and is found on monocytes, macrophages, neutrophils and eosinophils. The binding of IgA to FcαRI primarily leads to phagocytosis and the induction of microbe killing.

In an embodiment, an antibody comprises a full-length antibody, or a full-length immunoglobulin chain. In an embodiment, an antibody comprises an antigen binding or functional fragment of a full-length antibody, or a full-length immunoglobulin chain. The preparation of an antibody can be monoclonal or polyclonal. An antibody can also be a human, humanized, CDR-grafted, or in vitro generated antibody.

In one embodiment, the antibody or immunoglobulin can be recombinantly produced, e.g., produced by phage display or by combinatorial methods. Phage display and combinatorial methods for generating antibodies are known in the art (as described in, e.g., Ladner et al., U.S. Pat. No. 5,223,409; Kang et al., WO 92/18619; Dower et al., WO 91/17271; Winter et al., WO 92/20791; Markland et al., WO 92/15679; Breitling et al., WO 93/01288; McCafferty et al., WO 92/01047; Garrard et al., WO 92/09690; Ladner et al., WO 90/02809; Fuchs et al., (1991) Bio/Technology, 9:1370-1372; Hay et al., (1992) Hum Antibody Hybridomas, 3:81-85; Huse et al., (1989) Science 246:1275-1281; Griffths et al., (1993) EMBO J., 12:725-734; Hawkins et al., (1992) J Mol Biol., 226:889-896; Clackson et al., (1991) Nature, 352:624-628; Gram et al., (1992) PNAS, 89:3576-3580; Garrard et al., (1991) Bio/Technology, 9:1373-1377; Hoogenboom et al., (1991) Nuc Acid Res., 19:4133-4137; and Barbas et al., (1991) PNAS, 88:7978-7982; the contents of all of which are incorporated by reference herein).

In one embodiment, the antibody or immunoglobulin is a fully human antibody (e.g., an antibody made in a mouse which has been genetically engineered to produce an antibody from a human immunoglobulin sequence or an antibody isolated from a human), or a non-human antibody, e.g., a rodent (mouse or rat), goat, primate (e.g., monkey), camel antibody. Human monoclonal antibodies can be generated using transgenic mice carrying the human immunoglobulin genes rather than the mouse system. Splenocytes from these transgenic mice immunized with the antigen of interest are used to produce hybridomas that secrete human monoclonal antibodies with specific affinities for epitopes from a human protein (see, e.g., Wood et al., WO 91/00906, Kucherlapati et al., WO 91/10741; Lonberg et al., WO 92/03918; Kay et al., WO 92/03917; Lonberg et al., (1994) Nature 368:856-859; Green et al., (1994) Nature Genet. 7:13-21; Morrison et al., (1994) PNAS USA 81:6851-6855; Bruggeman et al., (1993) Year Immunol 7:33-40; Tuaillon et al., (1993) PNAS 90:3720-3724; Bruggeman et al., (1991) Eur J Immunol 21:1323-1326).

An antibody or immunoglobulin can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention. Chimeric antibodies can be produced by recombinant DNA techniques known in the art (see Robinson et al., WO 87/002671; Akira et al., EP184187A1; Taniguchi, EP171496A1; Morrison et al., EP173494A1; Neuberger et al., WO 86/01533; Cabilly et al., U.S. Pat. No. 4,816,567; Cabilly et al., EP125023A1; Better et al., (1988) Science 240:1041-1043; Liu et al., (1987) PNAS 84:3439-3443; Liu et al., (1987), J. Immunol. 139:3521-3526; Sun et al., (1987) PNAS 84:214-218; Nishimura et al., (1987), Canc. Res. 47:999-1005; Wood et al., (1985) Nature 314:446-449; and Shaw et al., (1988), J. Natl Cancer Inst. 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to the target antigen. Preferably, the donor will be a rodent antibody, e.g., a rat or mouse antibody, and the recipient will be a human framework or a human consensus framework. Typically, the immunoglobulin providing the CDRs is referred to as the 'donor' and the immunoglobulin providing the framework is referred to as the 'acceptor'. In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identity thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987)). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, (1985), Science 229:1202-1207; Oi et al., (1986), BioTechniques 4:214, and Queen et al., U.S. Pat. Nos. 5,585,089, 5,693,761 and 5,693,762, the contents of all of which are hereby incorporated by reference). Humanized or CDR-grafted antibodies can be produced by CDR-grafting or CDR substitution, wherein one, two, or all CDRs of an immunoglobulin chain can be replaced. See, e.g., U.S. Pat. No. 5,225,539; Jones et al., (1986) Nature 321:552-525; Verhoeyan et al., (1988) Science 239:1534; Beidler et al., (1988) J. Immunol. 141:4053-4060 and Winter U.S. Pat. No. 5,225,539, the contents of all of which are hereby expressly incorporated by reference. Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, the contents of which are hereby incorporated by reference. Other techniques for humanizing antibodies are described in Padlan et al., EP 519596 A1.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP388151A1, U.S. Pat. Nos. 5,624,821 and 5,648,260).

By "position" as used herein is meant a location of an amino acid in the sequence of a protein. Positions may be numbered sequentially, or according to an established format, for example the EU index as in Kabat or IMGT numbering (www.imgt.org). When using the IMGT numbering for example, glutamine 94 (also referred to as Gln94, also referred to as Q94) is also given a position location in the Fc region to denote if it is found in the CH2 or CH3 domain. For example, QCH2.94, SCH3.45 denotes a glutamine at position 94 in the CH2 domain and serine at position 45 in the CH3 domain, in the human antibody IgA1.

By "residue" as used herein is meant a position in a protein and its associated amino acid identity. For example, Glutamine 94 (also referred to as Gln94, also referred to as Q94) is a residue in the human antibody IgA1.

A "modification" or "mutation" of an amino acid residue(s)/position(s), as used herein, refers to a change of a primary amino acid sequence as compared to a starting amino acid sequence, wherein the change results from a sequence alteration involving said one or more amino acid residue/positions. For example, typical modifications include substitution of the one or more residue(s) (or at said position(s)) with another amino acid(s) (e.g., a conservative or non-conservative substitution), insertion of one or more amino acids adjacent to said one or more residue(s)/position(s), and deletion of said one or more residue(s)/position(s), inversion of said one or more residue(s)/position(s), and duplication of said one or more residue(s)/position(s). An amino acid 'substitution' or variation thereof, refers to the replacement of an one or more existing amino acid residue(s) in a predetermined (starting) amino acid sequence with a one or more different amino acid residue(s). Generally and preferably, the modification results in alteration in at least one physicobiochemical activity of the variant polypeptide compared to a polypeptide comprising the starting or parental (or "wild-type") amino acid sequence. For example, in the case of an antibody or an Fc variant, a physicobiochemical activity that is altered can be binding affinity, binding capability and/or binding effect upon a target molecule.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g., from about one to about ten amino acid modifications, and preferably from about one to about five amino acid modifications compared to the parent. The variant polypeptide sequence as described herein will possess at least about 80% homology with a parent polypeptide sequence, preferably at least about 90% homology, more preferably at least about 95% homology. In one embodiment, the variant polypeptide sequence as described herein will possess at least about 85% homology with a parent IgA CH2 polypeptide sequence, preferably at least about 90% homology, more preferably at least about 95% homology. In one embodiment, the variant polypeptide sequence as described herein will possess at least about 90% homology with a parent IgA CH3 polypeptide sequence, preferably at least about 95% homology, more preferably at least about 97% homology. In a preferred embodiment, the variant polypeptide sequence as described herein will possess at least about 85% homology, preferably at least about 90% homology, more preferably at least about 95% homology with a parent IgA CH2 polypeptide sequence, and possess at least about 90% homology, preferably at least about 95% homology, more preferably at least about 97% homology with a parent IgA CH3 polypeptide sequence. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. The term "parent Fc polypeptide" as used herein means the starting Fc polypeptide to which the amino acid modification(s) is made. The parent Fc polypeptide can be a wild-type Fc polypeptide or a Fc polypeptide which is an allelic variation of a wild-type Fc polypeptide. The parent Fc polypeptide can also be an Fc polypeptide to which amino acid modifications have already been made. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgA variant" or "variant IgA" as used herein is meant an antibody that differs from a parent IgA by virtue of at least one amino acid modification. The parent IgA can be of the isotype IgA1 or IgA2. By "immunoglobulin variant" or "variant immunoglobulin" as used herein is meant an immunoglobulin sequence that differs from that of a parent immunoglobulin sequence by virtue of at least one amino acid modification.

By "wild-type" or "WT" herein is meant an amino acid sequence or a nucleotide sequence that is found in nature, including allelic variations. A WT protein, polypeptide, antibody, immunoglobulin, IgA, etc. has an amino acid sequence or a nucleotide sequence that has not been intentionally modified.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine (K), arginine (R), histidine (H)), acidic side chains (e.g., aspartic acid (D), glutamic acid (E)), uncharged polar side chains (e.g., glycine (G), asparagine (N), glutamine (Q), serine (S), threonine (T), tyrosine (Y), cysteine (C)), nonpolar side chains (e.g., alanine (A), valine (V), leucine (L), isoleucine (I), proline (P), phenylalanine (F), methionine (M), tryptophan (W)), beta-branched side chains (e.g., threonine (T), valine (V), isoleucine (I)) and aromatic side chains (e.g., tyrosine (Y), phenylalanine (F), tryptophan (W), histidine (H)).

The terms "percent identical" or "percent identity" in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. A "percentage identity" or "percentage sequence identity" of the present disclosure can be calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" as used herein includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known in the art. Optimal alignment of sequences for comparison can be conducted, e.g., by the local homology algorithm of Smith & Waterman (1970) Adv. Appl. Math. 2:482c, by the homology alignment algorithm of Needleman & Wunsch (1970) J. Mol. Biol., 48: 443, by the search for similarity method of Pearson & Lipman (1988) PNAS USA, 85: 2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25: 3389-3402; and Altschul et al., (1990) J. Mol. Biol., 215: 403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul et al., (1990) supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, (1989) PNAS. USA, 89: 10915) alignments (B) of 50, expectation (E) of 10, M=5, N=−4, and a comparison of both strands.

The BLAST algorithm also performs a statistical analysis of the similarity between two sequences (see, e.g., Karlin & Altschul (1993) PNAS. USA, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci. 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman & Wunsch supra algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res., 19: 5081; Ohtsuka et al., (1985) J Biol Chem., 260: 2605-2608; and Rossolini et al., (1994) Mol Cell Probes, 8: 91-98). As used herein, the term, "optimized nucleotide sequence" means that the nucleotide sequence has been altered to encode an amino acid sequence using codons that are preferred in the production cell, in this case a Chinese Hamster Ovary cell (CHO). The optimized nucleotide sequence is engineered to retain completely the amino acid sequence originally encoded by the starting nucleotide sequence, which is also known as the "parental" sequence. In particular embodiments, the optimized sequences herein have been engineered to have codons that are preferred in CHO mammalian cells.

As used herein, "C-terminus" refers to the carboxyl terminal amino acid of a polypeptide chain having a free carboxyl group (—COOH). As used herein, "N-terminus" refers to the amino terminal amino acid of a polypeptide chain having a free amine group (—$NH_2$).

The term "operably linked" or "functionally linked", as used herein, refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The phrases also apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

By "parent polypeptide", "parent protein", "precursor polypeptide", or "precursor protein" as used herein is meant an unmodified polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody. In some embodiments, the "parent" is a wild-type protein.

The term "in vivo half-life", as used herein, refers to the half-life of the molecule of interest or variants thereof circulating in the blood of a given mammal.

The term "subject" includes human and non-human animals. Non-human animals include all vertebrates, e.g., mammals and non-mammals, such as non-human primates, sheep, dog, cow, chickens, amphibians, and reptiles. In a preferred embodiment, the subject is human. Except when noted, the terms "patient" or "subject" are used herein interchangeably.

As used herein, phrases such as "a patient in need of treatment" or "a subject in need of treatment" includes subjects, such as mammalian subjects, that would benefit from administration of molecule or pharmaceutical composition of the present disclosure used, e.g., for detection, for a diagnostic procedure and/or for treatment.

As used herein, the terms term "treatment" or "treat" is herein defined as the application or administration of an Fc variant according to the disclosure, or a pharmaceutical composition comprising said Fc variant, to a subject or to an isolated tissue or cell line from a subject, where the subject has a particular disease (e.g., arthritis), a symptom associated with the disease, or a predisposition towards development of the disease (if applicable), where the purpose is to cure (if applicable), prevent (if applicable), delay the onset of, reduce the severity of, alleviate, ameliorate one or more symptoms of the disease, improve the disease, reduce or improve any associated symptoms of the disease or the predisposition toward the development of the disease. The term "treatment" or "treat" includes treating a patient suspected to have the disease as well as patients who are ill or who have been diagnosed as suffering from the disease or medical condition, and includes suppression of clinical relapse. The phrase "reducing the likelihood" refers to delaying the onset or development or progression of a disease, infection or disorder.

The term "therapeutically acceptable amount" or "therapeutically effective amount" or "therapeutically effective dose" interchangeably refer to an amount sufficient to effect the desired result (i.e., a reduction disease activity, reduction in disease progression, reduction in disease signs and/or symptoms, etc.). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage" and a "therapeutically effective dosage" of the molecules of the present disclosure can prevent the onset of (if applicable), or result in a decrease in severity of, respectively, disease symptoms.

As used herein, "selecting" and "selected" in reference to a patient is used to mean that a particular patient is specifically chosen from a larger group of patients due to the particular patient having a predetermined criterion. Similarly, "selectively treating a patient" refers to providing treatment to a patient that is specifically chosen from a larger group of patients due to the particular patient having a predetermined criteria. Similarly, "selectively administering" refers to administering a drug to a patient that is specifically chosen from a larger group of patients due to the particular patient having a predetermined criterion.

Unless otherwise specifically stated or clear from context, as used herein, the term "about" in relation to a numerical value is understood as being within the normal tolerance in the art, e.g., within two standard deviations of the mean. Thus, "about" can be within +/−10%, 9%, 8%, 7%, 6%, 5%, 4%, 3%, 2%, 1%, 0.1%, 0.05%, or 0.01% of the stated value, preferably +/−10% of the stated value. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "co-administer" refers to the simultaneous presence of two active agents in the blood of an individual. Active agents (e.g., additional therapeutic agents) that are co-administered with the disclosed antibodies and antigen-binding fragments can be concurrently or sequentially delivered.

Various aspects of the disclosure are described in further detail in the following sections and subsections.

Fc Variants of the Invention

Besides the ability of antibodies to bind antigen, an important feature of antibodies is their ability to recruit immune effector function. Engagement of the humoral immune response is mainly governed by interactions with C1q and the initiation of the complement cascade (Meyer et al., (2014) MABS, 6(5):1133-44). The cellular immune response occurs mostly due to the interactions between the antibody and Fc gamma receptors (FcγRs). Intracellular signalling through the activating receptors is modulated through the phosphorylation of immunoreceptor tyrosine-based activation motifs (ITAMs), which leads to effector functions such as antibody-dependent cell-mediated cytotoxicity (ADCC), antibody-dependent cellular phagocytosis (ADCP), and inflammation via the induction of cytokine secretion.

Although many antibody-based therapies have clinical and commercial success, these therapeutics are often only effective in a subset of patients. To date, all commercial antibodies are of the IgG class, predominantly IgG1, that recruit immune effector function via FcγRIII (CD16). The typical reaction involves activation of natural killer (NK) cells that display FcγRIII on their cell surface by the Fc portion of an IgG antibody triggering ADCC. However NK cells are only one component of the innate immune system and activation of other forms of leukocytes could be used to enhance the ADCC response triggered by IgG. The IgA class of antibodies engage FcαRI, which is widely expressed on neutrophils. Neutrophils comprise the highest percentage of innate effector cells found in the circulation and their activation triggers both ADCC and ADCP. In addition they have been shown to infiltrate many solid tumors (Gregory & Houghton (2011) supra). However, since IgG antibodies do not bind to the FcαRI, most commercial antibody-based therapeutics cannot activate neutrophils. As of yet, IgA based therapeutic antibodies have not been developed commercially due to perceived drawbacks with this class of antibody, in comparison to IgG antibodies. However, the applicants have shown that by making modifications to the Fc region, IgA antibodies can be generated with improved binding to FcαRI. This improved affinity of up to 1000-fold has been shown in cell based assays to directly translate to an increase in potency. Therefore, when used therapeutically, less antibody is required and the antibody can be dosed less often, which is preferential for patients.

In general, as outlined above, Fc variants include amino acid modifications in the CH2 domain and/or CH3 domain of the Fc region. An Fc variant comprises one or more amino acid modifications relative to a parent Fc polypeptide, wherein the amino acid modification(s) optionally provide one or more optimized properties, although in some cases, the variants exhibit substantially identical biological properties. Properties that may be optimized include but are not limited to enhanced or reduced affinity for an FcαRI. In an embodiment, the Fc variants of the present invention are modified to possess enhanced affinity for a human FcαRI. In a preferred embodiment, the Fc region of the Fc variant has been affinity matured, whereby amino acid modifications have been made in the CH2 and/or CH3 domains to enhance binding of the Fc region to its target FcαRI. Such types of modifications may improve the association and/or the dissociation kinetics for binding to the target antigen. This optimized property is anticipated to provide Fc variants with enhanced therapeutic properties in humans, for example enhanced effector function and greater anti-cancer potency.

By "greater affinity" or "improved affinity" or "enhanced affinity" or "better affinity" than a parent Fc polypeptide, as used herein is meant that an Fc variant binds to an Fc receptor with a significantly higher equilibrium constant of association ($K_A$) or lower equilibrium constant of dissociation ($K_D$) than the parent Fc polypeptide when the amounts of variant and parent polypeptide in the binding assay are essentially the same. For example, the Fc variant with improved Fc receptor binding affinity may display from about 10 fold to about 100 fold, e.g. at least about 50-fold relative to the parent Fc polypeptide as measured by surface plasmon resonance. For example, the Fc variant of a parent Fc polypeptide can have an increased affinity to human FcαRI of at least about 50, about 100, about 150, about 200, about 250, about 300-fold relative to the parent Fc polypeptide as measured by surface plasmon resonance.

The Fc receptor selectivity or specificity of a given Fc variant will provide different properties depending on whether it composes an antibody, Fc fusion, or Fc variant with a coupled fusion or conjugate partner.

Fc variants of the invention may comprise modifications that modulate interaction with Fc receptors other than FcαRI, including but not limited to FcγRs and/or FcRn.

An Fc variant of the present invention differs in amino acid sequence from its parent IgA Fc region by virtue of at least one amino acid modification. Thus, Fc variants of the present invention have at least one amino acid modification compared to the parent. Alternatively, the Fc variants of the present invention may have more than one amino acid modification as compared to the parent, for example from about one to ten amino acid modifications, preferably from one to five amino acid modifications, from one to four amino acid modifications, from one to three amino acid modifications, from one to two amino acid modifications compared to the parent. Thus the sequences of the Fc variants and those of the parent Fc polypeptide are substantially homologous or identical. For example, the variant Fc variant sequences herein will possess about 80% homology (including identity) with the parent Fc variant sequence, preferably at least about 90% homology, and most preferably at least about 95, 96, 97, 98 and 99% identity.

In one embodiment, one or more amino acid insertions, deletions or substitutions are made. All of these substitutions may be made in an IgA molecule, for example IgA1 or IgA2, particularly in IgA2. Preferably, in one embodiment, amino acid substitutions can be made at positions in the Fc region of CH2.10, CH2.89, CH2.91, CH2.94, CH2.97, CH2.99, CH3.45, CH3.105, CH3.109, CH3.118 and/or CH3.124, wherein the numbering of the amino acid modification is according to IMGT numbering for C-domain. These amino acid substitutions include, but are not limited to: A_CH2.10_S, L_CH2.89_I, G_CH2.91_Q, G_CH2.91_V, Q_CH2.94_E, N_CH2.97_H, N_CH2.97_Y, G_CH2.99_W, S_CH3.45_D, M_CH3.105_Y, E_CH3.109_D, Q_CH3.118_Y and/or L_CH3.124_F, again, as any possible combination of substitution(s), insertion(s) and deletion(s), wherein the numbering of the amino acid modification is according to IMGT numbering for C-domain. In a preferred embodiment, amino acid substitutions or combinations thereof can include, but are not limited to: Q_CH2.94_E, N_CH2.97Y, S_CH3.45_D, M_CH3.105_Y, Q_CH3.118_Y, Q_CH2.94_E/N_CH2.97_Y, Q_CH2.94_E/S_CH3.45_D, Q_CH2.94_E/M_CH3.105_Y, N_CH2.97_Y/S_CH3.45_D, N_CH2.97_Y/M_CH3.105_Y, S_CH3.45_D/M_CH3.105_Y, M_CH3.105_Y/Q_CH3.118_Y, Q_CH2.94_E/N_CH2.97_Y/M_CH3.105_Y, N_CH2.97_Y/S_CH3.45_D/M_CH3.105_Y, Q_CH2.94_E/S_CH3.45_D/M_CH3.105_Y, M_CH3.105_Y/Q_CH3.118_Y/S_CH3.45_D, Q_CH2.94_E/N_CH2.97_Y/S_CH3.45_D, Q_CH2.94_E/N_CH2.97_Y/S_CH3.45_D/M_CH3.105_Y, Q_CH2.94_E/N_CH2.97_Y/M_CH3.105_Y/Q_CH3.118_Y, Q_CH2.94_E/N_CH2.97_Y/S_CH3.45_D/M_CH3.105_Y/Q_CH3.118_Y, A_CH2.10_S, L_CH2.89_I, G_CH2.91_V, N_CH2.97_H, G_CH2.99_W, E_CH3.109_D, L_CH3.124_F, L_CH2.89_I/G_CH2.91_V/Q_CH2.94_E/N_CH2.97_Y/G_CH2.99_W, wherein the numbering of the amino acid modification is according to IMGT numbering for C-domain.

In one embodiment, amino acid substitutions can be made at positions in the Fc region of CH2.94, CH2.97, CH3.45, CH3.105 and CH3.118. In one embodiment, amino acid substitutions can be made at positions in the Fc region of Glu at position CH2.94, Tyr at position CH2.97, Asp at position CH3.45, Tyr at position CH3.105 or Tyr at position CH3.118. In a preferred embodiment, amino acid substitutions can be made in the Fc region of Q_CH2.94_E, L_CH2.97_Y, S_CH3.45_D, M_CH3.105_Y, Q_CH3.118_Y.

Functionally, variants that result in increased binding to FcαRI find particular use in some embodiments. The Fc variants may comprise more than one protein chain. That is, the Fc variant may find use in an antibody or Fc fusion that is a monomer or an oligomer, including a homo- or hetero-oligomer.

Fc Fusions, Antibody Fusions and Antibody Conjugates

Fc polypeptides and antibodies of the invention can be a variety of structures, including, but not limited antibody fragments, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. The present invention includes variant Fc polypeptides and antibodies (e.g., antibodies or antibody-like molecules) or fragments thereof recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; EP 307434 and EP 367166; WO 1996/04388 and WO 1991/06570; Ashkenazi et al., (1991) PNAS. USA 88:10535-10539; Zheng et al., (1995) J. Immunol. 154: 5590-5600; and Vil et al., (1992) PNAS. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the disclosure or fragments thereof (e.g., molecules or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama (1998) Trends Biotechnol. 16(2):76-82; Hansson et al., (1999) J. Mol. Biol. 287: 265-76; and Lorenzo & Blasco (1998) Biotechniques, 24(2):308-313 (each of these patents and publications are hereby incorporated by reference in its entirety). The molecules described herein or fragments thereof may be altered by being subjected to random mutagenesis by error-prone PCR, random nucleotide insertion or other methods prior to recombination. A polynucleotide encoding a fragment of the present molecule may be recombined with one or more components, motifs, sections, parts, domains, fragments, etc. of one or more heterologous molecules.

Moreover, the variant Fc polypeptides and antibodies of the present disclosure can be fused to marker sequences, such as a peptide to facilitate purification. In preferred embodiments, the marker amino acid sequence is a hexa-histidine peptide (SEQ ID NO: 81), such as the tag provided in a pQE vector (QIAGEN, Inc., 9259 Eton Avenue, Chatsworth, CA, 91311), among others, many of which are commercially available. As described in Gentz et al., (1989) PNAS. USA 86:821-824, for instance, hexa-histidine (SEQ ID NO: 81) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "flag" tag.

In other embodiments, the variant Fc polypeptides and antibodies of the present disclosure are conjugated to a diagnostic or detectable agent. Such molecules can be useful for monitoring or prognosing the onset, development, progression and/or severity of a disease or disorder as part of a clinical testing procedure, such as determining the efficacy of a particular therapy. Such diagnosis and detection can accomplished by coupling the molecules to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present application further encompasses uses of the variant Fc polypeptides and antibodies of the present disclosure conjugated to a therapeutic moiety. For example, the therapeutic moiety may be a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Furthermore, the variant Fc polypeptides and antibodies may be conjugated to a therapeutic moiety or drug moiety that modifies a given biological response. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

For further discussion of types of cytotoxins, linkers and methods for conjugating therapeutic agents to the engineered immunoglobulin, see also Saito et al., (2003) Adv. Drug Deliv. Rev. 55:199-215; Trail et al., (2003) Cancer Immunol. Immunother. 52: 328-337; Payne (2003) Cancer Cell 3: 207-212; Allen (2002) Nat. Rev. Cancer, 2:750-763; Pastan & Kreitman (2002) Curr. Opin. Investig. Drugs, 3: 1089-1091; Senter & Springer (2001) Adv. Drug Deliv. Rev. 53: 247-264.

The variant Fc polypeptides and antibodies of the present disclosure also can be conjugated to a radioactive isotope to generate cytotoxic radiopharmaceuticals, also referred to as radioimmunoconjugates. Examples of radioactive isotopes that can be conjugated to engineered immunoglobulins for use diagnostically or therapeutically include, but are not limited to, iodinel31, indium111, yttrium90, and lutetium177. Method for preparing radioimmunconjugates are established in the art. See, e.g., Denardo et al., (1998) Clin Cancer Res. 4(10): 2483-90; Peterson et al., (1999) Bioconjug. Chem. 10(4):553-7; and Zimmerman et al., (1999) Nucl. Med. Biol. 26(8): 943-50, each incorporated by reference in their entireties.

Techniques for conjugating therapeutic moieties to variant Fc polypeptides such as antibodies or antibody-like molecules are known, see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy: A Review", in Monoclonal Antibodies 84: Biological And Clinical Applications, Pinchera et al. (eds.), pp. 475-506 (1985); "Analysis, Results, and Future Prospective of the Therapeutic Use of Radiolabeled Antibody in Cancer Therapy", in Monoclonal Antibodies For Cancer Detection and Therapy, Baldwin et al. (eds.), pp. 303-16 (Academic Press 1985), and Thorpe et al., (1982) Immunol. Rev. 62:119-58.

The variant Fc polypeptides and antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Fc variants of the invention may comprise one or more modifications that provide reduced or enhanced internalization of an Fc variant. In one embodiment, Fc variants of the present invention can be utilized or combined with additional modifications in order to reduce the cellular internalization of an Fc variant that occurs via interaction with one or more Fc ligands. This property might be expected to enhance effector function, and potentially reduce immunogenicity of the Fc variants of the invention. Alternatively, Fc variants of the present invention can be utilized directly or combined with additional modifications in order to enhance the cellular internalization of an Fc variant that occurs via interaction with one or more Fc ligands.

In a preferred embodiment, modifications are made to improve biophysical properties of the Fc variants of the present invention, including but not limited to stability, solubility, and oligomeric state. Modifications can include, for example, substitutions that provide more favorable intramolecular interactions in the Fc variant such as to provide greater stability, or substitution of exposed nonpolar amino acids with polar amino acids for higher solubility. A number of optimization goals and methods are described in U.S. Ser. No. 10/379,392, incorporated herein by reference, that may find use for engineering additional modifications to further optimize the Fc variants of the present invention. The Fc variants of the present invention can also be combined with additional modifications that reduce oligomeric state or size, such that tumor penetration is enhanced, or in vivo clearance rates are increased as desired. Other modifications to the Fc variants of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., (2001) J. Immunol., 166:1320-1326; Stevenson et al., (2002) Recent Results Cancer Res. 159: 104-12; U.S. Pat. No. 5,681,566; Caron et al., (1992), J. Exp. Med. 176: 1191-1195, and Shapes (1992) J. Immunol. 148(9): 2918-22, all incorporated herein by reference. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Bioi. 270(1):26-35, and Carter et al., 2001, J. Immunol. Methods 248:7-15, both incorporated herein by reference. Additional modifications include modifications in the hinge and CH3 domains, in which the modifications reduce the propensity to form dimers.

Preparing Fc Variant Polypeptides

Antibodies and fragments thereof comprising variant Fc polypeptides as disclosed herein, can be produced by a variety of techniques, including conventional monoclonal antibody methodology e.g., the standard somatic cell hybridization technique of Kohler & Milstein, (1975) Nature 256: 495.

An animal system for preparing hybridomas is the murine system. Hybridoma production in the mouse is a known procedure. Immunization protocols and techniques for isolation of immunized splenocytes for fusion are known in the art. Fusion partners (e.g., murine myeloma cells) and fusion procedures are also known.

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, antibodies or fragments thereof comprising Fc variants as described herein are human monoclonal antibodies. Such human monoclonal antibodies can be generated using transgenic or transchromosomic mice carrying parts of the human immune system rather than the mouse system. These transgenic and transchromosomic mice include mice referred to herein as HUMAB mice and KM mice, respectively, and are collectively referred to herein as "human Ig mice".

The HUMAB mouse (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg et al., (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al., (1994) supra; reviewed in Lonberg, (1994) Handbook of Experimental Pharmacology 113: 49-101; Lonberg & Huszar, (1995) Intern. Rev. Immunol. 13: 65-93, and Harding & Lonberg, (1995) Ann. N. Y. Acad. Sci. 764: 536-546). The preparation and use of HUMAB mice, and the genomic modifications carried by such mice, is further described in Taylor et al., (1992) Nucleic Acids Research 20:6287-6295; Chen et al., (1993) International Immunology 5: 647-656; Tuaillon et al., (1993) PNAS USA 94:3720-3724; Choi et al., (1993) Nature Genetics 4:117-123; Chen et al., (1993) EMBO J. 12:821-830; Tuaillon et al., (1994) J. Immunol. 152:2912-2920; Taylor et al., (1994) Int. Immun., 579-591; and Fishwild et al., (1996) Nature Biotech., 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg & Kay; U.S. Pat. No. 5,545,807 to Surani et al.; WO 92/103918, WO 93/12227, WO 94/25585, WO 97113852, WO 98/24884 and WO 99/45962, all to Lonberg & Kay; and WO 01/14424 to Korman et al.

In another embodiment, human antibodies can be raised using a mouse that carries human immunoglobulin sequences on transgenes and transchomosomes such as a mouse that carries a human heavy chain transgene and a human light chain transchromosome. Such mice, referred to herein as "KM mice", are described in detail in WO 2002/43478 (Ishida et al).

Still further, alternative transgenic animal systems expressing human immunoglobulin genes are available in the art and can be used to raise human antibodies. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 (Kucherlapati et al).

Moreover, alternative transchromosomic animal systems expressing human immunoglobulin genes are available in the art and can be used to raise human antibodies. For example, mice carrying both a human heavy chain transchromosome and a human light chain transchromosome, referred to as "TC mice" can be used; such mice are described in Tomizuka et al., (2000) PNAS USA 97:722-727. Furthermore, cows carrying human heavy and light chain transchromosomes have been described in the art (Kuroiwa et al., (2002) Nature Biotechnology 20:889-894) and can be used to raise human antibodies useful in the present application.

Human monoclonal antibodies or fragments thereof can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 (Ladner et al); U.S. Pat. Nos. 5,427,908 and 5,580,717 (Dower et al); U.S. Pat. Nos. 5,969,108 and 6,172,197 (McCafferty et al); and U.S. Pat. Nos. 5,885,793; 6,521,404; 6,544,731; 6,555,313; 6,582,915 and 6,593,081 (Griffiths et al).

Human monoclonal antibodies or fragments thereof useful in the disclosure can also be prepared using SCID mice into which human immune cells have been reconstituted such that a human antibody response can be generated upon immunization. Such mice are described in, for example, U.S. Pat. Nos. 5,476,996 and 5,698,767 (Wilson et al).

Human monoclonal antibodies or fragments thereof prepared according to methods described infra can be further modified to mutate amino acid residues within the VH, VL, CH1, CL, CH2, CH3 domains to thereby improve one or more binding properties (e.g., affinity) of the antibody or fragment thereof to a receptor of interest, a process known as "affinity maturation." Site-directed mutagenesis or PCR-mediated mutagenesis can be performed to introduce the mutation(s) and the effect on receptor binding, or other functional property of interest, can be evaluated in in vitro or in vivo assays as described herein and provided in the Examples. Therefore, in one embodiment, the disclosure relates to affinity matured antibodies or fragments thereof, in particular to affinity matured Fc regions. The mutations may be amino acid substitutions, additions or deletions. For example, an Fc variant of the disclosure is an affinity-matured Fc region wherein no more than one, two, three, four or five residues within the CH2 domain and/or CH3 domain have been modified. All of these substitutions may be made in an IgA molecule, for example IgA1 or IgA2, particularly in IgA2. In a preferred embodiment, amino acid substitutions can be made at positions in the Fc region at CH2.10, CH2.89, CH2.91, CH2.94, CH2.97, CH2.99, CH3.45, CH3.105, CH3.109, CH3.118 and/or CH3.124, wherein the numbering of the amino acid modification is according to IMGT numbering for C-domain. These amino acid substitutions include, but are not limited to: A_CH2.10_S, L_CH2.89_I, G_CH2.91_Q, G_CH2.91_V, Q_CH2.94_E, N_CH2.97_H, N_CH2.97_Y, G_CH2.99_W, S_CH3.45_D, M_CH3.105_Y, E_CH3.109_D, Q_CH3.118_Y and/or L_CH3.124_F, again, as any possible combination of substitution(s), insertion(s) and deletion(s), wherein the numbering of the amino acid modification is according to IMGT numbering for C-domain. In a preferred embodiment, amino acid substitutions or combinations thereof in affinity matured Fc variants of the present invention can include, but are not limited to: Q_CH2.94_E, N_CH2.97Y, S_CH3.45_D, M_CH3.105_Y, Q_CH3.118_Y, Q_CH2.94_E/N_CH2.97_Y, Q_CH2.94_E/S_CH3.45_D, Q_CH2.94_E/M_CH3.105_Y, N_CH2.97_Y/S_CH3.45_D, N_CH2.97_Y/M_CH3.105_Y, S_CH3.45_D/M_CH3.105_Y, M_CH3.105_Y/Q_CH3.118_Y, Q_CH2.94_E/N_CH2.97_Y/M_CH3.105_Y, N_CH2.97_Y/S_CH3.45_D/M_CH3.105_Y, Q_CH2.94_E/S_CH3.45_D/M_CH3.105_Y, M_CH3.105_Y/Q_CH3.118_Y/S_CH3.45_D, Q_CH2.94_E/N_CH2.97_Y/S_CH3.45_D, Q_CH2.94_E/N_CH2.97_Y/S_CH3.45_D/M_CH3.105_Y, Q_CH2.94_E/N_CH2.97_Y/M_CH3.105_Y/Q_CH3.118_Y, Q_CH2.94_E/N_CH2.97_Y/S_CH3.45_D/M_CH3.105_Y/Q_CH3.118_Y, A_CH2.10_S, L_CH2.89_I, G_CH2.91_V, N_CH2.97_H, G_CH2.99_W, E_CH3.109_D, L_CH3.124_F, L_CH2.89_I/G_CH2.91_V/Q_CH2.94_E/N_CH2.97_Y/G_CH2.99_W, wherein the numbering of the amino acid modification is according to IMGT numbering for C-domain.

Nucleic Acids and Expression Systems

The present invention also encompasses nucleic acids encoding the polypeptide chains of the Fc variants described herein. Nucleic acid molecules of the disclosure include DNA and RNA in both single-stranded and double-stranded form, as well as the corresponding complementary sequences. The nucleic acid molecules of the disclosure include full-length genes or cDNA molecules as well as a combination of fragments thereof. The nucleic acids of the disclosure are derived from human sources but can include those derived from non-human species.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Variant sequences, for example a library of variant sequences can be prepared by site specific mutagenesis of nucleotides in the DNA encoding the polypeptide, using cassette or PCR mutagenesis or other techniques are known in the art, to produce DNA encoding the variant, and thereafter expressing the recombinant DNA in cell culture as outlined herein.

As "optimized nucleotide sequence" means a nucleotide sequence has been altered to encode an amino acid sequence using codons that are preferred in the production cell, for example, a Chinese Hamster Ovary cell (CHO). The optimized nucleotide sequence is engineered to retain completely the amino acid sequence originally encoded by the starting nucleotide sequence, which is also known as the "parental" sequence.

The present disclosure also provides expression systems and constructs in the form of plasmids, expression vectors, transcription or expression cassettes which comprise at least one polynucleotide as above. In addition, the disclosure provides host cells comprising such expression systems or constructs.

In one embodiment, the present invention provides a method of preparing an antibody or fragment thereof comprising a variant Fc region as described herein, the method comprising the steps of: (a) culturing a host cell comprising a nucleic acid encoding the variant heavy chain and light chain polypeptides, wherein the cultured host cell expresses the variant polypeptides; and (b) recovering the antibody or fragment thereof from the host cell culture.

Expression vectors of use in the present disclosure may be constructed from a starting vector such as a commercially available vector. After the vector has been constructed and a nucleic acid molecule encoding polypeptide chains of the engineered immunoglobulin has been inserted into the proper site of the vector, the completed vector may be inserted into a suitable host cell for amplification and/or polypeptide expression. The transformation of an expression vector into a selected host cell may be accomplished by known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are known to the skilled artisan, and are set forth, for example, in Sambrook et al., 2001, supra.

Typically, expression vectors used in the host cells will contain sequences for plasmid maintenance and for cloning and expression of exogenous nucleotide sequences. Such sequences, collectively referred to as 'flanking sequences', in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

A host cell, when cultured under appropriate conditions, can be used to express Fc variants that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are known in the art and include, but are not limited to, immortalized cell lines available from the American Type Culture Collection (ATCC) and any cell lines used in an expression system known in the art can be used to make polypeptides comprising the engineered immunoglobulins of the present disclosure. In general, host cells are transformed with a recombinant expression vector that comprises DNA encoding a desired engineered immunoglobulin. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 cells, L cells, Cl27 cells, 3T3 cells, Chinese hamster ovary (CHO) cells, or their derivatives and related cell lines which grow in serum free media, HeLa cells, BHK cell lines, the CVIIEBNA cell line, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *S. cerevisiae, S. pombe, Kluyveromyces* strains, *Candida*, or any yeast strain capable of expressing heterologous polypeptides. Suitable bacterial strains include *E. coli, B. subtilis, S. typhimurium*, or any bacterial strain capable of expressing heterologous polypeptides. If the engineered immunoglobulin is made in yeast or bacteria, it may be desirable to modify the product produced therein, for example by phosphorylation or glycosylation of the appropriate sites, in order to obtain a functional product. Such covalent attachments can be accomplished using known chemical or enzymatic methods.

In further embodiments, the Fc variants of the present invention comprise modifications that remove proteolytic degradation sites. These may include, for example, protease sites that reduce production yields, as well as protease sites that degrade the administered protein in vivo.

In a preferred embodiment, Fc variants are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is known in the art, a variety of natural proteins bind Fc and antibodies, and these proteins can find use in the present invention for purification of Fc variants. For example, the bacterial proteins A and G bind to the Fc region. Likewise, the bacterial protein L binds to the Fab region of some antibodies, as of course does the antibody's target antigen. Purification can often be enabled by a particular fusion partner. For example, Fc variants may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference.

Pharmaceutical Compositions and Dosing

Provided herein are pharmaceutical compositions comprising the Fc variants of the present disclosure. The Fc variant can be incorporated in an antibody format, for example as a monospecific, bispecific or multi-specific antibody, in combination with one or more pharmaceutically acceptable excipients, diluents or carriers.

To prepare pharmaceutical or sterile compositions comprising an Fc variant of the present disclosure, the molecule is mixed with a pharmaceutically acceptable carrier or excipient.

The phrase "pharmaceutically acceptable" means approved by a regulatory agency of a federal or a state government, or listed in the U.S. Pharmacopeia or other generally recognized pharmacopeia for use in animals, and more particularly, in humans. The term "pharmaceutical composition" refers to a mixture of at least one active ingredient (e.g., an antibody comprising an Fc variant of the disclosure) and at least one pharmaceutically-acceptable excipient, diluent or carrier. A "medicament" refers to a substance used for medical treatment.

Pharmaceutical compositions of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams and Wilkins, New York, N.Y.; Avis, et al. (eds.) (1993) Pharmaceutical Dosage Forms: Oral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner & Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert, et al. (2003) New Engl. J. Med. 348:601-608; Milgrom, et al. (1999) New Engl. J. Med. 341:1966-1973; Slamon, et al. (2001) New Engl. J. Med. 344:783-792; Beniaminovitz, et al. (2000) New Engl. J. Med. 342:613-619; Ghosh, et al. (2003) New Engl. J. Med. 348:24-32; Lipsky, et al. (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Pharmaceutical compositions comprising the Fc variant of the present disclosure can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation.

The desired dose of a therapeutic comprising the Fc variant of the present disclosure is about the same as for an antibody or polypeptide, on a moles/kg body weight basis. The doses administered to a subject may number at least 1, 2, 3, 4, 5, 6, 7, 8, 9, 10, 11, or 12, or more.

For a therapeutic comprising the Fc variant of the present disclosure, the dosage administered to a patient may be about 0.0001 mg/kg to about 100 mg/kg of the patient's body weight. Where a series of doses are administered, these may, for example, be administered approximately every day, approximately every week, approximately every month. The doses may, for example, continue to be administered until disease progression, adverse event, or other time as determined by the physician.

An effective amount for a particular patient may vary depending on factors such as the condition being treated, the overall health of the patient, the method route and dose of administration and the severity of side effects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

Where necessary, the therapeutic comprising the Fc variant of the present disclosure may be incorporated into a composition that includes a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and WO 92/19244, WO 97/32572, WO 97/44013, WO 98/31346, and WO 99/66903, each of which is incorporated herein by reference their entirety.

A therapeutic comprising the Fc variant of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically.

The therapeutic comprising the Fc variant of the present disclosure may be administered via any of the above routes using, e.g., an injection device, an injection pen, a vial and syringe, pre-filled syringe, autoinjector, an infusion pump, a patch pump, an infusion bag and needle, etc. If the therapeutic comprising the Fc variant of the present disclosure is administered in a controlled release or sustained release system, a pump may be used to achieve controlled or sustained release (see Langer, supra; Sefton (1987) CRC Crit. Ref Biomed. Eng. 14:20; Buchwald et al., (1980) Surgery 88:507; Saudek et al., (1989) N. Engl. J. Med. 321:574). Polymeric materials can be used to achieve controlled or sustained release of the therapies of the disclosure (see e.g., Medical Applications of Controlled Release, Langer and Wise (eds.), CRC Pres., Boca Raton, Fla. (1974); Controlled Drug Bioavailability, Drug Product Design and Performance, Smolen & Ball (eds.), Wiley, New York (1984); Ranger & Peppas (1983) J. Macromol. Sci. Rev. Macromol. Chem. 23:61; see also Levy et al., (1985) Science 228:190; During et al., (1989) Ann. Neurol. 25:351; Howard et al., (1989) J. Neurosurg., 7(1):105; U.S. Pat. Nos. 5,679,377; 5,916,597; 5,912,015; 5,989,463; 5,128,326; WO 99/15154; and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (Science (1990) 249:1527-1533). Any technique known to one of skill in the art can be used to produce sustained release formulations comprising one or more Fc variants of the present application. See, e.g., U.S. Pat. No. 4,526,938, WO 91/05548, WO 96/20698, Ning et al., (1996) Radiotherapy & Oncology 39: 179-189; Song et al., (1995) PDA Journal of Pharm Sci & Tech., 50: 372-397; Cleek et al., (1997) Pro. Int'l. Symp. Control. Rel. Bioact. Mater. 24: 853-854; Lam et al., (1997) Proc. Int'l. Symp. Control Rel. Bioact. Mater., 24: 759-760, each of which is incorporated herein by reference in their entirety.

If a pharmaceutical composition comprising the Fc variant of the present disclosure is administered topically, it can be formulated in the form of an ointment, cream, transdermal patch, lotion, gel, shampoo, spray, aerosol, solution, emulsion, or other forms known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as Freon) or in a squeeze bottle. Moisturizers or humectants can also be added to pharmaceutical compositions and dosage forms if desired. Examples of such additional ingredients are known in the art.

If a pharmaceutical composition comprising the Fc variant of the present disclosure is administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

A pharmaceutical composition comprising the Fc variant of the present disclosure can also be cyclically administered to a patient.

In certain embodiments, pharmaceutical compositions comprising an Fc variant of the present disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (Bloeman et al., (1995) FEBS Lett., 357: 140; Owais et al., (1995) Antimicrob. Agents Chemother., 39: 180); surfactant protein A receptor (Briscoe et al., (1995) Am. J. Physiol. 1233:134); p 120 (Schreier et al (1994) J. Biol. Chem. 269:9090); see also Keinanen & Laukkanen (1994) FEBS Lett., 346:123-6; Killion & Fidler (1994) Immunomethods, 4:273.

The present application also provides protocols for the co-administration or treatment of patients using a pharmaceutical composition comprising Fc variants of the present disclosure in combination with other therapies or therapeutic agent(s). Methods for co-administration or treatment with an additional therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%, by at least 20%, at least about 30%, at least 40%, or at least 50%.

In some embodiments, a pharmaceutical composition of the disclosure further comprises one or more additional therapeutic agents.

In addition to the above therapeutic regimens, the patient may be subjected to surgery and other forms of physical therapy.

Therapeutic Application

Therapeutic or pharmaceutical compositions comprising Fc variants of the present disclosure, whilst not being limited to, are useful for the treatment, prevention, or amelioration of disorders or conditions in which there is an abnormal proliferation of cells, termed herein as "cell proliferative disorders or conditions". In one aspect, the disclosure provides methods for treating a cell proliferative disorder or condition. In one aspect, the subject of treatment is a human.

Examples of cell proliferative disorders or conditions that may be treated, prevented, or ameliorated using therapeutic or pharmaceutical compositions comprising Fc variants of the present disclosure include but are not limited to cancer. As used herein, the term "cancer" is meant to include all types of cancerous growths or oncogenic processes, metastatic tissues or malignantly transformed cells, tissues, or organs, irrespective of histopathologic type or stage of invasiveness.

In specific embodiments, the administration of a therapeutic or pharmaceutical composition comprising a Fc variant of the present disclosure to a subject in accordance with the methods described herein achieves one, two, or three or more results: (1) a reduction in the growth of a tumor or neoplasm; (2) a reduction in the formation of a tumor; (3) an eradication, removal, or control of primary, regional and/or metastatic cancer; (4) a reduction in metastatic spread; (5) a reduction in mortality; (6) an increase in survival rate; (7) an increase in length of survival; (8) an increase in the number of patients in remission; (9) a decrease in hospitalization rate; (10) a decrease in hospitalization lengths; and (11) the maintenance in the size of the tumor so that it does not increase by more than 10%, or by more than 8%, or by more than 6%, or by more than 4%; preferably the size of the tumor does not increase by more than 2%.

In a specific embodiment, the administration of a therapeutic or pharmaceutical composition comprising a Fc variant of the present disclosure to a subject with cancer (in some embodiments, an animal model for cancer) in accordance with the methods described herein inhibits or reduces the growth of a tumor by at least about 2 fold, preferably at least about 2.5 fold, at least about 3 fold, at least about 4 fold, at least about 5 fold, at least about 7 fold, or at least about 10 fold relative to the growth of a tumor in a subject with cancer (in some embodiments, in the same animal model for cancer) administered a negative control as measured using assays known in the art. In another embodiment, the administration of a therapeutic or pharmaceutical composition comprising a Fc variant of the present disclosure to a subject with cancer (in some embodiments, an animal model for cancer) in accordance with the methods described herein inhibits or reduces the growth of a tumor by at least about 25%, at least about 30%, at least about 35%, at least about 40%, at least about 45%, at least about 50%, at least about 55%, at least about 60%, at least about 65%, at least 70%, at least 75%, at least about 80%, at least about 85%, at least about 90%, or at least about 95% relative to the growth of a tumor in a subject with cancer (in some embodiments, in the same animal model for cancer) administered a negative control, as measured using assays known in the art.

Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the disclosure.

Exemplary cancers whose growth can be inhibited using a therapeutic or pharmaceutical composition comprising a Fc variant of the present disclosure include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer), epithelial cancer. Additionally, refractory or recurrent malignancies can be treated using the combination therapy described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, neuroblastoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers.

In a specific embodiment, the cancer is breast cancer, neuroblastoma, lymphoma, colon cancers, pancreatic ductal adenocarcinoma, melanoma, renal cell carcinoma, bladder cancer, colorectal cancer, non-small cell lung cancer, non-Hodgkins lymphoma, multiple myeloma.

Combination Therapies

Administered "in combination", in reference to an additional therapeutic agent, means that two (or more) different treatments are delivered to the subject during the course of the subject's affliction with the disorder. In some embodiments, the delivery of one treatment is still occurring when the delivery of the second begins, so that there is overlap in terms of administration. This is referred to as "simultaneous" or "concurrent delivery". In other embodiments, the delivery of one treatment ends before the delivery of the other treatment begins. This is referred to as "sequential delivery". In some embodiments of either case, the treatment is more effective because of combined administration. The additional therapeutic agent(s) of the combination therapies of the present disclosure can also be cyclically administered. Combination cycling therapy involves the administration of a first therapy for a period of time, followed by the administration of a second for a period of time and repeating this sequential administration.

A therapeutic or pharmaceutical composition comprising an engineered immunoglobulin as described herein can be administered together with one or more other therapies, e.g., anti-cancer agents, cytokines or anti-hormonal agents, to treat and/or manage cancer. Other therapies that can be used in combination with a therapeutic or pharmaceutical composition comprising an engineered immunoglobulin as described herein, include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

Non-limiting examples of one or more other therapies that can be used in addition to a therapeutic or pharmaceutical composition comprising an engineered immunoglobulin as described herein include, but not limited to, chemotherapy, radiotherapy, cytotoxic agents, chemotherapeutic agents, cytokines, kinase inhibitors, low dose gemcitabine, 5-fluorouracil and cytokine modulators. In particular, one or more other therapies that can be used in addition to a therapeutic or pharmaceutical composition comprising an engineered immunoglobulin of the present disclosure include in particular immune oncology approaches that would perturb the tumor microenvironment, for example, recombinant IL-2, recombinant IL-15, recombinant IL-12, recombinant IL-21, anti-IL1β, anti-TGFβ, anti-CD39, anti-CD73, anti-CTLA4, anti-PD(L)1, anti-TIM3, HDAC inhibitors, HIF1a inhibitors and anti-angiogenics such as anti-VEGF.

Kits

The disclosure also encompasses kits for treating a patient having a cell proliferative disorder. Such kits comprise a therapeutically effective amount of a therapeutic or pharmaceutical composition comprising a Fc variant as described herein. Additionally, such kits may comprise means for administering the therapeutic or pharmaceutical composition comprising a Fc variant as described herein (e.g., an autoinjector, a syringe and vial, a prefilled syringe, a prefilled pen) and instructions for use. These kits may contain additional therapeutic agents (described infra) for treating a cell proliferative disorder. Such kits may also comprise instructions for administration of the therapeutic or pharmaceutical composition comprising a Fc variant as described herein, to treat the patient. Such instructions can provide the dose, route of administration, regimen, and total treatment duration for use with the therapeutic or pharmaceutical composition comprising a Fc variant as described herein.

The phrase "means for administering" is used to indicate any available implement for systemically administering a drug to a patient, including, but not limited to, a pre-filled syringe, a vial and syringe, an injection pen, an auto-injector, an IV drip and bag, an infusion pump, a patch, an infusion bag and needle, etc. With such items, a patient may self-administer the drug (i.e., administer the drug without the assistance of a physician) or a medical practitioner may administer the drug.

EXAMPLES

The following examples are provided to further illustrate the disclosure but not to limit its scope. Other variants of the disclosure will be readily apparent to one of ordinary skill in the art and are encompassed by the appended claims.

All constructs derived from amino acid sequences generated according to Example 1 and were expressed in mammalian systems and purified (Example 2) to be assessed for binding to human FcαRI and rat FcαR using surface plasmon resonance (SPR) (Example 3). Finally, functionality of the engineered immunoglobulins was assessed by a cell-based assay using human freshly isolated PMN (Example 4). All Examples were performed using the Fc variants in an antibody format comprising VH and VL domains recognizing the antigen HER2 and engineered hinge and Fc regions based on IgA2. SEQ ID NO: 1 is a full length heavy chain sequence of an anti-HER2 binding antibody having a VH domain that binds HER2 and a hinge and constant domains from IgG1. SEQ ID NO: 2 is a full length heavy chain sequence of an anti-HER2 binding antibody having a VH domain that binds HER2 and a hinge and constant domains from the m2 allotype of IgA2 (Lombana et al., (2019) MABS, 11: 1122-38). SEQ ID NO: 4 is the light chain sequence of an anti-HER2-binding antibody having a VL domain that binds HER2 and a constant domain (CL) from IgA2.

Example 1: IgA2 Fc Affinity Maturation for hFcαRI 1.1 IgA2 Fc Library Design In-silico analysis was performed on the IgA1 Fc/hFcαRI complex using the crystal structure PDB 1OW0, since IgA1 has a similar structure to IgA2, differing only in the hinge region. All residues located in proximity to hFcαRI were considered to be potentially involved in the IgA1 Fc/hFcαRI interaction and were classified into two categories: (i) residues from the "core" interface region (LCH2.15, LCH2.15.1, MCH3.105, ECH3.109, PCH3.113, LCH3.114, ACH3.115, FCH3.116, QCH3.118, wherein the residues are numbered according to the IMGT numbering for C-domain) and (ii) residues from the "shell" region surrounding the core (QCH2.94, NCH2.97, HCH2.98, RCH3.1, ECH3.3, RCH3.40, LCH3.42, SCH3.45, ECH3.45.2, wherein the residues are numbered according to the IMGT numbering for C-domain). Both groups of residues were diversified using a trinucleotide-directed mutagenesis (TRIM) based approach (Virnekss et al, (1994) Nucleic Acids Res., 22: 5600-5607; Knappik et al., (2000) J Mol Biol., 296: 57-86) to generate two libraries L1 and L2, corresponding to the 'shell' region and the 'core' region, respectively.

A third library was generated using error prone PCR of the IgA2 Fc domain (EP library) (Gram et al, (1992) PNAS USA, 89: 3576-3580).

1.2 Library Screening by Yeast Display

All three IgA2 Fc libraries were screened using yeast display technology (Boder et al., (1997) Nature Biot., 15: 553-557). Briefly, IgA Fcs were displayed on yeast cell membranes via the α-agglutinin (Aga1/Aga2) protein heterodimer, with IgA2 Fc fused to the N-terminus of the Aga2 protein. Four rounds of sorting were performed:

(i) During the first round of sorting, all three libraries were grown for two days at 20° C. with shaking in selective medium containing 1% raffinose and 2% galactose to induce IgA2 Fc expression on yeast cell surface. Each culture was pelleted, the supernatant removed, and the pellet washed once with PBSM (PBS (Gibco, Waltham, MA) with 1% BSA (bovine serum albumin) and 2 mM EDTA. After resuspension of pellets in 20 ml PBSM, 100 μl each streptavidin and anti-biotin microbeads (Miltenyi Biotec, Bergisch Gladbach, Germany) were added. Cells were incubated for 1 hr at room temperature with rotation. The beads were then removed using a MACS LS column (Miltenyi). The libraries were then pelleted and resuspended in 20 ml PBSM+50 nM biotinylated FcαRI (CD89) (SEQ ID NO: 5) and incubated for 1 hr at room temperature with rotation. The cells were then pelleted, the supernatant removed, washed once in PBSM, then resuspended in 20 ml PBSM+100 μl streptavidin microspheres (Miltenyi). The libraries were incubated for 5 min on ice with occasional shaking, then the cells were pelleted, the supernatant removed, resuspended in 20 ml PBSM, then separated on MACS LS columns (Miltenyi). The columns were washed once with 5 ml PBSM, then the bound cells were eluted with selective medium, brought to 10 ml final in selective medium, and grown at 30° C. with shaking overnight.

(ii) For the second round of sorting, the first round output from each of the three libraries was grown 24 hrs at 20° C. in selective medium containing 1% raffinose and 2% galactose to induce IgA expression. The libraries were pelleted, washed once in PBSF (PBS (Gibco)+0.1% bovine serum albumin), and resuspended in PBSF. Each library was divided in to two samples; the first sample was brought to 25 nM biotinylated FcαRI in PBSF, and the second sample was brought to 10 nM biotinylated FcαRI in PBSF. To each, rabbit anti myc-tag Dylight 488 (Rockland, Limerick, PA) was added at a 1:100 final dilution, and the samples were incubated for 1.5 hrs at room temperature with rotation. The samples were pelleted, washed once with PBSF, then incubated with PBSF+1:100 final streptavidin Dylight 633 (Invitrogen, Waltham, MA) for 5 min with rotation. The samples were then pelleted, washed once, resuspended in PBSF, filtered through a 40 μm strainer, then analyzed and sorted using flow cytometry on a FACS Aria cell sorter (Becton Dickinson Biosciences, San Jose, CA). For the L1 and L2 libraries, the 10 nM FcαRI sample was sorted, and for the EP library, the 25 nM FcαRI sample was sorted. In each case, the yeast showing the top 1-2% of signal were gated, collected, and grown overnight at 30° C. in selective medium.

(iii) For the third round of sorting, the cultures from the second round of sorting were inoculated in to selective medium+1% raffinose+2% galactose, and grown overnight at 20° to induce IgA expression. Cells from each of the three libraries were prepared and sorted as was done in the second round, except with the use of chicken anti myc tag FITC (Genetex, Irvine, CA) and Neutravidin Dylight 633 (Invitrogen), as detection reagents. Biotinylated FcαRI was used at 5 nM for the EP library, 2 nM for the L1 library, and 1 nM for the L2 library. In each case, the yeast showing the top 1-2% of signal were gated, collected, and grown overnight at 30° C. in selective medium.

(iv) The fourth round of sorting was completed on the EP and L1 libraries only. The cultures from the third round of sorting were inoculated into selective medium+1% raffinose+2% galactose, and grown overnight at 20° to induce IgA expression. Cells from each of the libraries were prepared and sorted as was done in the second round, except with the use of mouse anti c myc Dylight 488 (Invitrogen) and Streptavidin cy5 (Invitrogen), as detection reagents. Biotinylated FcαRI was used at 2 nM for the EP library, and 1 nM for the L1 library. In each case, the yeast showing the top 1-2% of signal were gated, collected, and grown overnight at 30° C. in selective medium.

1.3 Hot Spot Identification, Translation in Full-Length Immunoglobulins and SPR Validation Towards hFcαRI Plasmids were purified from the third (L2 library) and fourth (EP and L1 libraries) round cultures, transformed in to *E. coli*, plated on selective agar plates, grown overnight at 37°, and submitted to Genewiz (South Plainfield, NJ) for Sanger sequencing (Sanger et al (1975) J Mol Biol., 94(3): 441-8; Sanger et al (1977) PNAS USA., 74(12): 5463-7). The top clones were selected based on their frequency of appearance and were used to identify mutations enhancing the IgA2/hFcαRI interaction. The IgA2 residue positions are presented Table 1.

TABLE 1

Mutations identified by yeast display for enhancing IgA2 affinity towards hFcαRI.

| IgA2 sequence position (IMGT numbering for C-domain) | Initial residue in IgA2 | Mutation |
|---|---|---|
| CH2.10 | A | S |
| CH2.89 | L | I |
| CH2.91 | G | V |
| CH2.94 | Q | E |
| CH2.97 | N | Y, H |
| CH2.99 | G | W |
| CH3.105 | M | Y |
| CH3.109 | E | D |
| CH3.118 | Q | Y |
| CH3.124 | L | F |

Identified mutations were incorporated into the full-length IgA2 immunoglobulin having SEQ ID NO: 2, as single point mutation or in combination, and expressed transiently in HEK293 cells as described in Example 2. The same mutations were also incorporated into IgG1 isotype immunoglobulins having SEQ ID NOs: 3 and 6 and containing an engineered IgG1 Fc that was capable of binding to hFcαRI. The tested mutation sets are presented in Table 2 (based on SEQ ID NO: 2), Table 4 (based on SEQ ID NO: 3) and Table 6 (based on SEQ ID NO: 6).

The Fc variants were purified and assessed using surface plasmon resonance (SPR), measured against hFcαRI, to evaluate the effect of specific mutations on immunoglobulin affinity to hFcαRI. Interestingly, all mutations had a limited effect or no real effect on expression yield and aggregation propensity of the respective immunoglobulin. SPR data and aggregation content after capture are shown in Table 3, Table 5 and Table 7.

Finally, lead candidates were selected based on SPR and aggregation data and SPR experiments were repeated using a broader range of hFcαRI concentrations. The use of the adapted concentration range enabled a more precise measurement of the interaction between engineered immunoglobulin and hFcαRI. Results are shown in Table 8, Table 9 and Table 10.

TABLE 2

Tested mutation sets, based on parental IgA2 immunoglobulin SEQ ID 2.

| SEQ ID NO | Ref number | Mutation set |
|---|---|---|
| 2 | 2737 | — |
| 10 | 3240 | Q_CH2.94_E |
| 11 | 3241 | N_CH2.97_Y |
| 12 | 3242 | S_CH3.45_D |
| 13 | 3243 | M_CH3.105_Y |
| 14 | 3244 | Q_CH3.118_Y |
| 15 | 3245 | Q_CH2.94_E, N_CH2.97_Y |
| 53 | 3309 | Q_CH2.94_E, S_CH3.45_D |
| 54 | 3310 | Q_CH2.94_E, M_CH3.105_Y |
| 55 | 3311 | N_CH2.97_Y, S_CH3.45_D |
| 56 | 3312 | N_CH2.97_Y, M_CH3.105_Y |
| 57 | 3313 | S_CH3.45_D, M_CH3.105_Y |
| 28 | 3258 | M_CH3.105_Y, Q_CH3.118_Y |
| 58 | 3314 | Q_CH2.94_E, N_CH2.97_Y, M_CH3.105_Y |
| 59 | 3315 | N_CH2.97_Y, S_CH3.45_D, M_CH3.105_Y |
| 60 | 3316 | Q_CH2.94_E, S_CH3.45_D, M_CH3.105_Y |
| 29 | 3259 | M_CH3.105_Y, Q_CH3.118_Y, S_CH3.45_D |
| 30 | 3260 | Q_CH2.94_E, N_CH2.97_Y, S_CH3.45_D |
| 61 | 3317 | Q_CH2.94_E, N_CH2.97_Y, S_CH3.45_D, M_CH3.105_Y |
| 31 | 3261 | Q_CH2.94_E, N_CH2.97_Y, M_CH3.105_Y, Q_CH3.118_Y |
| 32 | 3262 | Q_CH2.94_E, N_CH2.97_Y, S_CH3.45_D, M_CH3.105_Y, Q_CH3.118_Y |
| 43 | 3273 | A_CH2.10_S |
| 44 | 3274 | L_CH2.89_I |
| 45 | 3275 | G_CH2.91_V |
| 50 | 3280 | N_CH2.97_H |
| 46 | 3276 | G_CH2.99_W |
| 47 | 3277 | E_CH3.109_D |
| 48 | 3278 | L_CH3.124_F |
| 49 | 3279 | L_CH2.89_I, G_CH2.91_V, Q_CH2.94_E, N_CH2.97_Y, G_CH2.99_W |

TABLE 3

Biophysical characterization of the Fc variants based on parental IgA2 SEQ ID No: 2.

| SEQ ID NO | Ref number | KD (1:1) (M)[1] | Maximum response[1] at 1000 nM hFcαRI (RU) | Aggregation[2] (%) |
|---|---|---|---|---|
| 2 | 2737 | 5.20E−07 | 168 | 11.5 |
| 10 | 3240 | 1.26E−07 | 253 | 12.40 |
| 11 | 3241 | 8.69E−08 | 235 | 10.60 |
| 12 | 3242 | 6.67E−08 | 261 | 9.93 |
| 13 | 3243 | 2.63E−08 | 278 | 11.30 |
| 14 | 3244 | 1.46E−07 | 194 | 8.60 |
| 15 | 3245 | 6.73E−08 | 250 | 14.00 |
| 53 | 3309 | 5.20E−08 | 242 | 8.30 |
| 54 | 3310 | 1.70E−08 | 213 | 8.10 |
| 55 | 3311 | 1.94E−08 | 246 | 9.60 |
| 56 | 3312 | 6.77E−09 | 251 | 7.50 |
| 57 | 3313 | 9.81E−09 | 194 | 8.90 |
| 28 | 3258 | 1.30E−08 | 278 | 10.20 |
| 58 | 3314 | 5.65E−09 | 247 | 8.40 |
| 59 | 3315 | 3.96E−09 | 223 | 9.90 |
| 60 | 3316 | 9.80E−09 | 226 | 7.40 |
| 29 | 3259 | 7.43E−09 | 289 | 10.40 |
| 30 | 3260 | 4.10E−08 | 306 | 13.10 |
| 61 | 3317 | 3.81E−09 | 244 | 11.90 |
| 31 | 3261 | 5.66E−09 | 289 | 13.60 |
| 32 | 3262 | 5.99E−09 | 294 | 16.70 |
| 43 | 3273 | 1.09E−07 | 244 | 13.50 |
| 44 | 3274 | 1.24E−07 | 189 | 11.00 |
| 45 | 3275 | 1.38E−07 | 247 | 10.30 |
| 50 | 3280 | 1.00E−07 | 188 | nd |
| 46 | 3276 | 1.43E−07 | 225 | 9.90 |
| 47 | 3277 | 9.20E−08 | 220 | 11.40 |

TABLE 3-continued

Biophysical characterization of the Fc variants based on parental IgA2 SEQ ID No: 2.

| SEQ ID NO | Ref number | KD (1:1) (M)[1] | Maximum response[1] at 1000 nM hFcαRI (RU) | Aggregation[2] (%) |
|---|---|---|---|---|
| 48 | 3278 | 1.60E−07 | 231 | 12.80 |
| 49 | 3279 | nd | nd | nd |

[1]Affinity and maximum response of engineered immunoglobulins towards hFcαRI were determined by SPR experiments, following the procedure described in Example 3.
[2]Aggregation propensity was measured following the procedure described in Example 2.
nd: not determined

TABLE 4

Tested mutation sets, based on parental IgG1 engineered immunoglobulin SEQ ID 3

| SEQ ID NO | Ref number | Mutation set |
|---|---|---|
| 3 | 2771 | — |
| 16 | 3246 | Q_CH2.94_E |
| 17 | 3247 | L_CH2.97_Y |
| 18 | 3248 | S_CH3.45_D |
| 19 | 3249 | M_CH3.105_Y |
| 20 | 3250 | Q_CH3.118_Y |
| 21 | 3251 | Q_CH2.94_E, L_CH2.97_Y |
| 62 | 3318 | Q_CH2.94_E, S_CH3.45_D |
| 63 | 3319 | Q_CH2.94_E, M_CH3.105_Y |
| 64 | 3320 | L_CH2.97_Y, S_CH3.45_D |
| 65 | 3321 | L_CH2.97_Y, M_CH3.105_Y |
| 66 | 3322 | S_CH3.45_D, M_CH3.105_Y |
| 33 | 3263 | M_CH3.105_Y, Q_CH3.118_Y |
| 67 | 3323 | Q_CH2.94_E, L_CH2.97_Y, M_CH3.105_Y |
| 68 | 3324 | L_CH2.97_Y, S_CH3.45_D, M_CH3.105_Y |
| 69 | 3325 | Q_CH2.94_E, S_CH3.45_D, M_CH3.105_Y |
| 34 | 3264 | M_CH3.105_Y, Q_CH3.118_Y, S_CH3.45_D |
| 35 | 3265 | Q_CH2.94_E, L_CH2.97_Y, S_CH3.45_D |
| 70 | 3326 | Q_CH2.94_E, L_CH2.97_Y, S_CH3.45_D, M_CH3.105_Y |
| 36 | 3266 | Q_CH2.94_E, L_CH2.97_Y, M_CH3.105_Y, Q_CH3.118_Y |
| 37 | 3267 | Q_CH2.94_E, L_CH2.97_Y, S_CH3.45_D, M_CH3.105_Y, Q_CH3.118_Y |
| 51 | 3281 | L_CH2.89_I, V_CH2.91, Q_CH2.94_E, L_CH2.97_Y, G_CH2.99_W |

TABLE 5

Biophysical characterization of Fc variants based on parental SEQ ID NO: 3

| SEQ ID NO | Ref number | KD (1:1) (M)[1] | Maximum response[1] at 1000 nM hFcαRI (RU) | Aggregation[2] (%) |
|---|---|---|---|---|
| 2 | 2737 | 5.20E−07 | 168 | 11.5 |
| 3 | 2771 | 2.70E−07 | 197 | 9.20 |
| 16 | 3246 | 8.72E−08 | 267 | 14.80 |
| 17 | 3247 | 1.45E−08 | 372 | 12.00 |
| 18 | 3248 | 5.75E−08 | 344 | 9.80 |
| 19 | 3249 | 2.06E−08 | 339 | 6.80 |
| 20 | 3250 | 1.04E−07 | 240 | 10.00 |
| 21 | 3251 | 1.22E−08 | 344 | 9.00 |
| 62 | 3318 | 4.38E−08 | 342 | 10.10 |
| 63 | 3319 | 1.51E−08 | 352 | 9.40 |
| 64 | 3320 | 4.81E−09 | 326 | 7.90 |
| 65 | 3321 | 1.64E−09 | 289 | 8.30 |
| 66 | 3322 | 1.00E−08 | 327 | 8.70 |
| 33 | 3263 | 9.56E−09 | 322 | 12.70 |
| 67 | 3323 | 9.56E−10 | 319 | 9.00 |
| 68 | 3324 | 7.81E−10 | 304 | 7.50 |
| 69 | 3325 | 8.47E−09 | 325 | 7.80 |
| 34 | 3264 | 3.81E−09 | 289 | 11.40 |
| 35 | 3265 | 5.02E−09 | 278 | 13.90 |
| 70 | 3326 | 5.84E−10 | 307 | 8.50 |

TABLE 5-continued

Biophysical characterization of Fc variants based on parental SEQ ID NO: 3

| SEQ ID NO | Ref number | KD (1:1) (M)[1] | Maximum response[1] at 1000 nM hFcαRI (RU) | Aggregation[2] (%) |
|---|---|---|---|---|
| 36 | 3266 | 5.57E−10 | 333 | 12.05 |
| 37 | 3267 | 3.84E−10 | 305 | 13.70 |
| 51 | 3281 | 1.87E−08 | 228 | nd |

[1]Affinity and maximum response of engineered immunoglobulins toward hFcαRI were determined by SPR experiment, following the procedure described in Example 3.
[2]Aggregation propensity was measured following the procedure described in Example 2.
nd: not determined

TABLE 6

Tested mutation sets, based on parental IgG1 engineered immunoglobulin SEQ ID 6

| SEQ ID NO | Ref number | Mutation set |
|---|---|---|
| 6 | 3084 | — |
| 22 | 3252 | Q_CH2.94_E |
| 23 | 3253 | L_CH2.97_Y |
| 24 | 3254 | S_CH3.45_D |
| 25 | 3255 | M_CH3.105_Y |
| 26 | 3256 | Q_CH3.118_Y |
| 27 | 3257 | Q_CH2.94_E, L_CH2.97_Y |
| 71 | 3327 | Q_CH2.94_E, S_CH3.45_D |
| 72 | 3328 | Q_CH2.94_E, M_CH3.105_Y |
| 73 | 3329 | L_CH2.97_Y, S_CH3.45_D |
| 74 | 3330 | L_CH2.97_Y, M_CH3.105_Y |
| 75 | 3331 | S_CH3.45_D, M_CH3.105_Y |
| 38 | 3268 | M_CH3.105_Y, Q_CH3.118_Y |
| 76 | 3332 | Q_CH2.94_E, L_CH2.97_Y, M_CH3.105_Y |
| 77 | 3333 | L_CH2.97_Y, S_CH3.45_D, M_CH3.105_Y |
| 78 | 3334 | Q_CH2.94_E, S_CH3.45_D, M_CH3.105_Y |
| 39 | 3269 | M_CH3.105_Y, Q_CH3.118_Y, S_CH3.45_D |
| 40 | 3270 | Q_CH2.94_E, L_CH2.97_Y, S_CH3.45_D |
| 79 | 3335 | Q_CH2.94_E, L_CH2.97_Y, S_CH3.45_D, M_CH3.105_Y |
| 41 | 3271 | Q_CH2.94_E, L_CH2.97_Y, M_CH3.105_Y, Q_CH3.118_Y |
| 42 | 3272 | Q_CH2.94_E, L_CH2.97_Y, S_CH3.45_D, M_CH3.105_Y, Q_CH3.118_Y |
| 52 | 3282 | L_CH2.89_I, V_CH2.91, Q_CH2.94_E, L_CH2.97_Y, G_CH2.99_W |

TABLE 7

Biophysical characterization of Fc variants based on parental SEQ ID NO: 6

| SEQ ID NO | Ref number | KD (1:1) (M)[1] | Maximum response[1] at 1000 nM hFcαRI (RU) | Aggregation[2] (%) |
|---|---|---|---|---|
| 2 | 2737 | 5.20E−07 | 168 | 11.5 |
| 6 | 3084 | 5.09E−07 | 146 | 10.30 |
| 22 | 3252 | 1.15E−07 | 212 | 9.20 |
| 23 | 3253 | 3.52E−08 | 359 | 11.30 |
| 24 | 3254 | 1.32E−07 | 276 | 12.00 |
| 25 | 3255 | 5.38E−08 | 300 | 13.90 |
| 26 | 3256 | 1.33E−07 | 194 | 11.70 |
| 27 | 3257 | 2.77E−08 | 376 | 9.80 |
| 71 | 3327 | 7.53E−08 | 303 | 9.30 |
| 72 | 3328 | 3.88E−08 | 342 | 8.70 |
| 73 | 3329 | 1.12E−08 | 369 | 12.70 |
| 74 | 3330 | 4.32E−09 | 275 | 13.80 |
| 75 | 3331 | 2.80E−08 | 342 | 14.60 |
| 38 | 3268 | 2.29E−08 | 341 | 13.60 |
| 76 | 3332 | 2.39E−09 | 294 | 11.70 |
| 77 | 3333 | 1.96E−09 | 238 | 9.10 |
| 78 | 3334 | 2.23E−08 | 353 | 7.50 |
| 39 | 3269 | 1.05E−08 | 353 | 12.00 |
| 40 | 3270 | 1.04E−08 | 365 | 11.70 |

TABLE 7-continued

Biophysical characterization of Fc variants based on parental SEQ ID NO: 6

| SEQ ID NO | Ref number | KD (1:1) (M)[1] | Maximum response[1] at 1000 nM hFcαRI (RU) | Aggregation[2] (%) |
|---|---|---|---|---|
| 79 | 3335 | 1.27E−09 | 282 | 8.30 |
| 41 | 3271 | 1.13E−09 | 371 | 15.20 |
| 42 | 3272 | 4.86E−10 | 371 | 14.70 |
| 52 | 3282 | 4.71E−08 | 235 | nd |

[1]Affinity and maximum response of engineered immunoglobulins toward hFcαRI were determined by SPR experiment, following the procedure described in Example 3.
[2]Aggregation propensity was measured following the procedure described in Example 2.
nd: not determined

TABLE 8

Affinity and maximum response of Fc variants, based on parental IgA2 (SEQ ID NO: 2), towards hFcαRI as determined by SPR experiment described in Example 3.

| SEQ ID NO | Ref number | KD (1:1) (M) | Max response at 31.25 nM hFcαRI (RU) |
|---|---|---|---|
| 13 | 3243 | 8.45E−09 | 157 |
| 28 | 3258 | 4.02E−09 | 179 |
| 59 | 3315 | 1.45E−09 | 190 |
| 30 | 3260 | 8.34E−09 | 185 |
| 61 | 3317 | 1.06E−09 | 201 |
| 32 | 3262 | 1.13E−09 | 191 |

TABLE 9

Affinity and maximum response of Fc variants, based on parental IgG1 engineered immunoglobulin (SEQ ID NO: 3), towards hFcαRI as determined by SPR experiment described in Example 3.

| SEQ ID NO | Ref number | KD (1:1) (M) | Max response at 31.25 nM hFcαRI (RU) |
|---|---|---|---|
| 17 | 3247 | 9.34E−09 | 259 |
| 64 | 3320 | 2.56E−09 | 252 |
| 66 | 3322 | 5.40E−09 | 220 |
| 68 | 3324 | 3.24E−10 | 249 |
| 70 | 3326 | 2.95E−10 | 248 |
| 37 | 3267 | 2.19E−10 | 268 |

TABLE 10

Affinity and maximum response of Fc variants, based on parental IgG1 engineered immunoglobulin (SEQ ID NO: 6), towards hFcαRI as determined by SPR experiment described in Example 3.

| SEQ ID NO | Ref number | KD (1:1) (M) | Max response at 31.25 nM hFcαRI (RU) |
|---|---|---|---|
| 23 | 3253 | 2.25E−08 | 187 |
| 25 | 3255 | 2.92E−08 | 139 |
| 27 | 3257 | 1.49E−08 | 239 |
| 73 | 3329 | 9.11E−09 | 229 |
| 76 | 3332 | 1.20E−09 | 237 |
| 77 | 3333 | 8.80E−10 | 189 |
| 40 | 3270 | 5.17E−09 | 290 |
| 79 | 3335 | 6.51E−10 | 240 |
| 41 | 3271 | 3.82E−10 | 322 |
| 42 | 3272 | 1.96E−10 | 313 |

1.4 Translation of Affinity Maturation to Enhancement of Alpha Effector Function in In Vitro Assays Lead candidates having a homodimeric Fc (SEQ ID NOs: 32, 37 and 42) were selected for their improved binding capacities towards hFcαRI. They were next tested in a PMN killing assay following the procedure described in Example 4. Potency ($EC_{50}$; concentration of the immunoglobulin required to produce 50% of its maximal effect) and efficacy (Emax; maximum effect expected of the immunoglobulin) results are shown in FIG. 1 to FIG. 4.

All tested candidates were active and were shown to have an improved efficacy compared to the parental IgA2 in a SK-BR-3 PMN killing assay (FIG. 1).

Figure 3:
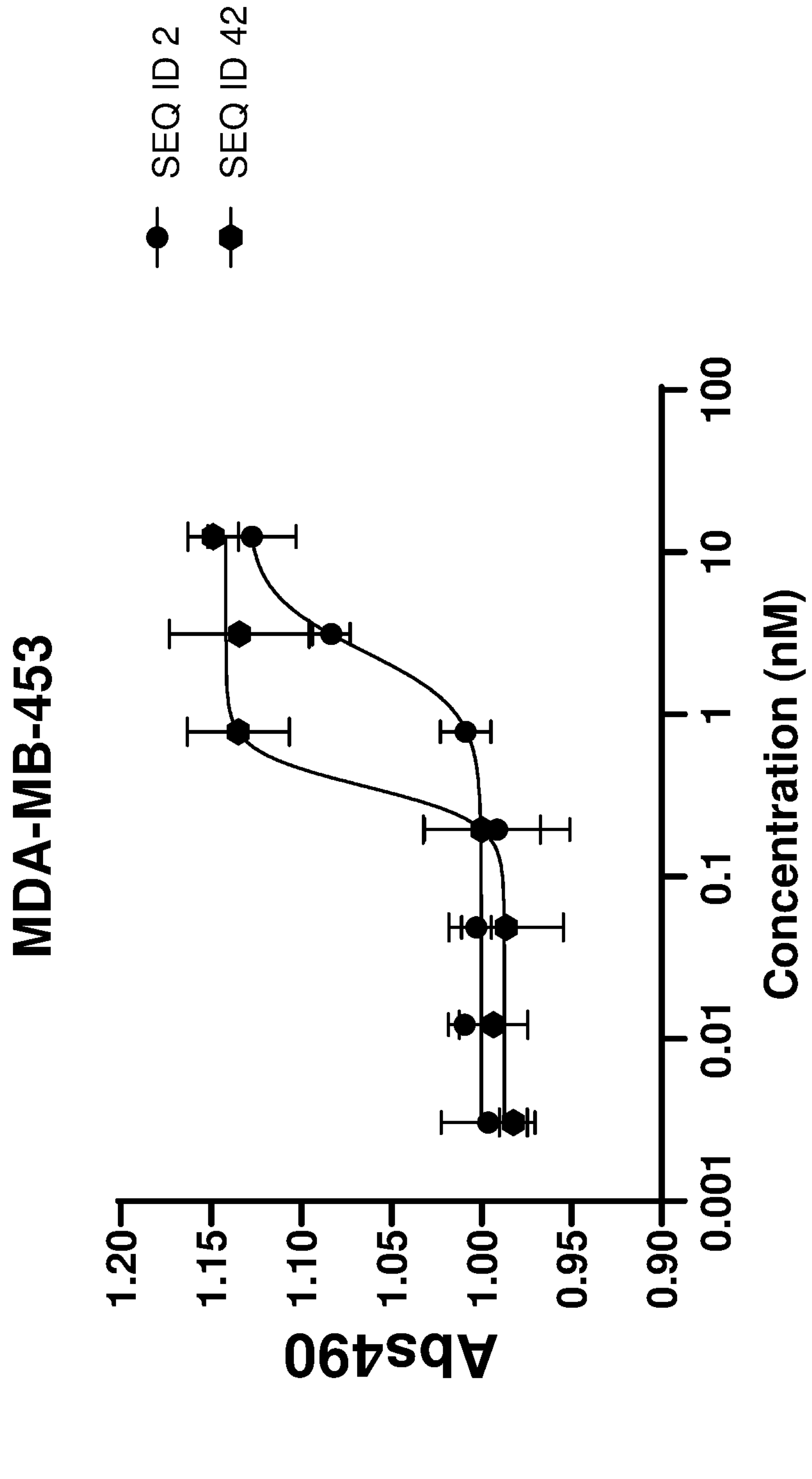
FIG. 3 shows PMN cytotoxicity of increasing concentrations of the Fc variant of SEQ ID NO: 42 and IgA2 (SEQ ID NO: 2) on MDA-MB-453 cells, in an ADCC assay as described in Example 4. The EC50 value for the variant comprising SEQ ID NO: 2 was 2.45 nM and the EC50 value for the variant comprising SEQ ID NO: 42 was 0.36 nM.

In addition, a substantial improvement in efficacy of up to 2-fold was shown in a PMN killing assay using Calu-3 cells (FIG. 2) where HER2 receptor density is known to be lower than SK-BR-3 cells (described in Example 4). Moreover, a substantial improvement in potency was shown for the variant having SEQ ID NO: 42 in a PMN killing assay on MDA-MB-453 cells, also known to express a lower level of HER2 receptors (FIG. 3). This improvement in potency was approximately 7-fold.

Figure 4:
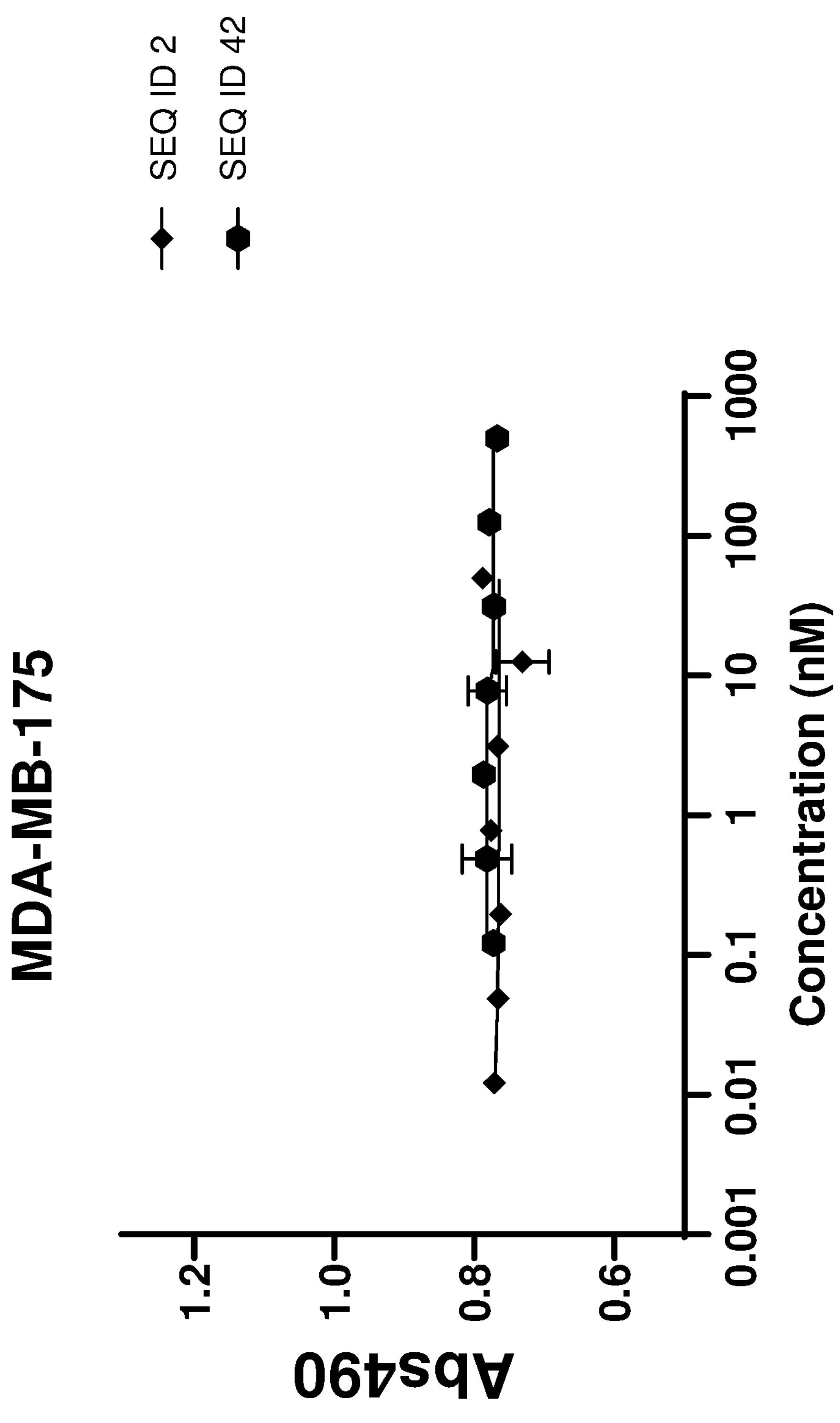
FIG. 4 shows PMN cytotoxicity of increasing concentrations of the Fc variant of SEQ ID NO: 42 (•) and parental IgA2 (SEQ ID NO: 2 (●)) on MDA-MB-175 cells, in an ADCC assay as described in Example 4.

Finally, the affinity matured variant having SEQ ID NO: 42 was tested in a PMN killing assay using MDA-MB-175 cells, known as the lowest HER2 expressing cell line, and showed no killing, even at very high concentrations (FIG. 4). This observation highlights the safe profile of the tested candidates.

Figure 5:
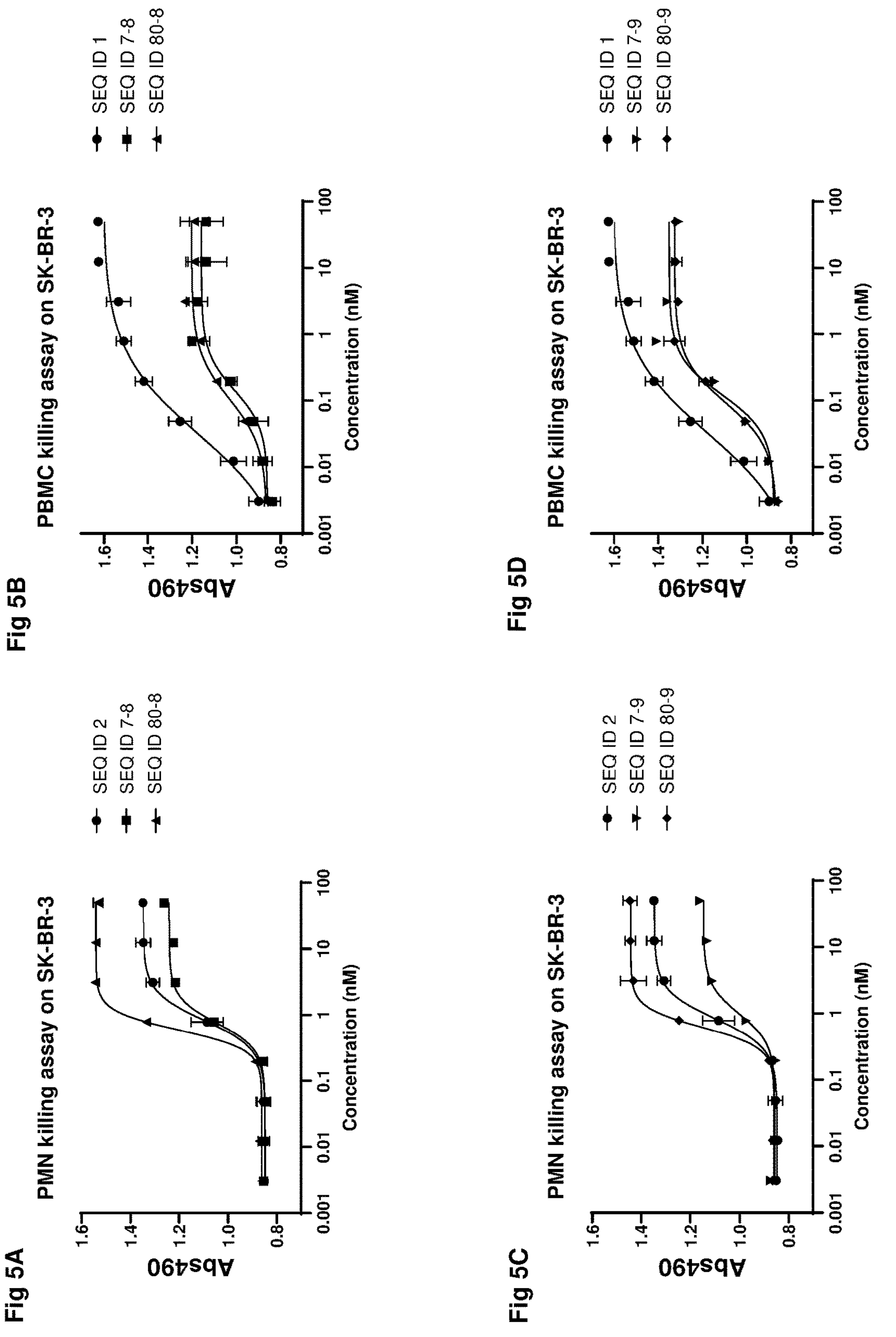
FIG. 5 shows PMN and PBMC cytotoxicity of increasing concentrations of the heterodimeric Fc candidates on SK-BR-3 cells, in an ADCC assay as described in Example 4.

The mutation set was applied to a heterodimeric Fc resulting in candidates comprising SEQ ID NOs: 7-8, SEQ ID NOs: 80-8, SEQ ID NOs: 7-9 or SEQ ID NOs: 80-9 (FIG. 5). Tested candidates SEQ ID NOs: 80-8 and SEQ ID NOs: 80-9 were shown to have better killing properties on SK-BR-3 cells in PMN killing assays, compared to their parental immunoglobulins and IgA2 (FIGS. 5A and 5C) but showed no effect in a PBMC killing assay to mediate gamma response (FIGS. 5B and 5D).

Example 2: Expression and Purification of Engineered Proteins

Nucleic acid sequences coding for heavy and light chains were synthesized at Geneart (LifeTechnologies) and cloned into a mammalian expression vector using restriction enzyme-ligation based cloning techniques. The resulting plasmids were co-transfected into HEK293T cells. In brief, for transient expression of immunoglobulins (IgG, IgA and engineered immunoglobulins), equal quantities of light chain and each engineered heavy chain vectors were co-transfected into suspension-adapted HEK293T cells using Polyethylenimine ((PEI) Ref. cat #24765 Polysciences, Inc.). Typically, 100 ml of cells in suspension at a density of 1-2 Mio cells per ml was transfected with DNA containing 50 μg of expression vector encoding the engineered heavy chain and 50 μg expression vectors encoding the light chain. The recombinant expression vectors were then introduced into the host cells and the construct produced by further culturing of the cells for a period of 7 days to allow for secretion into the culture medium (HEK, serum-fee medium) supplemented with 0.1% pluronic acid, 4 mM glutamine, and 0.25 μg/ml antibiotic.

The produced constructs were then purified from cell-free supernatant using immuno-affinity chromatography. Anti-Kappa LC resin (KappaSelect, GE Healthcare Life Sciences), equilibrated with PBS buffer pH 7.4 was incubated with filtered conditioned media using liquid chromatography system (Aekta pure chromatography system, GE Healthcare Life Sciences). The resin was washed with PBS pH 7.4 before the constructs were eluted with elution buffer (50 mM citrate, 90 mM NaCl, pH 2.7).

After capture, eluted proteins were pH neutralized using 1M TRIS pH 10.0 solution and polished using size exclusion chromatography technique (HiPrep Superdex 200 16/60, GE Healthcare Life Sciences). Purified proteins were finally formulated in PBS buffer pH 7.4.

Aggregation propensity was measured after capture and pH neutralization step using analytical size exclusion chromatography technique (Superdex 200 Increase 3.2/300 GL, GE Healthcare Life Sciences).

Example 3: SPR Measurement Against Human Fc Alpha Receptor (hFcαRI) or Rat Fc Alpha Receptor (rFcαR)

A direct binding assay was performed to characterize the binding of the Fc variants (in antibody format with light chain of SEQ ID NO: 4 against human FcαRI or rat FcαR.

Kinetic binding affinity constants (KD) were measured on a BIAcore® T200 instrument (GE Healthcare, Glattbrugg, Switzerland) at room temperature, with proteins diluted in running buffer 10 mM NaP, 150 mM NaCl, 0.05% Tween 20, pH7.6. A streptavidin sensor chip (Sensor Chip SA, GE Healthcare Life Sciences) immobilized with a biotinylated anti-kappa light chain scFv was used to capture engineered immunoglobulins, and recombinant human hFcαRI or recombinant rat FcαR was used as the analyte.

To serve as a reference, one flow cell did not capture any immunoglobulin. Binding data were acquired by subsequent injection of analyte dilution series on the reference and measuring flow cells. Zero concentration samples (running buffer only) were included to allow double referencing during data evaluation. For data evaluation, doubled referenced sensorgrams were analyzed by applying a 1:1 binding model analysis to generate the equilibrium dissociation constant (KD). The results related to rFCαR are summarized in Table 11.

This experiment showed that the candidate Fc variants were cross-reactive with human/rat FcαRI, which is a desired property for testing the candidates in in vivo disease models.

TABLE 11

SPR measurement and affinity for rFcαR

| SEQ ID NO | Ref number | KD (1:1) (M) | Maximum response at 250 nM rFcαR (RU) |
|---|---|---|---|
| 2 | 2737 | 1.87E−08 | 97 |
| 3 | 2771 | 2.37E−08 | 196 |
| 6 | 3084 | 5.78E−08 | 127 |
| 21 | 3251 | 4.43E−08 | 183 |
| 30 | 3260 | 1.43E−07 | 124 |
| 32 | 3262 | 3.19E−08 | 133 |
| 37 | 3267 | 2.39E−08 | 212 |
| 40 | 3270 | 7.72E−08 | 101 |
| 42 | 3272 | 4.57E−08 | 197 |

Example 4: Antibody-Dependent Cell Cytotoxicity (ADCC) Assay Method

Blood samples from healthy donors were collected from freshly drawn peripheral blood, according to the Swiss human research act (Basel tissue donor program—Prevomed). After lysis of red blood cells with ACK lysis buffer, Polymorphonuclear cells and Peripheral blood mononuclear cells (PMN and PBMC) were isolated by ficoll-paque gradient. PMN were used to characterize Alpha effector function of engineered immunoglobulin, whereas PBMC were used to characterize Gamma effector function.

Effector cells (freshly isolated PMN or PBMC cells) were added to HER2 expressing target cells (SK-BR-3, Calu-3, MDA-MB-453 or MDA-MB-175 cells, purchased at the American Type Culture Collection, Rockville MD) at an effector to target ratio of 20:1. SK-BR-3 is a breast cancer cell line overexpressing HER2. Calu-3 and MDA-MB-453 are lung and breast cancer cell lines respectively, overexpressing HER2 at a lower level compared to SK-BR-3 (Cheung et al., 2019). MDA-MD-175 is a breast cancer cell line expressing the lowest amount of HER2 (Crocker et al., 2005). PMN cell killing was not observed with any of the candidate Fc variants indicating a good safety profile towards a lower HER2 expressing cell line.

The immunoglobulin construct was added at the concentration indicated and the combination was mixed gently and then centrifuged at 260×g for 4 minutes without a break to encourage co-localization of target and effector cells. The assay was then incubated for 18 hours at 37° C. in 5% $CO_2$ in a standard tissue culture incubator. After 18 hours, the supernatant was used for LDH release measurements using Cytotox96 reagent (Promega) according to the manufacturer instructions. Absorbance at 490 nm was read on a Biotek Synergy HT plate reader. Data were analyzed and graphed using GraphPad Prism 6.0.

Example 5: Improvement of Engineered Immunoglobulins Pharmacokinetic (PK) Properties Compare to IgA 5.1 Engineered Immunoglobulin Material Production Nucleic acids coding for anti-HER2 engineered immunoglobulin heavy chain variants having sequence SEQ ID NO: 1, 2, 7, 8, 40, 80, 82, 83, 84 were synthesized at Geneart (LifeTechnologies) and cloned into a mammalian expression vector using restriction enzyme-ligation based cloning techniques. Selected N-glycosylation sites were removed by substitution of specific Asp residues by Ala residues. The resulting plasmids coding for the heavy chain were co-transfected with a plasmid coding for the light chain (SEQ ID NO: 4) into a mammalian expression system. For the HEK293T expression cell line, expression was performed according to procedure described Example 2. For the CHO-S expression cell line (Thermo), the following procedure was used. In brief, for protein transient expression, the expression vector was transfected into suspension-adapted CHO-S cells using ExpifectamineCHO transfecting agent (Thermo). Typically, 400 ml of cells in suspension at a density of 6 Mio cells per ml were transfected with DNA containing 400 μg of expression vector encoding the engineered protein. The recombinant expression vector was then introduced into the host cells for further secretion for seven days in culture medium (ExpiCHO expression media, supplemented with ExpiCHO feed and enhancer reagent (Thermo)). The expressed constructs were then purified from cell-free supernatant according to procedure described Example 2. Measured immunoglobulin concentrations in serum were plotted as a function of time and presented in FIG. 6 and FIG. 7. The material generated is described Tables 12 and 13.

TABLE 12

| Description of immunoglobulins produced in HEK293T mammalian system | |
|---|---|
| SEQ ID | Description, with numbering is according to IMGT numbering for C-domain |
| 1 | IgG1 |
| 2 | IgA2 |
| 7-8 | Heterodimer engineered IgG1<br>recruits CD89 via first half-Fc,<br>recruits FcγRs and FcRn via second half-Fc |
| 8-80 | Heterodimer engineered IgG1<br>recruits CD89 via first half Fc (affinity matured),<br>recruits FcγRs and FcRn via second half-Fc |

TABLE 13

| Description of immunoglobulins produced in CHO mammalian system | |
|---|---|
| SEQ ID | Description, with numbering is according to IMGT numbering for C-domain |
| 1 | IgG1 |
| 2 | IgA2 |
| 8-80 | Heterodimer engineered IgG1<br>recruits CD89 via first half Fc (affinity matured),<br>recruits FCgRs and FcRn via second half-Fc. |
| 40 | Homodimer engineered IgG1 |
| 82 | Homodimer engineered IgG1<br>N_CH2.20_A |
| 83 | Homodimer engineered IgG1<br>N_CH2.84.4_A |
| 84 | Homodimer engineered IgG1<br>N_CH2.20_A<br>N_CH2.84.4_A |

Figure 6:
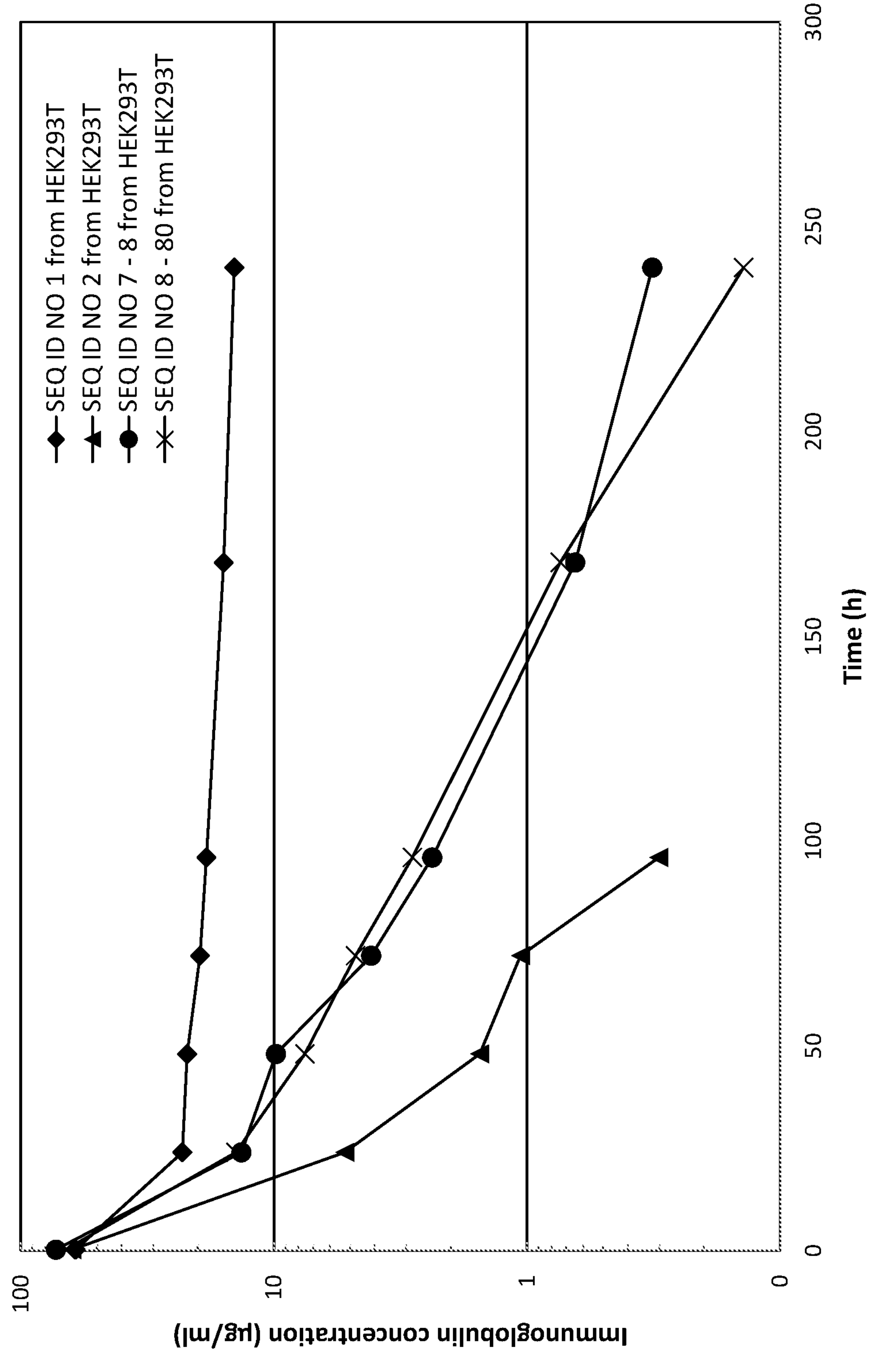
FIG. 6 shows serum-time concentration profiles of IgG, IgA and engineered immunoglobulins in mice. Concentration in serum of (♦) SEQ ID NO: 1 immunoglobulin from HEK293T, (▲) SEQ ID NO: 2 immunoglobulin from HEK293T, (●) engineered immunoglobulin SEQ ID No: 7-8 from HEK293T, (x) engineered immunoglobulin SEQ ID NO: 8-80 from HEK293T.

In line with the construct design, engineered immunoglobulins having sequence SEQ ID NO: 7-8 and SEQ ID NO: 8-80 bound to CD89 while retaining binding to FcRn and showed improved PK properties and an improved half-life compare to IgA immunoglobulin, as shown in FIG. 6. Moreover, as shown in FIG. 6, the affinity matured variant with SEQ ID 8-80 exhibits an identical PK profile as the parental construct with SEQ ID NO: 7-8. This shows that affinity maturation towards CD89 does impair engineered immunoglobulin PK properties.

Figure 7:
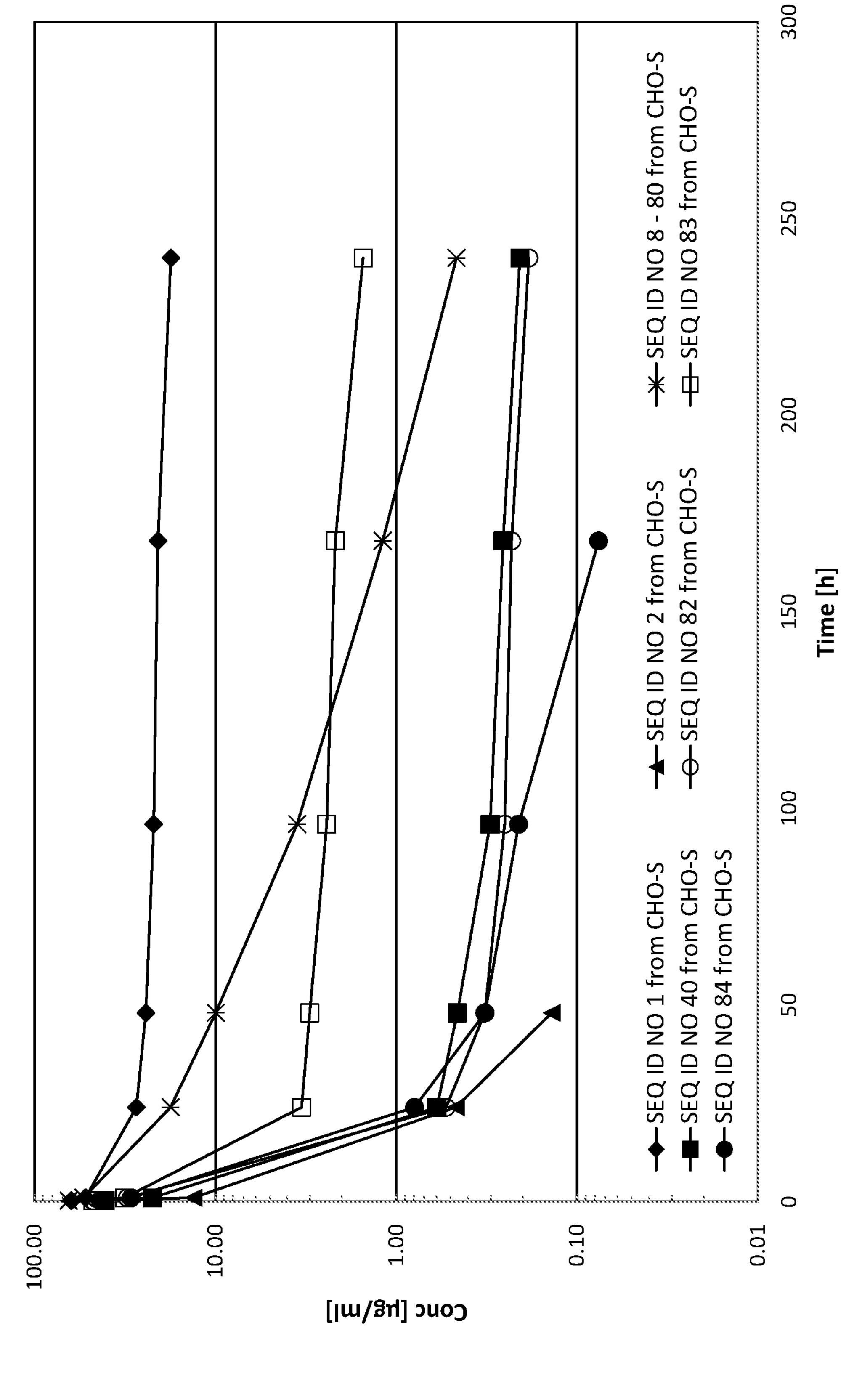
FIG. 7 shows serum-time concentration profiles of IgG, IgA and glyco-engineered immunoglobulins in mice. Concentration in serum of (♦) SEQ ID NO: 1 immunoglobulin from CHO-S, (▲) SEQ ID NO: 2 immunoglobulin from CHO-S, (x) engineered immunoglobulin SEQ ID No: 8-80 from CHO-S, (■) engineered immunoglobulin SEQ ID NO: 40 from CHO-S, (○) engineered immunoglobulin SEQ ID No: 82 from CHO-S, (□) engineered immunoglobulin SEQ ID NO: 83 from CHO-S, (●) engineered immunoglobulin SEQ ID NO: 84 from CHO-S.

Data presented in FIG. 7 show how the N-glycosylation pattern affects immunoglobulin PK. The PK properties of engineered immunoglobulins were improved compared to IgA and improved when individual the N-glycosylation site CH2.84.4 was removed (SEQ ID NO: 83).

5.1 Mouse Studies

Male CD1 mice were obtained by Charles River laboratories. Following arrival, all mice were maintained in a pathogen-free animal facility under a standard 12 h light/12 h dark cycle at 21° C. room temperature with access to food and water ad libitum. All mice received a single intravenous (IV) injection of IgG or IgA or engineered immunoglobulin (3 mg/kg) produced and purified as described above. Each compound was injected into three mice. Blood samples were collected into serum separator tubes via saphenous vein at various times post injection. The blood was allowed to clot at ambient temperature for at least 20 min. Clotted samples were maintained at room temperature until centrifuged, commencing within 1 h of the collection time. Each sample was centrifuged at a relative centrifugal force of 1500-2000×g for 5 min at 2-8° C. The serum was separated from the blood sample within 20 min after centrifugation and transferred into labeled 2.0-mL polypropylene, conical-bottom microcentrifuge tubes. Only animals that appeared to be healthy and that were free of obvious abnormalities were used for the study. All animal work performed was reviewed and approved by Novartis' Institutional Animal Care and Use Committee.

5.2 Immunoglobulin ELISA for Pharmacokinetic Studies

Immunoglobulin levels were measured by sequential sandwich ELISA. For IgA dosing, wells of Nunc Maxisorp microtiter plates were coated overnight at 4° C. with goat anti-human IgA (Southern Biotech, Cat #2053-01). For IgG and engineered immunoglobulins dosing, wells of Roche StreptaWell microtiter plates were coated 1 h at room temperature with biotinylated SB goat anti-human IgG (Southern Biotech, Cat #2049-08). After 1 h incubation with blocking buffer (PBS, 0.5% bovine serum albumin (BSA)), samples diluted in same blocking buffer were added to the blocked plates and incubated for 2 h at room temperature. After incubation, horseradish peroxidase-conjugated goat anti-human IgA (SouthernBiotech, Cat #2053-05) or horseradish peroxidase-conjugated goat anti-human IgG (SouthernBiotech, Cat #2049-05) were added and incubated for 1 h at room temperature. The plates were then incubated with substrate solution (BM Blue POD Substrate TMB, Roche, Cat #11484281001), and the reaction was stopped with 0.5M sulfuric acid. Absorbance was measured at 450 nm with a reduction at 650 nm using a plate reader. Between steps, plates were washed 3 times with washing buffer (0.05% Tween-20 in PBS).

Sequence Information

Table 14 describes the amino acid sequences (SEQ ID NOs) of the full length heavy chains comprising the variant Fc regions as described in the examples as well as the light chain used to generate complete antibodies. The Fc variants, full length heavy chains, light chains or complete antibodies as described herein can be produced using conventional recombinant protein production and purification processes.

All the sequences referred to in this specification (SEQ ID NOs) are found in Table 14. Ref No refers to an internal sequence reference number. Throughout the text of this application, should there be a discrepancy between the text of the specification (e.g., Table 14) and the sequence listing, the text of the specification shall prevail.

TABLE 14

Amino acid sequences

| SEQ ID NO: | AMINO ACID SEQUENCES | Ref No |
|---|---|---|
| 1 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvfifppkpkdtlmisrtpevtcvvvdvshedpevkfnwyvdg<br>vevhnaktkpreeqynstyrvvsvltvlhqdwlngkeykckvsnkalpapiektiskakgqprepqvytlp<br>psrdeltknqvsltclvkgfypsdiavewesngqpennykttppvldsdgsfflyskltvdksrwqqgnvf<br>scsvmhealhnhytqkslslsp | 2257 |
| 2 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltcltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscmvghea<br>lplaftqktidrla | 2737 |
| 3 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvflfrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgsqelprenykttasvldsdgsffvyskltvaaedwkkgdtfscmv<br>ghealplaftqksisrsp | 2771 |
| 4 | diqmtqspsslsasvgdrvtitcrasqdvntavawyqqkpgkapklliysasflysgvpsrfsgsrsgtdf<br>tltisslqpedfatyycqqhyttpptfgqgtkveikrtvaapsvfifppsdeqlksgtasvvcllnnfypr<br>eakvqwkvdnalqsgnsqesvteqdskdstyslsstltlskadyekhkvyacevthqglsspvtksfnrge<br>c | 2156 |
| 5 | qegdfpmpfisaksspvipldgsvkiqcqaireayltqlmiiknstyreigrrlkfwnetdpefvidhmda<br>nkagryqcqyrighyrfrysdtlelvvtglygkpflsadrglvlmpgenisitessahipfdrfslakege<br>lslpqhqsgehpanfslgpvdlnvsgiyrcygwynrspylwsfpsnalelvvtdsihqdyttqnhhhhhhg<br>lndifeaqkiewhe | 2922 |
| 6 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgsqelprenykttasvldsdgsffvyskltvaaedwkkgdtf<br>scmvghealplaftqksisrsp | 3084 |
| 7 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv | 3097 |

TABLE 14-continued

Amino acid sequences

| SEQ ID NO: | AMINO ACID SEQUENCES | Ref No |
| --- | --- | --- |
| | evhnaktkpreeqynstyrvvsvltvlhqdwlngkeykckvsnkalpapiektiskagqprepqvcllpps<br>rdeltknqvsiscaakgfypkdvlvrwlqgsqelprenykttasvldsdgsffvvskltvaaedwkkgdtf<br>scmvghealplaftqksisrsp | |
| 8 | evqlvesggglvqpggslrlscaasgfnikdtyihwvrqapgkglewvariyptngytryadsvkgrftis<br>adtskntaylqmnsiraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvfifppkpkdtlmisrtpevtcvvvdvshedpevkfnwyvdg<br>vevhnaktkpreeqynstyrvvsvltvlhqdwlngkeykckvsnkalpapiektiskagqprepqvytlpp<br>crdeltknqvslwclvkgfypsdiavewesngqpennykttppvldsdgsfflyskltvdksrwqqgnvfs<br>csvmhealhnhytqkslslsp | 3099 |
| 9 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpdvfifppkpkdtlmisrtpevtcvvvdvshedpevkfnwyvdg<br>vevhnaktkpreeqynstyrvvsvltvlhqdwlngkeykckvsnkalpapeektiskagqprepqvytlpp<br>crdeltknqvslwclvkgfypsdiavewesngqpennykttppvldsdgsfflyskltvdksrwqqgnvfs<br>csvmhealhnhytqkslslsp | 3101 |
| 10 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaepwnhgetftctaahpelktpltanitksgntfrpevhllpppseelalnelvtl<br>tclargfspkdvlvrwlqgsqelprekyltwasrqepsqgtttfavtsilrvaaedwkkgdtfsemvghea<br>lplaftqktidrla | 3240 |
| 11 | Evqlvesggglvqpggslrlscaasgfnikdtyihwvrqapgkglewvariyptngytryadsvkgrftis<br>adtskntaylqmnsiraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctitglrdasgatftwtpssgksavqgpper<br>dlcgcysvssvlpgcaqpwyhgetftctaahpelktpltanitksgntfrpevhllpppseelalnelvtl<br>tclargfspkdvlvrwlqgsqelprekyltwasrqepsqgtttfavtsilrvaaedwkkgdtfsemvghea<br>lplaftqktidrla | 3241 |
| 12 | evqlvesggglvqpggslrlscaasgfnikdtyihwvrqapgkglewvariyptngytryadsvkgrftis<br>adtskntaylqmnsiraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctitglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgdqelprekyltwasrqepsqgtttfavtsilrvaaedwkkgdtfsemvghea<br>lplaftqktidrla | 3242 |
| 13 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftqktidrla | 3243 |
| 14 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscmvghea<br>lplaftyktidrla | 3244 |
| 15 | evqlvesggglvqpggslrlscaasgfnikdtyihwvrqapgkglewvariyptngytryadsvkgrftis<br>adtskntaylqmnsiraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctitglrdasgatftwtpssgksavqgpper<br>dlcgcysvssvlpgcaepwyhgetftctaahpelktpltanitksgntfrpevhllpppseelalnelvtl<br>tclargfspkdvlvrwlqgsqelprekyltwasrqepsqgtttfavtsilrvaaedwkkgdtfscmvghea<br>lplaftqktidrla | 3245 |
| 16 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwlngkeykckvsnkalpapiektiskagqprepqvyllppsrdel<br>tknqvsltclakgfypkdvlvrwlqgsqelprenykttasvldsdgsffvyskltvaaedwkkgdtfscmv<br>ghealplaftqksisrsp | 3246 |

TABLE 14-continued

| Amino acid sequences | | |
|---|---|---|
| SEQ ID NO: | AMINO ACID SEQUENCES | Ref No |
| 17 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwyngkeykckvsnkalpapiektiskagqprepqvyllppsrdel<br>tknqvsltclakgfypkdvlvrwlqgsqelprenykttasvldsdgsffvyskltvaaedwkkgdtfscmv<br>ghealplaftqksisrsp | 3247 |
| 18 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgdqelprenykttasvldsdgsffvyskltvaaedwkkgdtfscmv<br>ghealplaftqksisrsp | 3248 |
| 19 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftqksisrsp | 3249 |
| 20 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgsqelprenykttasvldsdgsffvyskltvaaedwkkgdtfscmv<br>ghealplaftyksisrsp | 3250 |
| 21 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel<br>tknqvsltclakgfypkdvlvrwlqgsqelprenykttasvldsdgsffvyskltvaaedwkkgdtfscmv<br>ghealplaftqksisrsp | 3251 |
| 22 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvfifrpaledlllgseanvtcvvvdvshedpevkfnwyvdgv<br>evhnaktkpreeqynstyrvvsvltvlhedwlngkeykckvsnkalpapiektiskagqprepqvyllpps<br>rdeltknqvsltclakgfypkdvlvrwlqgsqelprenykttasvldsdgsffvyskltvaaedwkkgdtf<br>scmvghealplaftqksisrsp | 3252 |
| 23 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwyngkeykckvsnkalpapiektiskagqprepqvyllpps<br>rdeltknqvsltclakgfypkdvlvrwlqgsqelprenykttasvldsdgsffvyskltvaaedwkkgdtf<br>scmvghealplaftqksisrsp | 3253 |
| 24 | evqlvesggglvqpggslrlscaasgfnikdtyihwvrqapgkglewvariyptngytryadsvkgrftis<br>adtskntaylqmnsiraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3254 |
| 25 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftqksisrsp | 3255 |
| 26 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt | 3256 |

TABLE 14-continued

| Amino acid sequences | | |
|---|---|---|
| SEQ ID NO: | AMINO ACID SEQUENCES | Ref No |
| | aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgsqelprenykttasvldsdgsffvyskltvaaedwkkgdtf<br>scmvghealplaftyksisrsp | |
| 27 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgsqelprenykttasvldsdgsffvyskltvaaedwkkgdtf<br>scmvghealplaftqksisrsp | 3257 |
| 28 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftyktidrla | 3258 |
| 29 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftyktidrla | 3259 |
| 30 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctitglrdasgatftwtpssgksavqgpper<br>dlcgcysvssvlpgcaepwyhgetftctaahpelktpltanitksgntfrpevhllpppseelalnelvtl<br>tclargfspkdvlvrwlqgdqelprekyltwasrqepsqgtttfavtsilrvaaedwkkgdtfscmvghea<br>lplaftqktidrla | 3260 |
| 31 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaepwyhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftyktidrla | 3261 |
| 32 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaepwyhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftyktidrla | 3262 |
| 33 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftyksisrsp | 3263 |
| 34 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftyksisrsp | 3264 |
| 35 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel | 3265 |

TABLE 14-continued

Amino acid sequences

| SEQ ID NO: | AMINO ACID SEQUENCES | Ref No |
|---|---|---|
| | tknqvsltclakgfypkdvlvrwlqgdqelprenykttasvldsdgsffvyskltvaaedwkkgdtfscmv<br>ghealplaftqksisrsp | |
| 36 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftyksisrsp | 3266 |
| 37 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftyksisrsp | 3267 |
| 38 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftyksisrsp | 3268 |
| 39 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftyksisrsp | 3269 |
| 40 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvfifrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3270 |
| 41 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftyksisrsp | 3271 |
| 42 | evqlvesggglvqpggslrlscaasgfnikdtyihwvrqapgkglewvariyptngytryadsvkgrftis<br>adtskntaylqmnsiraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftyksisrsp | 3272 |
| 43 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpsledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscmvghea<br>lplaftqktidrla | 3273 |
| 44 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgsqelprekyltwasrqepsqgtttfavtsilrvaaedwkkgdtfscmvghea<br>lplaftqktidrla | 3274 |

TABLE 14-continued

Amino acid sequences

| SEQ ID NO: | AMINO ACID SEQUENCES | Ref No |
|---|---|---|
| 45 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctitglrdasgatftwtpssgksavqgpper dlcgcysvssvlpvcaqpwnhgetftctaahpelktpltanitksgntfrpevhllpppseelalnelvtl tclargfspkdvlvrwlqgsqelprekyltwasrqepsqgtttfavtsilrvaaedwkkgdtfscmvghea lplaftqktidrla | 3275 |
| 46 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctltglrdasgatftwtpssgksavqgpper dlcgcysvssvlpgcaqpwnhwetftctaahpelktpltanitksgntfrpevhllpppseelalnelvtl tclargfspkdvlvrwlqgsqelprekyltwasrqepsqgtttfavtsilrvaaedwkkgdtfscmvghea lplaftqktidrla | 3276 |
| 47 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctltglrdasgatftwtpssgksavqgpper dlcgcysvssvlpgcaqpwnhgetftctaahpelktpltanitksgntfrpevhllpppseelalnelvtl tclargfspkdvlvrwlqgsqelprekyltwasrqepsqgtttfavtsilrvaaedwkkgdtfscmvghda lplaftqktidrla | 3277 |
| 48 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctltglrdasgatftwtpssgksavqgpper dlcgcysvssvlpgcaqpwnhgetftctaahpelktpltanitksgntfrpevhllpppseelalnelvtl tclargfspkdvlvrwlqgsqelprekyltwasrqepsqgtttfavtsilrvaaedwkkgdtfscmvghea lplaftqktidrfa | 3278 |
| 49 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctltglrdasgatftwtpssgksavqgpper dlcgcysvssvipvcaepwyhwetftctaahpelktpltanitksgntfrpevhllpppseelalnelvtl tclargfspkdvlvrwlqgsqelprekyltwasrqepsqgtttfavtsilrvaaedwkkgdtfscmvghea lplaftqktidrla | 3279 |
| 50 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctltglrdasgatftwtpssgksavqgpper dlcgcysvssvlpgcaqpwhhgetftctaahpelktpltanitksgntfrpevhllpppseelalnelvtl tclargfspkdvlvrwlqgsqelprekyltwasrqepsqgtttfavtsilrvaaedwkkgdtfscmvghea lplaftqktidrla | 3280 |
| 51 | evqlvesggglvqpggslrlscaasgfnikdtyihwvrqapgkglewvariyptngytryadsvkgrftis adtskntaylqmnsiraedtavyycsrwggdgfyamdywgqgtlvtvssastkgpsvfplapsskstsggt aalgclvkdyfpepvtvswnsgaltsgvhtfpavlqssglyslssvvtvpssslgtqtyicnvnhkpsntk vdkkvepkscdkthtcppcpcchprvfifrpaledlllgseanvtcvvtglrdedpevkfnwyvdgvevhn aktkpreeqycgcysvvsvitvlhedwynwkeykckvsnkalpapiektiskagqprepqvyllppsrdel tknqvsltclakgfypkdvlvrwlqgsqelprenykttasvldsdgsffvyskltvaaedwkkgdtfscmv ghealplaftqksisrsp | 3281 |
| 52 | Evqlvesggglvqpggslrlscaasgfnikdtyihwvrqapgkglewvariyptngytryadsvkgrftis adtskntaylqmnslraedtavyycsrwggdgfyamdywgqgtlvtvssastkgpsvfplapsskstsggt aalgclvkdyfpepvtvswnsgaltsgvhtfpavlqssglyslssvvtvpssslgtqtyicnvnhkpsntk vdkkvepkscdkthtcppcpapellggpsvflfrpaledlllgseanvtcvvvdvshedpevkfnwyvdgv evhnaktkpreeqynstyrvvsvitvlhedwynwkeykckvsnkalpapiektiskagqprepqvyllpps rdeltknqvsltclakgfypkdvlvrwlqgsqelprenykttasvldsdgsffvyskltvaaedwkkgdtf scmvghealplaftqksisrsp | 3282 |
| 53 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp sqdvtvpcrvpppppcchprlslhrpaledlllgseanltctitglrdasgatftwtpssgksavqgpper dlcgcysvssvlpgcaepwnhgetftctaahpelktpltanitksgntfrpevhllpppseelalnelvtl tclargfspkdvlvrwlqgdqelprekyltwasrqepsqgtttfavtsilrvaaedwkkgdtfscmvghea lplaftqktidrla | 3309 |
| 54 | evqlvesggglvqpggslrlscaasgfnikdtyihwvrqapgkglewvariyptngytryadsvkgrftis adtskntaylqmnslraedtavyycsrwggdgfyamdywgqgtlvtvssasptspkvfplsldstpqdgnv vvaclvqgffpqeplsvtwsesgqnvtarnfppsqdasgdlyttssqltlpatqcpdgksvtchvkhytnp | 3310 |

TABLE 14-continued

Amino acid sequences

| SEQ ID NO: | AMINO ACID SEQUENCES | Ref No |
| --- | --- | --- |
| | sqdvtvpcrvpppppcchprlslhrpaledlllgseanltctltglrdasgatftwtpssgksavqgpper<br>dlcgcysvssvlpgcaepwnhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftqktidrla | |
| 55 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwyhgetftctaahpelktpltanitksgntfrpevhllpppseelalnelvtl<br>tclargfspkdvlvrwlqgdqelprekyltwasrqepsqgtttfavtsilrvaaedwkkgdtfscmvghea<br>lplaftqktidrla | 3311 |
| 56 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwyhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftqktidrla | 3312 |
| 57 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwnhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftqktidrla | 3313 |
| 58 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaepwyhgetftctaahpelktpltanitksgntfrpevhllpppseelalnelvtl<br>tclargfspkdvlvrwlqgsqelprekyltwasrqepsqgtttfavtsilrvaaedwkkgdtfscyvghea<br>lplaftqktidrla | 3314 |
| 59 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaqpwyhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftqktidrla | 3315 |
| 60 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctitglrdasgatftwtpssgksavqgpper<br>dlcgcysvssvlpgcaepwnhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftqktidrla | 3316 |
| 61 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssasptspkvfplsldstpqdgnv<br>vvaclvqgffpqeplsvtwsesgqnvtarnfppsqdasgdlyttssqltlpatqcpdgksvtchvkhytnp<br>sqdvtvpcrvpppppcchprlslhrpaledlllgseanltctltglrdasgatftwtpssgksavqgpper<br>dlcgcysvssvlpgcaepwyhgetftctaahpelktpltanitksgntfrpevhllpppseelalnelvtl<br>tclargfspkdvlvrwlqgdqelprekyltwasrqepsqgtttfavtsilrvaaedwkkgdtfscyvghea<br>lplaftqktidrla | 3317 |
| 62 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwlngkeykckvsnkalpapiektiskagqprepqvyllppsrdel<br>tknqvsltclakgfypkdvlvrwlqgdqelprenykttasvldsdgsffvyskltvaaedwkkgdtfscmv<br>ghealplaftqksisrsp | 3318 |
| 63 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn | 3319 |

TABLE 14-continued

| Amino acid sequences | | |
|---|---|---|
| SEQ ID NO: | AMINO ACID SEQUENCES | Ref No |
| | aktkpreeqycgcysvvsvltvlhedwlngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftqksisrsp | |
| 64 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwyngkeykckvsnkalpapiektiskagqprepqvyllppsrdel<br>tknqvsltclakgfypkdvlvrwlqgdqelprenykttasvldsdgsffvyskltvaaedwkkgdtfscmv<br>ghealplaftqksisrsp | 3320 |
| 65 | Evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwyngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftqksisrsp | 3321 |
| 66 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwlngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftqksisrsp | 3322 |
| 67 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel<br>tknqvsltclakgfypkdvlvrwlqgsqelprenykttasvldsdgsffvyskltvaaedwkkgdtfscyv<br>ghealplaftqksisrsp | 3323 |
| 68 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhqdwyngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftqksisrsp | 3324 |
| 69 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwlngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftqksisrsp | 3325 |
| 70 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpcchprvfifrpaledlllgseanvtcvvtglrdedpevkfnwyvdgvevhn<br>aktkpreeqycgcysvvsvltvlhedwyngkeykckvsnkalpapiektiskagqprepqvyllppsrdel<br>tknqvsltclakgfypkdvlvrwlqgdqelprenykttasvldsdgsffvyskltvaaedwkkgdtfscyv<br>ghealplaftqksisrsp | 3326 |
| 71 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwlngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3327 |
| 72 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwlngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftqksisrsp | 3328 |

TABLE 14-continued

Amino acid sequences

| SEQ ID NO: | AMINO ACID SEQUENCES | Ref No |
|---|---|---|
| 73 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwyngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3329 |
| 74 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwyngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftqksisrsp | 3330 |
| 75 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwlngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftqksisrsp | 3331 |
| 76 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvfifrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgsqelprenykttasvldsdgsffvyskltvaaedwkkgdtf<br>scyvghealplaftqksisrsp | 3332 |
| 77 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhqdwyngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftqksisrsp | 3333 |
| 78 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwlngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftqksisrsp | 3334 |
| 79 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scyvghealplaftqksisrsp | 3335 |
| 80 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqynstyrvvsvltvlhedwyngkeykckvsnkalpapiektiskagqprepqvcllpps<br>rdeltknqvsiscaakgfypkdvlvrwlqgdqelprenykttasvldsdgsffvvskltvaaedwkkgdtf<br>scmvghealplaftqksisrsp | 3367 |
| 81 | hhhhhh | |
| 82 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseaavtcvvvdvshedpevkfnwyvdgv<br>evhnaktkpreeqynstyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3400 |

TABLE 14-continued

| Amino acid sequences | | |
|---|---|---|
| SEQ ID NO: | AMINO ACID SEQUENCES | Ref No |
| 83 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseanvtcvvvdvshedpevkfnwyvdgv<br>evhnaktkpreeqyastyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3401 |
| 84 | evqlvesggglvqpggslrlscaasgfnikdtyihwvrqapgkglewvariyptngytryadsvkgrftis<br>adtskntaylqmnslraedtavyycsrwggdgfyamdywgqgtlvtvssastkgpsvfplapsskstsggt<br>aalgclvkdyfpepvtvswnsgaltsgvhtfpavlqssglyslssvvtvpssslgtqtyicnvnhkpsntk<br>vdkkvepkscdkthtcppcpapellggpsvflfrpaledlllgseaavtcvvvdvshedpevkfnwyvdgv<br>evhnaktkpreeqyastyrvvsvltvlhedwyngkeykckvsnkalpapiektiskagqprepqvyllpps<br>rdeltknqvsltclakgfypkdvlvrwlqgdqelprenykttasvldsdgsffvyskltvaaedwkkgdtf<br>scmvghealplaftqksisrsp | 3402 |

The invention claimed is:

1. An Fc variant of a parent Fc polypeptide comprised within a human IgA2 antibody, wherein the Fc variant exhibits altered binding to a FcαR or altered antibody dependent cell-mediated cytotoxicity (ADCC) as compared to the parent Fc polypeptide, wherein the Fc variant comprises at least one amino acid modification in the Fc region of the parent Fc polypeptide, wherein the at least one amino acid modification is selected from the group consisting of:

Q_CH2.94_E,
N_CH2.97_Y,
S_CH3.45_D,
M_CH3.105_Y,
Q_CH3.118_Y,
Q_CH2.94_E/N_CH2.97_Y,
Q_CH2.94_E/S_CH3.45_D,
Q_CH2.94_E/M_CH3.105_Y,
N_CH2.97_Y/S_CH3.45_D,
N_CH2.97_Y/M_CH3.105_Y,
S_CH3.45_D/M_CH3.105_Y,
M_CH3.105_Y/Q_CH3.118_Y,
Q_CH2.94_E/N_CH2.97_Y/M_CH3.105_Y,
N_CH2.97_Y/S_CH3.45_D/M_CH3.105_Y,
Q_CH2.94_E/S_CH3.45_D/M_CH3.105_Y,
M_CH3.105 Y/Q_CH3.118_Y/S_CH3.45_D,
Q_CH2.94_E/N_CH2.97_Y/S_CH3.45_D,
Q_CH2.94_E/N_CH2.97_Y/S_CH3.45_D/M_CH3.105_Y,
Q_CH2.94_E/N_CH2.97_Y/M_CH3.105_Y/Q_CH3.118_Y,
Q_CH2.94_E/N_CH2.97_Y/S_CH3.45_D/M_CH3.105_Y/Q_CH3.118_Y,
A_CH2.10_S,
L_CH2.89_I,
G_CH2.91_V,
N_CH2.97_H,
G_CH2.99_W,
E_CH3.109_D,
L_CH3.124_F, and
L_CH2.89_I/G_CH2.91_V/Q_CH2.94_E/N_CH2.97_Y/G_CH2.99_W, wherein numbering of the amino acid modification is according to IMGT numbering for C-domain.

2. The Fc variant according to claim 1, wherein the Fc variant has an increased affinity to human FcαRI of at least about 50-fold relative to the parent Fc polypeptide as measured by surface plasmon resonance.

3. The Fc variant according to claim 2, wherein the Fc variant has an increased affinity to human FcαRI of at least about 300-fold relative to the parent Fc polypeptide as measured by surface plasmon resonance.

4. The Fc variant according to claim 1, wherein the Fc variant increases antibody-dependent cell-mediated cytotoxicity by at least about 5-fold relative to the parent Fc polypeptide as measured in a MDA-MB-453 cell killing assay.

5. The Fc variant according to claim 1, wherein the Fc variant has an increased efficacy of at least about 2-fold in a Calu-3 cell killing assay relative to the parent Fc polypeptide.

6. The Fc variant of claim 1, wherein the Fc variant has increased FcαR affinity, or increased antibody dependent cell-mediated cytotoxicity, relative to an IgA2 antibody comprising a parent Fc polypeptide.

7. The Fc variant according to claim 6, wherein the antibody binds to a tumor antigen.

8. A pharmaceutical composition comprising an Fc variant according to claim 1, in combination with one or more pharmaceutically acceptable excipient, diluent or carrier.

9. The pharmaceutical composition according to claim 8, further comprising one or more additional active agents.

10. A method of treating a cell proliferative disorder or condition, comprising administering the Fc variant according to claim 1 to a subject in need thereof.

11. The method of claim 10 wherein the cell proliferative disorder or condition is selected from the group comprising: breast cancer, neuroblastoma, lymphoma, pancreatic ductal adenocarcinoma, melanoma, renal cell carcinoma, bladder cancer, colorectal cancer, non-small cell lung cancer, non-Hodgkins lymphoma and multiple myeloma.

* * * * *